(12) United States Patent
Chaparro et al.

(10) Patent No.: US 12,180,297 B2
(45) Date of Patent: Dec. 31, 2024

(54) ATP-DEPENDENT AGONISTS OF IMMUNE CELLS FUNCTION AS ANTICANCER AGENTS

(71) Applicant: Crosslink Therapeutics Inc., Cambridge, MA (US)

(72) Inventors: Rodolfo J. Chaparro, Cambridge, MA (US); Ronald D. Seidel, III, Natick, MA (US)

(73) Assignee: Crosslink Therapeutics Inc., Boston, MA (US)

(*) Notice: Subject to any disclaimer, the term of this patent is extended or adjusted under 35 U.S.C. 154(b) by 0 days.

(21) Appl. No.: 18/593,028

(22) Filed: Mar. 1, 2024

(65) Prior Publication Data

US 2024/0254254 A1    Aug. 1, 2024

Related U.S. Application Data

(63) Continuation of application No. PCT/US2023/014302, filed on Mar. 1, 2023.

(60) Provisional application No. 63/353,896, filed on Jun. 21, 2022, provisional application No. 63/330,120, filed on Apr. 12, 2022, provisional application No. 63/315,529, filed on Mar. 1, 2022.

(51) Int. Cl.

| | |
|---|---|
| *C07K 16/30* | (2006.01) |
| *C07K 14/525* | (2006.01) |
| *C07K 14/54* | (2006.01) |
| *C07K 14/55* | (2006.01) |
| *C07K 14/57* | (2006.01) |
| *C07K 14/705* | (2006.01) |
| *C07K 16/28* | (2006.01) |
| *A61K 38/00* | (2006.01) |

(52) U.S. Cl.
CPC ............ *C07K 16/30* (2013.01); *C07K 14/525* (2013.01); *C07K 14/5255* (2013.01); *C07K 14/5418* (2013.01); *C07K 14/5428* (2013.01); *C07K 14/5434* (2013.01); *C07K 14/5443* (2013.01); *C07K 14/55* (2013.01); *C07K 14/57* (2013.01); *C07K 14/70521* (2013.01); *C07K 14/70532* (2013.01); *C07K 14/70575* (2013.01); *C07K 16/2803* (2013.01); *C07K 16/2806* (2013.01); *C07K 16/2809* (2013.01); *C07K 16/2812* (2013.01); *C07K 16/2815* (2013.01); *C07K 16/2818* (2013.01); *C07K 16/2866* (2013.01); *C07K 16/2875* (2013.01); *C07K 16/2896* (2013.01); *A61K 38/00* (2013.01); *C07K 2318/10* (2013.01); *C07K 2319/30* (2013.01)

(58) Field of Classification Search
CPC .. C07K 16/30; C07K 14/525; C07K 14/5255; C07K 14/5418; C07K 14/5428; C07K 14/5434; C07K 14/5443; C07K 14/55; C07K 14/57; C07K 14/70521; C07K 14/70532; C07K 14/70575; C07K 16/2803; C07K 16/2806; C07K 16/2809
See application file for complete search history.

(56) References Cited

U.S. PATENT DOCUMENTS

| | | | |
|---|---|---|---|
| 6,284,879 | B1 | 9/2001 | Faustman |
| 6,830,913 | B1 | 12/2004 | Ling et al. |
| 11,390,683 | B2 | 7/2022 | Pastan et al. |
| 11,560,413 | B2 | 1/2023 | Kappes et al. |
| 2019/0248855 | A1 | 8/2019 | Kappes et al. |

FOREIGN PATENT DOCUMENTS

| WO | WO 2018/213612 A1 | 11/2018 |
|---|---|---|
| WO | WO 2019/051091 A1 | 3/2019 |

OTHER PUBLICATIONS

Licht et al. (Cent. Eur. J. Biol., 6(5): 785-801, 2011).*
Campoli et al. (Cent. Eur. J. Biol., 6(5): 785-801, 2011).*
Alum et al., "Structure and Mechanism of Human ABC Transporters," *Annual Reviews of Biophysics*, 52:275-300 (first published as a Review in Advance on Feb. 3, 2023).
Forero-Torres et al., "Phase I Trial of Weekly Tigatuzumab, an Agonistic Humanized Monoclonal Antibody Targeting Death Receptor 5 (DR5)," *Cancer Biotherapy and Radiopharmaceuticals*, 25(1): 13-19 (2010).
Freeman et al., "Unleashing TNF cytotoxicity to enhance cancer immunotherapy," *Trends in Immunology*, 42(12):1128-1142 (Dec. 2021).
Jansen et al., "Daratumumab, a human CD38 antibody, induces apoptosis of myeloma tumor cells via F c Receptor-Mediated cross-linking," (Poster Image), University Medical Center, Utrecht, the Netherlands, vol. 120, Issue 21, Nov. 16, 2012, p. 2974.
Paul et al., "The Molecular Mechanism of Natural Killer Cells Function and Its Importance in Cancer Immunotherapy," *Front. Immunol.*, vol. 8, Article 1124, 15 pages (Sep. 2017).

(Continued)

*Primary Examiner* — Nelson B Moseley, II
(74) *Attorney, Agent, or Firm* — Hoffmann & Baron, LLP

(57) ABSTRACT

The present disclosure provides polypeptide constructs that act as agonists of immune cell function when exposed to sufficient levels of ATP to cause their assembly into dimers or higher level complexes (e.g., trimers, tetramers, etc.). The complexes of the constructs are capable of stimulating immune cells (e.g., cytotoxic CD8+ T cell and/or NK cells) that function to promote anti-tumor immune responses. The constructs may be employed as anticancer agents/therapeutics for the treatment of solid tumors that have elevated levels of ATP.

27 Claims, 24 Drawing Sheets

Specification includes a Sequence Listing.

(56) References Cited

OTHER PUBLICATIONS

Atwell et al., "Structures of a minimal human CFTR first nucleotide-binding domain as a monomer, head-to-tail homodimer, and pathogenic mutant," *Protein Engineering, Design & Selection*, 23(5):375-384 (May 2010; published online Feb. 11, 2010).
Bajar et al., "A Guide to Fluorescent Protein FRET Pairs," *Sensors*, 16(9):1488, 24 pages (Sep. 14, 2016).
Bhagawati et al., "A mesophilic cysteine-less split intein for protein trans-splicing applications under oxidizing conditions," *PNAS*, 116(44):22164-22172 (Oct. 29, 2019).
Ernst et al., "Engineering ATPase Activity in the Isolated ABC Cassette of Human TAP1," *J. Biol. Chem.*, 281(37):27471-27480 (Sep. 15, 2006).
Ganesan et al., "Selective recruitment of γδ T cells by a bispecific antibody for the treatment of acute myeloid leukemia," *Leukemia*, 35(8):2274-2284 (Aug. 2021; published online Feb. 1, 2021).
Higashi et al., "Supramolecular Architectures of Nucleic Acid/Peptide Hybrids," *Int. J. Mol. Sci.*, 21(24):9458 (25 pages) (published online Dec. 12, 2020).
Insúa et al., "IMT504, the Prototype of the Immunostimulatory Oligonucleotides of the PyNTTTTGT Class, Increases the Number of Progenitors of Mesenchymal Stem Cells Both In Vitro and In Vivo: Potential Use in Tissue Repair Therapy," *Stem Cells*, 25(4):1047-1054 (Apr. 2007).
International Search Report and Written Opinion, International Application No. PCT/US2023/014302 (published under WO 2023/167947), 12 pages (Oct. 27, 2023).
Jackson et al., "TAP1 alleles in insulin-dependent diabetes mellitus: A newly defined centromeric boundary of disease susceptibility," *Proc. Natl. Acad. Sci. USA*, 90(23):11079-11083 (Dec. 1993).
Jin et al., "Prospects to improve chimeric antigen receptor T-cell therapy for solid tumors," *Immunotherapy*, 8(12):1355-1361 (2016; published online Dec. 21, 2016).
Kamata-Sakurai et al., "Antibody to CD137 Activated by Extracellular Adenosine Triphosphate Is Tumor Selective and Broadly Effective In Vivo without Systemic Immune Activation," *Cancer Discovery*, 11(1):158-175 (Jan. 2021).
Klein et al., "Human Immunoglobulin (Ig)M+IgD+ Peripheral Blood B Cells Expressing the CD27 Cell Surface Antigen Carry Somatically Mutated Variable Region Genes: CD27 as a General Marker for Somatically Mutated (Memory) B Cells," *J. Exp. Med.*, 188(9):1679-1689 (Nov. 2, 1998).
Lazar et al., "Engineered antibody Fc variants with enhanced effector function," *PNAS*, 103(11):4005-4010 (Mar. 14, 2006).
Liu et al., "Highly active CAR T cells that bind to a juxtamembrane region of mesothelin and are not blocked by shed mesothelin," *PNAS*, 119(19) e2202439119, 9 pages (May 10, 2022).
Locher, "Structure and mechanism of ATP-binding cassette transporters," *Phil. Trans. R. Soc. B*, 364:239-245 (2009; published online Oct. 28, 2008).
Loo et al., "The 'LSGGQ' Motif in Each Nucleotide-binding Domain of Human P-glycoprotein Is Adjacent to the Opposing Walker A Sequence," *J. Biol. Chem.*, 277(44):41303-41306 (2002).

Oancea et al., Structural arrangement of the transmission interface in the antigen ABC transport complex Tap, *PNAS*, 106(14):5551-5556 (Apr. 7, 2009).
Oliinyk et al., "Smallest near-infrared fluorescent protein evolved from cyanobacteriochrome as versatile tag for spectral multiplexing," *Nature Communications*, 10:279 (Jan. 17, 2019).
Perria et al., "Catalytic Site Modifications of TAP1 and TAP2 and Their Functional Consequences," *J. Biol. Chem.*, 281(52):39839-39851 (Dec. 29, 2006).
Procko et al., "Distinct Structural and Functional Properties of the ATPase Sites in an Asymmetric ABC Transporter," *Molecular Cell*, 24:51-62 (Oct. 6, 2006).
Procko et al., "Functionally Important Interactions between the Nucleotide-Binding Domains of an Antigenic Peptide Transporter," *Biochemistry*, 47(21):5699-5708 (May 27, 2008).
Propper et al., "Harnessing cytokines and chemokines for cancer therapy," *Nat. Rev. Clin. Oncol.*, 19(4):237-253 (Apr. 2022).
Reddington et al., "Secrets of a covalent interaction for biomaterials and biotechnology: SpyTag and SpyCatcher," *Current Opinion in Chemical Biology*, 29:94-99 (2015).
Saunders, "Conceptual Approaches to Modulating Antibody Effector Functions and Circulation Half-Life," *Front. Immunol.*, 10:1296, 20 pages (Jun. 7, 2019).
Schaaf et al., "Red-Shifted FRET Biosensors for High-Throughput Fluorescence Lifetime Screening," *Biosensors*, 8(4):99, 15 pages (Oct. 24, 2018).
Simpson et al., "Combining Mutations That Inhibit Two Distinct Steps of the ATP Hydrolysis Cycle Restores Wild-Type Function in the Lipopolysaccharide Transporter and Shows that ATP Binding Triggers Transport," *Mol. Biol. Phys.*, 10(4):e01931-19, 18 pages (Aug. 20, 2019).
Smith et al., "ATP Binding to the Motor Domain from an ABC Transporter Drives Formation of a Nucleotide Sandwich Dimer," *Mol. Cell.* 10(1):139-149 (Jul. 2022).
Stephanopoulos, "Peptide-Oligonucleotide Hybrid Molecules for Bioactive Nanomaterials," *Bioconjugate Chem.*, 30:1915-1922 (May 13, 2019).
Vakkasoglu et al., "D-helix influences dimerization of the ATP-binding cassette (ABC) transporter associated with antigen processing 1 (TAP1) nucleotide-binding domain," *PLoS ONE*, 12(5): e0178238 (May 23, 2017).
Veglia et al., "Myeloid-derived suppressor cells in the era of increasing myeloid cell diversity," *Nature Reviews Immunology*, 21(8):485-498 (Aug. 2021).
Wang et al., "IgG Fc engineering to modulate antibody effector functions," *Protein Cell*, 9(1):63-73 (2018).
Weatherill et al., "Towards a universal disulphide stabilised single chain Fv format: importance of interchain disulphide bond location and Lv-vH orientation," *Protein Engineering, Design & Selection*, 25(7):321-329 (2012; published online May 14, 2012).
Yang et al., "Myeloid-Derived Suppressor Cells in Tumors: From Mechanisms to Antigen Specificity and Microenvironmental Regulation," *Front. Immunol.*, 22 pages, (Jul. 22, 2020).
Zeimet et al., "Ovarian cancer stem cells," *Neoplasma*, 59(6):747-755 (2012).
International Preliminary Report on Patentability, International Application No. PCT/US2023/014302 (published under WO 2023/167947), 19 pages (Apr. 3, 2024).

* cited by examiner

FIG. 1
A
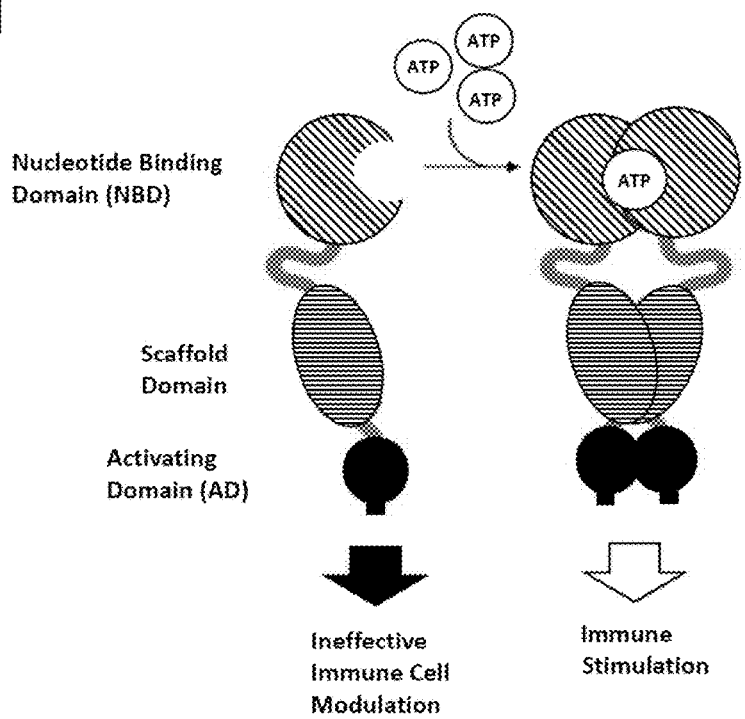
B
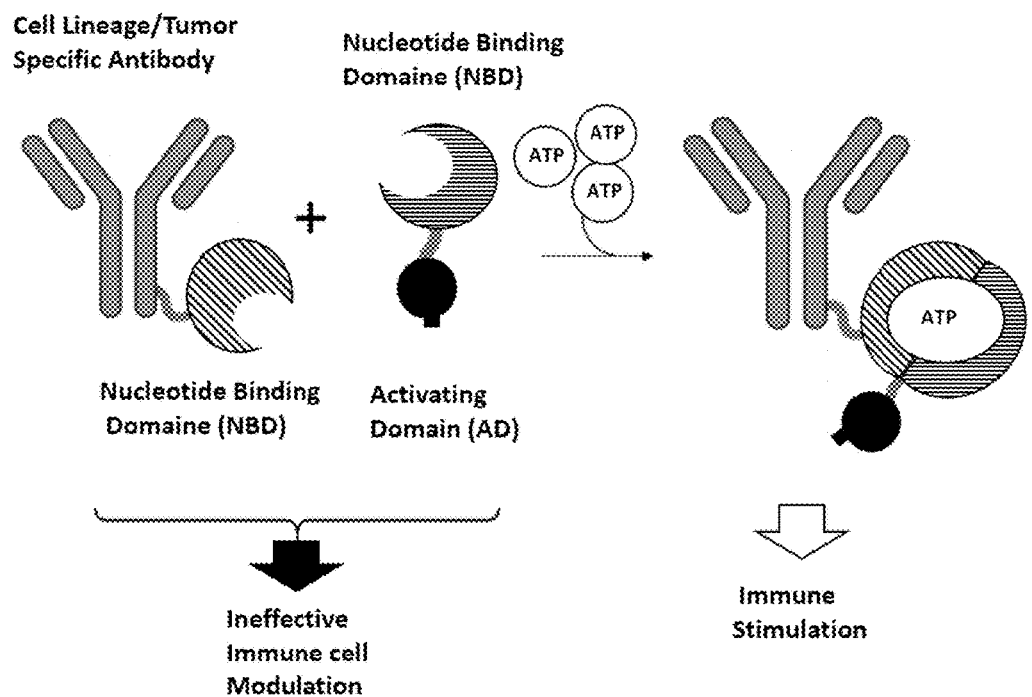

FIG. 2
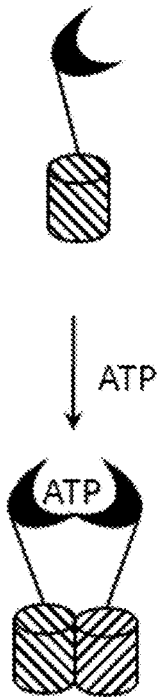
A
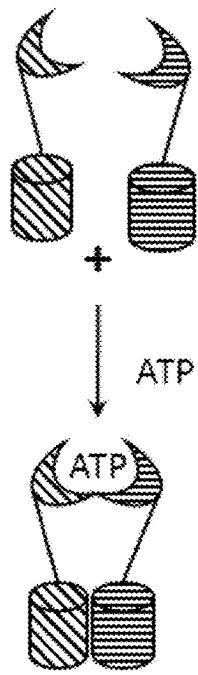
B

FIG. 3 (continued)
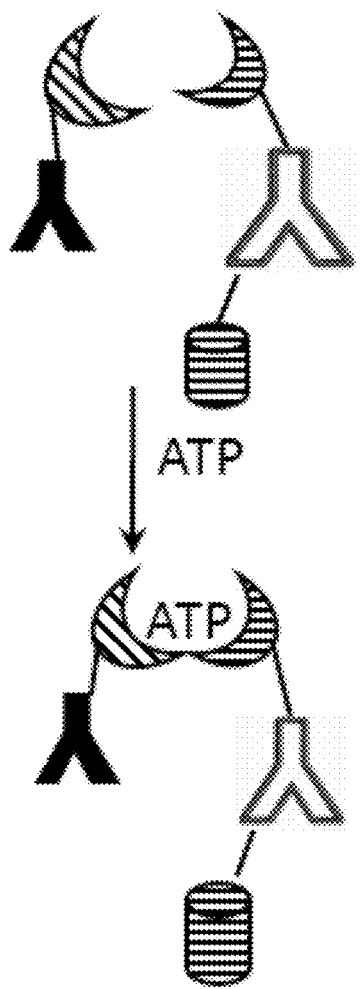
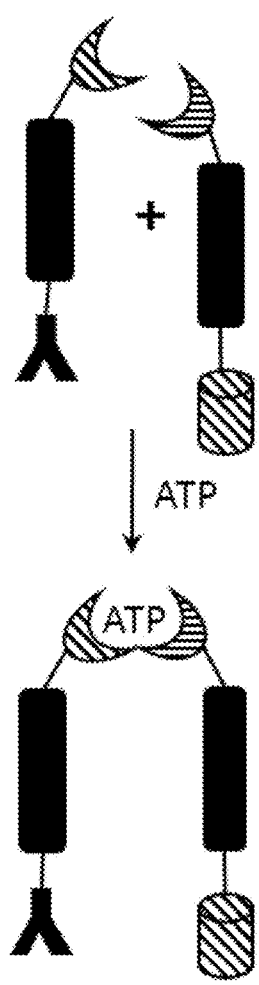
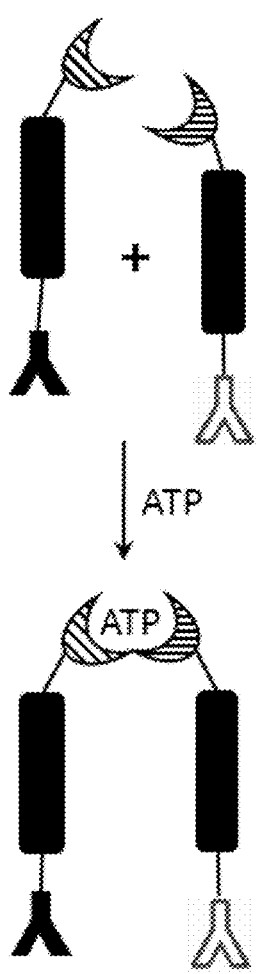

FIG. 3 (continued)
M
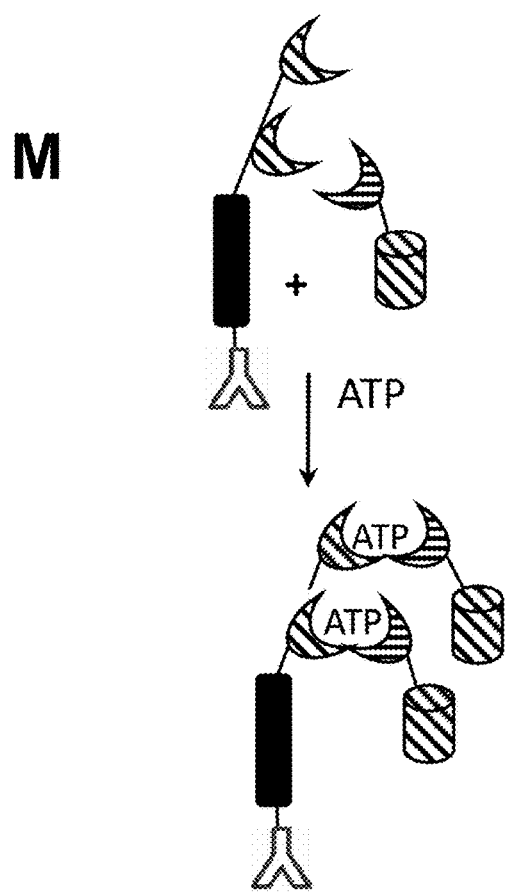
N
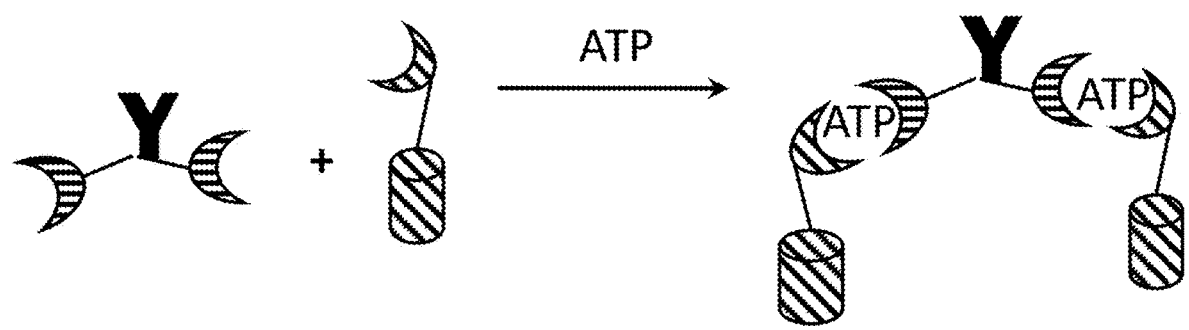

O

FIG. 4A (continued)
C
 ATP
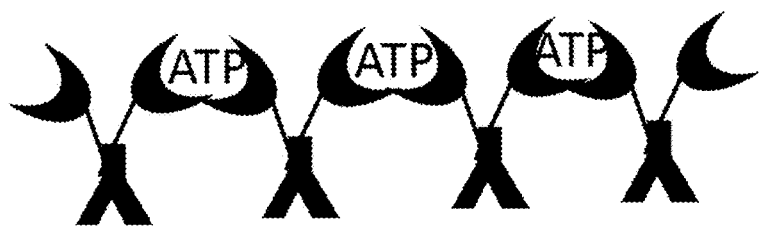
D
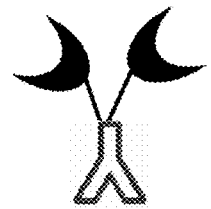
 ATP
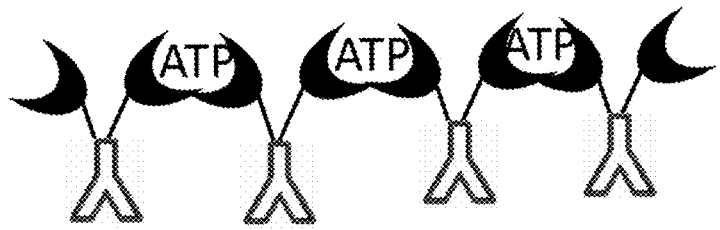

FIG. 4A (continued)
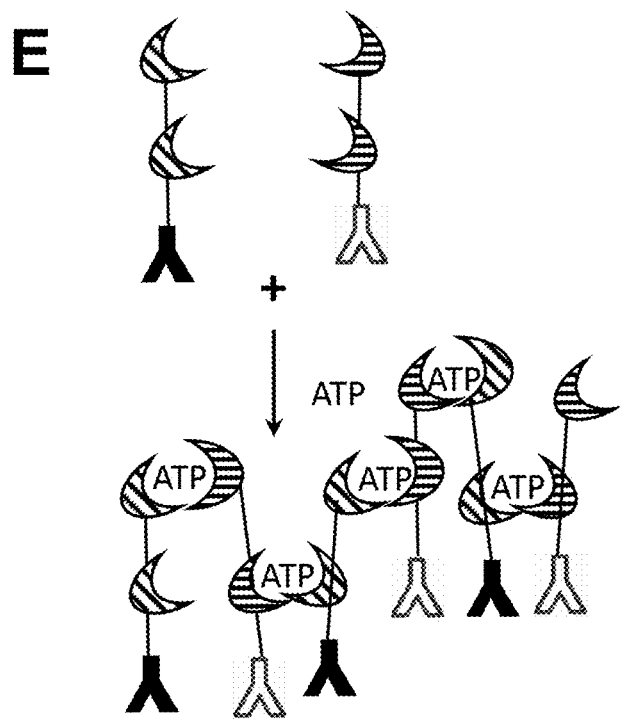
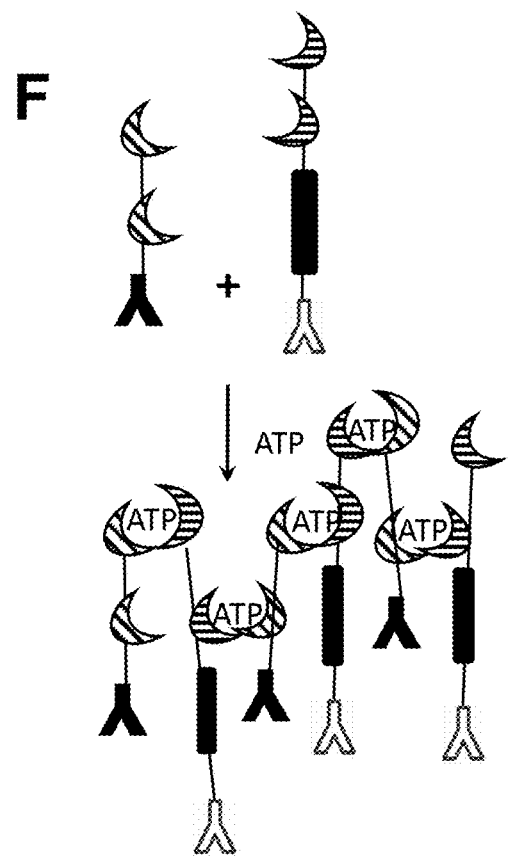

FIG. 4A (continued)
G
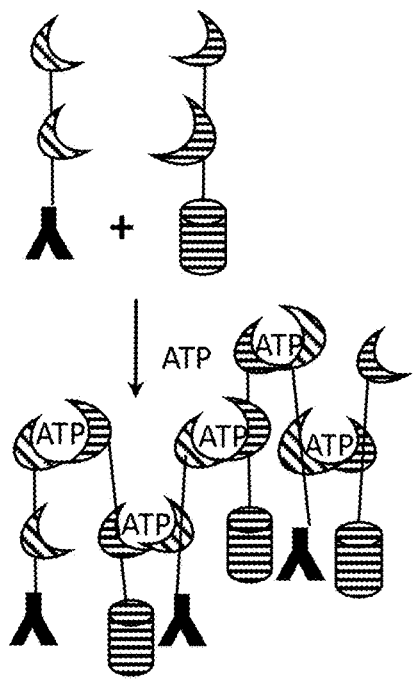
H
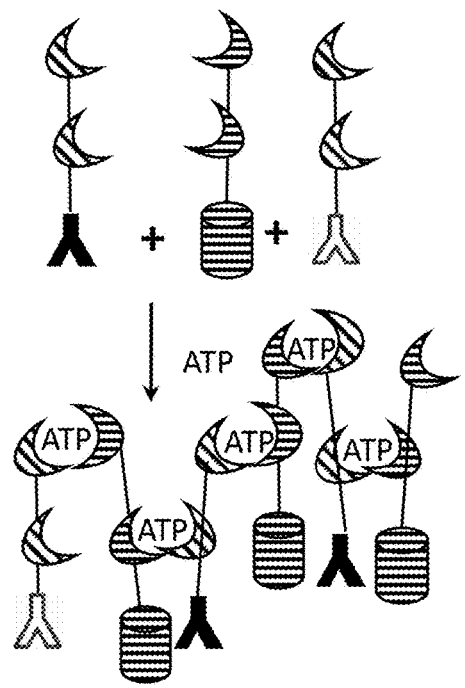
I
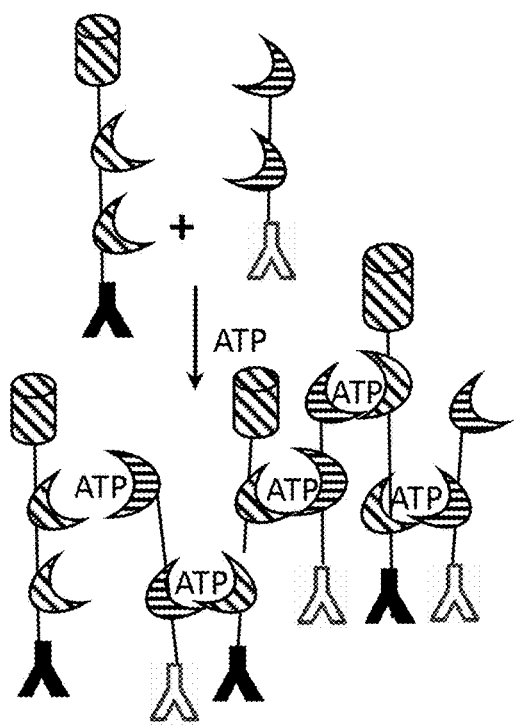

FIG. 4B
A
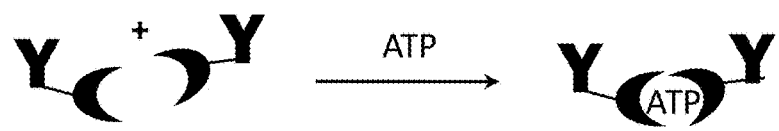
B
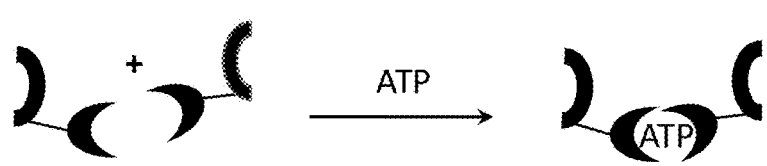
C
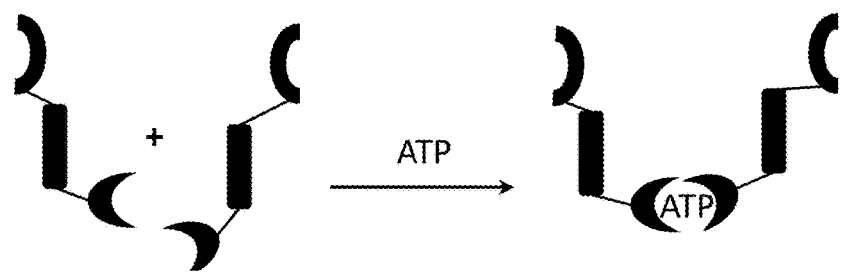
D
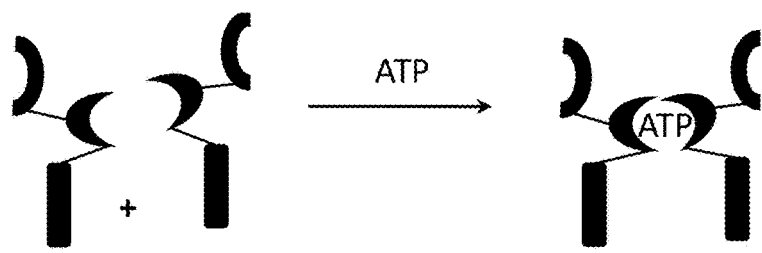
/ Optional linker sequence
Y Tumor specific binder (e.g., anti-HER2 or anti-PSMA)
▮ Scaffold (e.g., nondimerizing)
☾ Homodimerizing NBD
( Monovalent tumor specific binder single chain antibody such as a nanobody or scFv

FIG. 6

```
TAP1                   GLITPLHL----EGLV-----QFQDV------SFAYPNRPDVLVLQGLITFTLRPGEVTALVG   47
O95477|ABCA1_HUMAN     -RI--LDGGGQNDIL-----EIKEL------TKIYRR-KRKPAVDRICVGIPPGECFGLLG    46
P08183|MDR1_HUMAN      EGLMPNTL---EGNV-----TFGEV------VFNYPTRPDIPVLQGLSLEVKKGQTLALVG    47
P33527|MRP1_HUMAN      --RRPVKDGGGTNSI-----TVRNA------TFTW-ARSDPFTLNGITFSIPEGALVAVVG    47
P33897|ABCD1_HUMAN     ---GPLKIRGQVVDVBQGIICENI-----PI--VTPSGEVVASLNIRVEEGMHLLITG     49
P61221|ABCE1_HUMAN     GALSIVNL---PSNLEKE-----T------THRYC--ANAFKLIHRLP-IPRPGEVLGLVG    43
Q8NE71|ABCF1_HUMAN     PPLS------PPVL-----GLHGV------TFGY---QGQKPLFKNLDFGIDMDSRICIVG    41
P45844|ABCG1_HUMAN     -RFSSLPRRAA-VNI-----EFRDLSYSVPEGPWRKKGYKTLLKGISGKFNSGELVAIMG    54
                              :                  .         .                 *

TAP1                   PNGSGKSTVAALLQNLYQPTGGQLLLDGK--PLPQYEHRYLHRQVAAVGQEPQVFGRSLQ   105
O95477|ABCA1_HUMAN     VNGAGKSSTFKMLTGDTTVTRGDAFLNKN--SILS-NIHEVHQN-------------     87
P08183|MDR1_HUMAN      SSGCGKSTVVQLLERFYDPLAGKVLLDGK--EIKRLNVQWLRAHLGIVSQEPILFDCSIA   105
P33527|MRP1_HUMAN      QVGCGKSSLLSALLAEMDKVEGHVAIKGS--VAYVPQQAWIQND--SLRENILFGCQLE   102
P33897|ABCD1_HUMAN     PNGCGKSSLFRILGGLWPTYGGVLYKPPPQRMFYIPQRPYMSVG--SLRDQVIYPDSVE   106
P61221|ABCE1_HUMAN     TNGIGKSTALKILAGKQKPNLGKYDDPPDWQEI----LTYFRGS--EL--QNYFTKILE    94
Q8NE71|ABCF1_HUMAN     PNGVGKSTLLLLLTGKLTPTHGEMRKNHR--N--IGFFNQYAEQL----RMEETPT     91
P45844|ABCG1_HUMAN     PSGAGKSTLMNILAGYRETGMKGAVLI-N--GLPR-DLRCFRKV-------------     94
                       * ****:       :    *

TAP1                   ENIAYGLTQKPT-MEEITAAAVKSGAHSFI----SG--------LPQGYDTEVDEA      148
O95477|ABCA1_HUMAN     ----MGYCPQFDAITELLTGREHVEFFALLRGVPEKEVG--KVGEWAIRKLGLVKYGEKY   141
P08183|MDR1_HUMAN      ENIAYGDNSRVVSQEEIVRAAKEANIHAFI----ES--------LPNKYSTKVGDK      149
P33527|MRP1_HUMAN      EPYYRSVI--------QACALLPDL----EI---------LPSGDRTEIGEK          133
P33897|ABCD1_HUMAN     DMQRKGYSEQD---LEAIL---DVVHLHHIL--------QREGGWEAMCDW           143
P61221|ABCE1_HUMAN     DDLKAIIKPQY--VDQIPKAAKGT-VGSIL----DRKDET--KTQAIVCQQLDLTHLKERN 146
Q8NE71|ABCF1_HUMAN     EYLQRGFNLPY------QDARKCLGRFGL----ES--------HAHTIQ             122
P45844|ABCG1_HUMAN     ----SCYIMQDDMLLPHLTVQEAMVSAHL--KLQEKDEGRREMVKEILTALGLLSCANTR  149
                                                                                     :
```

FIG. 6 (continued)

```
TAP1           GSQLSGGQRQAVALARALIRKPCVLILDDATSALDANSQLVEQLL-YESPERYSRSVLL  207
O95477|ABCA1_HUMAN  AGNYSGGNKRKLSTAMALIGGPPVVFLDEPTTGMDPKARRFLWNCA--LSVVKEGRSVVL  199
P08183|MDR1_HUMAN   GTQLSGGQKQRIAIARALVRQPHILLLDEATSALDTESEKVVQEAL-DK--AREGRTCIV  206
P33527|MRP1_HUMAN   GVNLSGGQKQRVSLARAVYSNADIYLFDDPLSAVDAHVGKHIFENVIGPKGMLKNKTRIL  193
P33897|ABCD1_HUMAN  KDVLSGGEKQRIGMARMFYHRPKYALLDECTSAVSIDVEGKIFQAA-----KDAGIALLS  198
P61221|ABCE1_HUMAN  VEDLSGGELQRFACAVVCIQKADIFMFDEPSSYLDVKQRLKAAITI--RSLINPDRYIIV  204
Q8NE71|ABCF1_HUMAN  ICKLSGGQKARVVFAELACREPDVLILDEPTNNLDIESIDALGEAI-----NEYKGAVIV  177
P45844|ABCG1_HUMAN  TGSLSGGQRKRLAIALELVNNPPVMFFDEPTSGLDSASCFQVVSLM--KGLAQGGRSIIC  207
                   * **:           *          :                 :            .
TAP1           ITQHLSLVE-QADHILFLE-GGAIRE--GGTHQQLMEKK-------GCYWAMVQAPADAPE--  257
O95477|ABCA1_HUMAN  TSHSMEEC-EALCTRMAIMVNGRFRC-LGSVQHLKNRF------GDGYTIVRIAGSNPDLK  253
P08183|MDR1_HUMAN   IAHRLSTIQ-NADLIVVFQ-NGRVKE-HGTHQQLLAQK------GIYFSMVSVQAGTKRQ-  257
P33527|MRP1_HUMAN   VTHSMSYLP-QVDVIIVMS-GGKISE-MGSYQELLARD------GAFAEFLRTYASTEQEQ  245
P33897|ABCD1_HUMAN  ITHRPSLWK-YHTHLLQFDGEBGGWKF-----EKLDSAARLSLTEEKQRLEQQLAGIPKMQ  252
P61221|ABCE1_HUMAN  VEHDLSVLD-YLSDFICCLYG-VPSA-YGVVTMPF------SVREGINIFLDGYVPTENLR  256
Q8NE71|ABCF1_HUMAN  VSHDARLIT-ETNCQLWVEEQSVSQIDGDFEDYK--R------EVLEALGEVMVSRPRE-  228
P45844|ABCG1_HUMAN  TIHQPSAKLFELFDQLYVLSQGQCVY-RGKVCNLVPYL---R-------DLGLNCPTYH  255
                    :  .                                                     :
TAP1           --------------------------------------------------  257
O95477|ABCA1_HUMAN  PVQDFFGLAFPGSVLKEKHRNMLQYQLPSSLSSLA--             288
P08183|MDR1_HUMAN   --------------------------------------------------  257
P33527|MRP1_HUMAN   D-----------AEENGVT-----------------             253
P33897|ABCD1_HUMAN  R-----------RLQELCQIL---------------             262
P61221|ABCE1_HUMAN  FRDASLVFKVAETANEEEVKKMCMYKYPGMKKKMGEF             293
Q8NE71|ABCF1_HUMAN  --------------------------------------------------  228
P45844|ABCG1_HUMAN  NPADFVMEVASGEY----------------------             269
```

FIG. 7

UniProtKB - Q03519 (TAP2_HUMAN)

```
            10         20         30         40         50
    MRLPDLRPWT SLLLVDAALL WLLQGPLGTL LPQGLPGLWL EGTLRLGGLW
            60         70         80         90        100
    GLLKLRGLLG FVGTLLLPLC LATPLTVSLR ALVAGASRAP PARVASAPWS
           110        120        130        140        150
    WLLVGYGAAG LSWSLWAVLS PPGAQEKEQD QVNNKVLMWR LLKLSRPDLP
           160        170        180        190        200
    LLVAAFFFLV LAVLGETLIP HYSGRVIDIL GGDFDPHAFA SAIFFMCLFS
           210        220        230        240        250
    FGSSLSAGCR GGCFTYTMSR INLRIREQLF SSLLRQDLGF FQETKTGELN
           260        270        280        290        300
    SRLSSDTTLM SNWLPLNANV LLRSLVKVVG LYGFMLSISP RLTLLSLLHM
           310        320        330        340        350
    PFTIAAEKVY NTRHQEVLRE IQDAVARAGQ VVREAVGGLQ TVRSFGAEEH
           360        370        380        390        400
    EVCRYKEALE QCRQLYWRRD LERALYLLVR RVLHLGVQML MLSCGLQQMQ
           410        420        430        440        450
    DGELTQGSLL SFMIYQESVG SYVQTLVYIY GDMLSNVGAA EKVFSYMDRQ
           460        470        480        490        500
    PNLPSPGTLA PTTLQGVVKF QDVSFAYPNR PDRPVLKGLT FTLRPGEVTA
           510        520        530        540        550
    LVGPNGSGKS TVAALLQNLY QPTGGQVLLD EKPISQYEHC YLHSQVVSVG
           560        570        580        590        600
    QEPVLFSGSV RNNIAYGLQS CEDDKVMAAA QAAHADDFIQ EMEHGIYTDV
           610        620        630        640        650
    GEKGSQLAAG QKQRLAIARA LVRDPRVLIL DEATSALDVQ CEQALQDWNS
           660        670        680
    RGDRTVLVIA HRLQTVQRAH QILVLQEGKL QKLAQL
```

FIG. 11
A
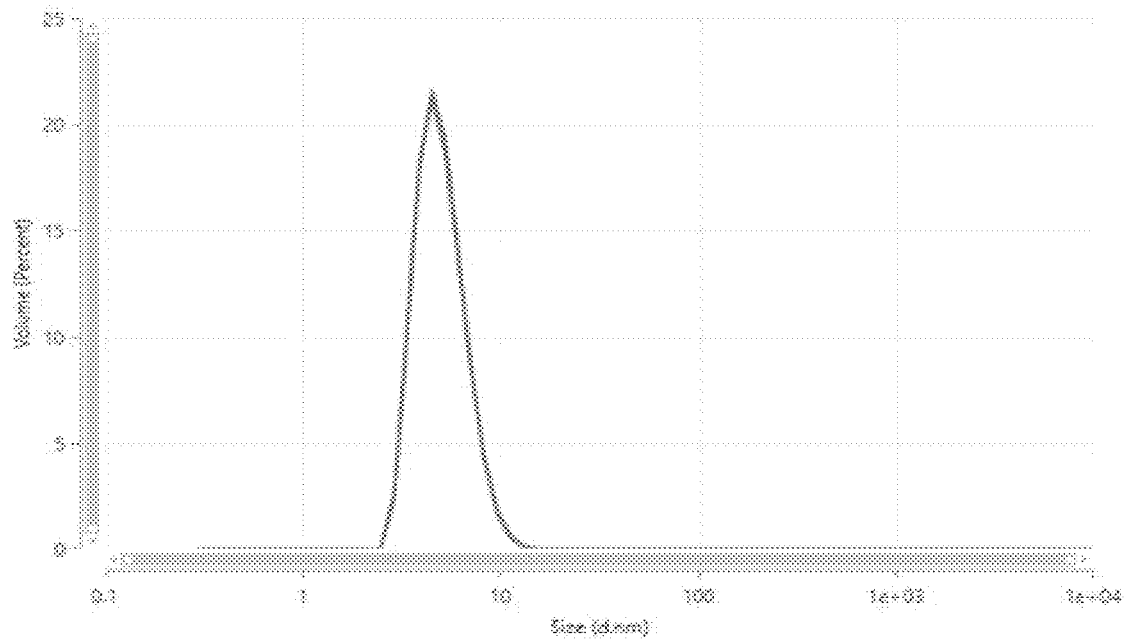
B
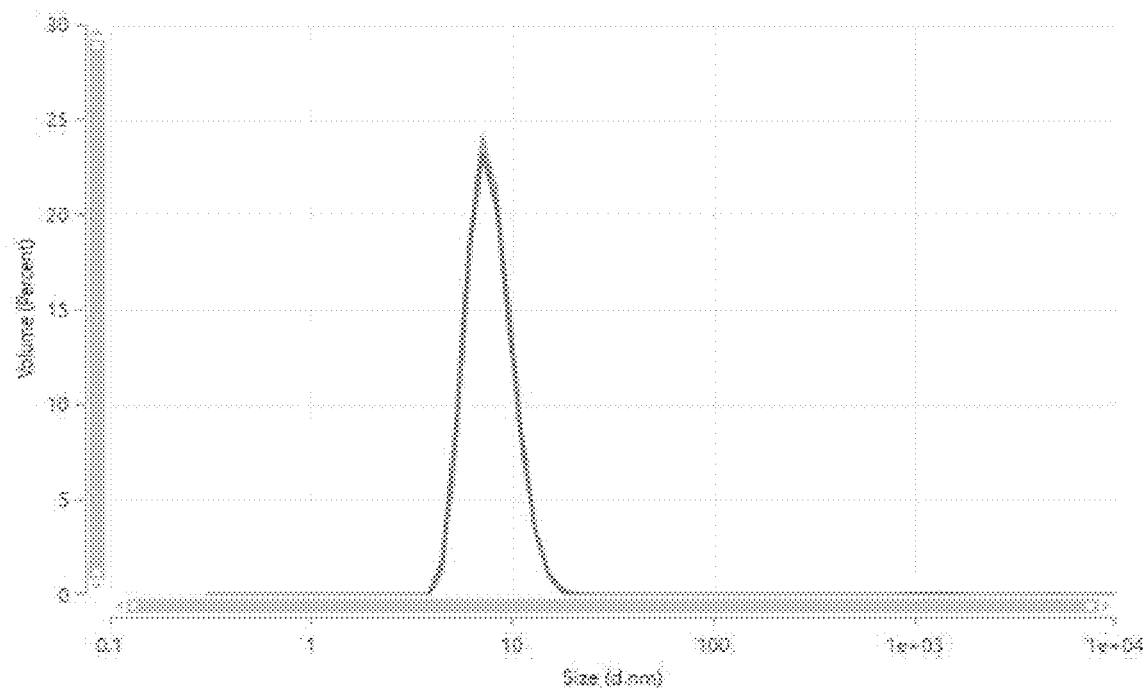

ATP-DEPENDENT AGONISTS OF IMMUNE CELLS FUNCTION AS ANTICANCER AGENTS

This application is a continuation of International Application No. PCT/US2023/014302, filed Mar. 1, 2023, which is incorporated herein by reference and which claims the benefit of U.S. Provisional Patent Application No. 63/315,529, filed Mar. 1, 2022, U.S. Provisional Patent Application No. 63/330,120, filed Apr. 12, 2022, and U.S. Provisional Patent Application No. 63/353,896, filed Jun. 21, 2022.

I. INCORPORATION OF SEQUENCE LISTING

The sequence listing in ST.26 XML format entitled 2974-3_PCT_CON_ST26.xml, created on Feb. 29, 2024, comprising 184,800 bytes, prepared according to 37 CFR 1.822 to 1.824, and submitted concurrently with the filing of this application, is incorporated herein by reference in its entirety.

II. INTRODUCTION

Potent anti-cancer therapies remain limited due to toxic systemic effects manifesting well below an ideal therapeutic dose. Immune agonists such as cytokines and anti-T cell receptor antibodies are particularly toxic when delivered systemically, potentially leading to severe adverse events such as cytokine release syndrome and death. Strategies to increase the effective dose of immunotherapeutic agents at the tumor relative to the systemic dose/toxicity (i.e. the "therapeutic index") include intratumoral administration and targeting of immunotherapies via linkage to antibodies against tumor-associated antigens ("TAA"). However, intratumor delivery is bespoke and invasive, and therefore has limited ability to reach large patient populations due to its associated surgical and logistical complexity. Newer agents that target TAAs attempt to impart a level of conditionality on the immune agonist wherein the agonist only accumulates to biologically effective concentrations at sites with sufficient density of the targeted TAA. TAA-targeted immune agonists suffer from serious limitations including, but not limited to: a small number of unique and validated TAAs expressed on the cell surface which are accessible by immunotherapeutics; low TAA density resulting in low efficacy; escape of cancers due to loss of TAA expression; TAAs that are not truly tumor specific, resulting in on-target/off-tumor toxicity; and the fact that each TAA requires a different drug of low therapeutic reach relative to systemic therapies.

Increasing the stoichiometry of immune agonism and/or TAA binding has also been explored as a means of enhancing the potency of TAA-targeted immunotherapies. For example, first generation bispecific T cell engagers such as blinatumomab comprise a single anti-TAA domain paired with a single anti-CD3 domain for a stoichiometry of 1:1. However, in the case of the bispecific T cell engager AFM11, an anti-TAA:anti-CD3 stoichiometry of 2:2 was used instead. This format was associated with more potent T cell mediated tumor cell killing in vitro, and importantly lowered the number of cytotoxic effector T cells required for tumor cell killing. However, a subsequent clinical trial of AFM11 revealed severe toxicity requiring termination of the study. A conceptually similar stoichiometric increase for the Fc domain of an antibody-like molecule showed a similar increase in in vitro potency. Such stoichiometric modifications likely act through avidity enhancements in TAA and immune receptor engagement. In addition, crosslinking of immune receptors such as Fc receptors or T cell receptors is known to amplify signal transduction through these receptors and signaling pathways, leading to more potent immune responses. Therefore, more potent tumor-targeting, including reducing effector T cell and antigen density requirements are potentially possible by engaging immune receptors with stoichiometrically enhanced immunotherapeutics. However, those enhanced immunotherapeutics have resisted clinical translation due to safety concerns.

A targeted immunotherapy could avoid the aforementioned liabilities of current immunotherapies by exploiting tumor characteristics that are both generalizable to most/all tumors, critical to tumor survival, and are highly expressed relative to normal tissues. The tumor microenvironment (TME) comprises the vasculature, immune and supportive cells, the extracellular matrix and local molecules around the tumor. The TME shares features across many different tumor types including a low pH, high extracellular adenosine triphosphate (ATP) content, limited oxygen levels (hypoxia), a leaky vasculature and the presence of tumor proteases (e.g. MMPs). Among these features, extracellular ATP is an excellent candidate for exploitation in the generation of novel classes of immunotherapeutics as it is a product of an altered and essential tumor metabolic program that is common to most if not all tumors. Extracellular ATP is also observed at very high levels in the TME (50-1000 μM) relative to normal tissues (less than ~0.1 μM).

III. SUMMARY

The present disclosure includes and provides molecular constructs comprising nucleotide binding domains (NBDs) that enable the use of tumor ATP as a trigger for the conditional (ATP-dependent) assembly of potent cancer therapeutic agents at the tumor. NBD-containing constructs form dimers or higher order complexes in the presence of ATP levels found in TMEs. The NBD-containing constructs find use as, among other things, therapeutic agents for treating various cancers. Therapies employing the constructs are designed to take advantage of the fact that ATP driven complexation (e.g., dimerization) can result in agents that recruit immune cells into the TME and/or stimulate immune cells in the TME. Stimulation may take place by, for example, multimerizing the immunomodulatory protein domains presented to immune cells as a result of ATP driven complexation of the constructs, producing more effective stimulation of the immune cells than single immunomodulatory protein sequences that cannot cause, for example, cross linking of their receptors. Dimers or other higher order complexes of NBD-containing constructs may also act through other mechanisms including targeted ADCC (antibody-dependent cell-mediated cytotoxicity) and/or CDC (complement-dependent cytotoxicity) of tumor cells. Because the elevation in ATP levels relative to surrounding tissue is virtually universal in TMEs, the constructs provide a mechanism for treating diverse tumor types. Moreover, because the individual constructs that have not undergone assembly into dimers or higher order constructs have either limited or no ability to bring about immune stimulation, the elevated ATP levels in TMEs that can bring about dimerization or complex formation can drive strong local stimulation with a lesser effect in non-tumor tissues where ATP is at a lower concentration. Accordingly, the constructs, which can assemble immunomodulatory amino acid sequences into multivalent states in the presence of ATP levels found in TME, may be used to modulate immune cell action in TMEs and bring about selective immune-mediated anti-tumor actions.

The NBD-containing constructs also offer several other advantages including trans- and cis-targeting. Cis-targeting by the NBD-containing constructs can effect stimulation of tumor-infiltrating leukocytes (e.g., by providing immune stimulator agonists such as IL-2 or CD28) resulting in amplification of the anti-tumor immune response. When trans-targeted against TAAs, the constructs result in immune mediated cytolysis of tumor cells bearing the TAAs, which adds an additional tumor-specific action beyond that resulting from localized elevations in ATP levels. Regardless of the targeting scheme employed (e.g., cis- or trans-targeting), the constructs permit the use of diverse immunomodulator domains derived from, for example, CD40L, CD28, IFN-g, IL-12, etc., each of which acts through receptors that require cross linking. Other advantages of the NBD-containing constructs described herein include their relatively small size, which permits penetration into tumor tissue, and their reduced diffusion from the TME, due to their increased size where they assemble into dimers or higher order complexes.

In addition to describing the constructs, the present disclosure also provides for methods of their preparation and methods of their use.

IV. BRIEF DESCRIPTION OF THE DRAWINGS

FIG. 1 provides at A a diagram of a construct of the present disclosure comprising a NBD with an ATP binding site, a scaffold domain (scaffold aa sequence), and an immune cell activating domain (AD) joined by linker sequences. The right side of the diagram in A also shows dimerization of the construct in the presence of a sufficient ATP concentration for the binding site to be substantially occupied (e.g., a concentration in the range of the Kd of ATP binding to the NBD or a higher concentration). At B, FIG. 1 provides: (i) a first construct comprising a tumor-specific binder (exemplified as a bivalent cell lineage or tumor-specific antibody but it may be a monovalent binder such as a scFv or nanobody) and a first NBD of a heterodimerizing NBD pair joined by a linker; and (ii) a second construct comprising a second NBD of the heterodimerizing NBD pair joined by a linker. The right side of the diagram at B shows the formation of a heterodimer of the first and second constructs due to dimerization of the NBD domains in the presence of ATP.

FIG. 2 provides a series of constructs (structures A to E) comprising a NBD and an AD with the constructs of structures C, D, and E also comprising scaffold sequences that may be non-dimerizing or may be interspecific. The elements of each construct are joined by independently selected optional linkers. The figure also shows the formation of dimers of the constructs in the presence of ATP.

FIG. 3 provides a series of construct pairs (structures A to O). In A-I, the first construct in each pair comprises one or more NBDs and a tumor-specific binder that binds to a TAA and the second construct of the pair comprises a NBD and an AD and/or a monovalent immune cell engager. In J-M, the first construct in each pair comprises one or more NBDs and an immune cell engager and the second construct of the pair comprises a NBD and an AD. Each of construct pairs E-I, L, and M has a scaffold in at least one of the constructs. In N and O the first construct in each pair comprises a tumor-specific binder and two NBDs, and the second construct of the pair comprises a NBD and an AD. The constructs in O also comprise a scaffold sequence. FIG. 3 also shows the formation of dimers of the constructs in the presence of ATP. The elements of each construct are joined by independently selected optional linkers.

FIG. 4A provides a series of constructs (see A, C, and D), pairs of constructs (B, E, F, G, and I), or a triplet of constructs (at H) that comprise two or more NBDs and can polymerize to form a complex in the presence of ATP (e.g., in a TME). In some instances, one or more of the constructs comprises a scaffold sequence and each construct may be joined by independently selected optional linkers. The figure also shows the formation of complexes in the presence of ATP comprising the constructs present in each case.

FIG. 4B shows examples of a NBD bound to a tumor-specific binder (e.g., antibody such as anti-mesothelian) that form homodimers in the presence of elevated ATP, such as is found in the tumor environment. In (A) the construct comprises a bivalent antibody that may be monospecific or bispecific and accordingly gives rise to tetramer or tetramer-like complex in the presence of ATP. The molecules need not comprise a Fc domain and may have two antigen binding domains (e.g., VHHs or scFVs tumor-specific antigen binders) and still remain bivalent. In (B), (C), and (D) the homodimerizing constructs comprise a NBD monovalent single chain antibody. The tumor-specific binders in (A) to (D) may be, for example, anti-HER2, anti-mesothelin, anti-EpCAM, anti-CLA-4, or anti-PSMA. When scaffold sequences are present they may be an immunoglobulin Fc peptide (such as an IgG1 Fc) that can bind any one or more of FcγRI, FcγRII, FcγRIII receptors and/or C1q proteins. Complexes, capable of binding to one or more of those proteins can bring about antibody-dependent functions, such as antibody-dependent cellular cytotoxicity (ADCC), antibody-dependent cellular phagocytosis (ADCP), and/or complement-dependent cytotoxicity (CDC) directed against cells expressing a target (e.g., an antigen) to which the tumor-specific binder component(s) may bind. Accordingly, such antibody functions may be used therapeutically to eliminate tumor cells.

FIG. 5 shows a dimer of the transporter associated with antigen processing 1 (TAP1) NBD including two ATP molecules.

FIG. 6 shows an alignment of NBD domains of: wild type TAP1 (SEQ ID NO:9), the ABCA1 gene product from UniProtKB—O95477 (SEQ ID NO:1), the ABCB1 gene product from UniProtKB—P08183 (SEQ ID NO:2), the ABCC1 gene product from UniProtKB—P33527 (SEQ ID NO:3), the ABCD1 gene product from UniProtKB/Swiss-Prot: P33897 (SEQ ID NO:4), the ABCE1 gene product from UniProtKB/Swiss-Prot: P61221 (SEQ ID NO:5), the ABCF1 gene product from UniProtKB—Q8NE71 (SEQ ID NO:6), and the ABCG2 gene product from UniProtKB/Swiss-Prot: P45844 (SEQ ID NO:7). A portion of the Walker A region sequence from aas 46 to 55 and the LSGGQ sequence from aas 152 to 156 of the TAP1 aa sequence are underlined and bolded. The hydrolytic acidic amino acid of the TAP1 NBD shown in FIG. 3 (i.e., the Asp at position 177) and the Asp (D) or Glu (E) residues are shown.

FIG. 7 shows the sequence of human TAP2 from UniProtKB—Q03519 (SEQ ID NO: 11).

Figure 9:
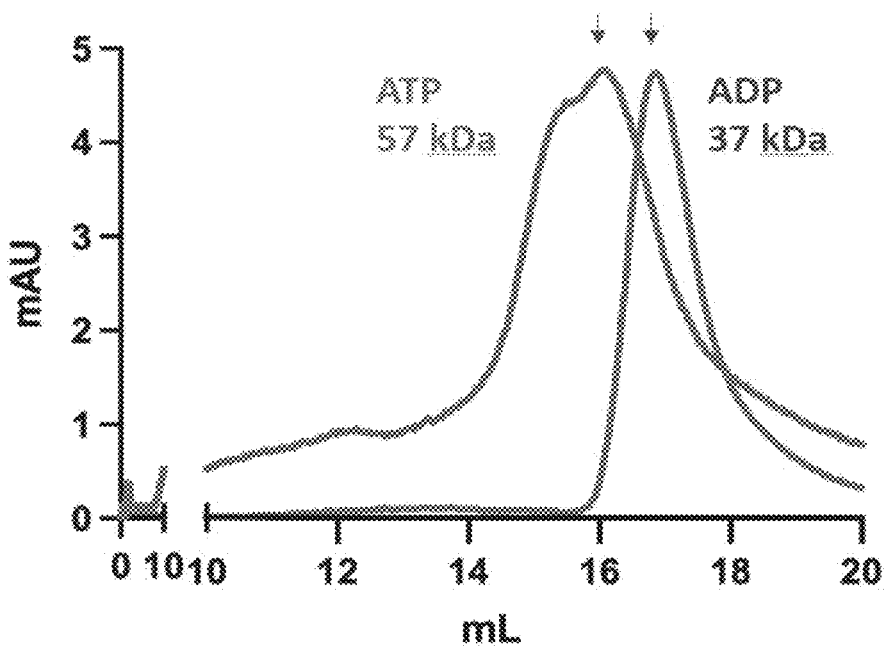

FIG. 9 shows size exclusion chromatograms of a TAP1 NBD variant polypeptide bearing N676G, S677N, Q680R, E682Q, and/or Q683R substitutions and substitutions of cysteines present in the sequence with serines (i) in the presence of 1 mM adenosine diphosphate (ADP) resulting in a monomeric form of the polypeptide (apparent Mw 37 kDa), and (ii) in the presence of 1 mM adenosine triphosphate (ATP) resulting in a dimeric form of the polypeptide (apparent Mw 57 kDa).

Figure 10:
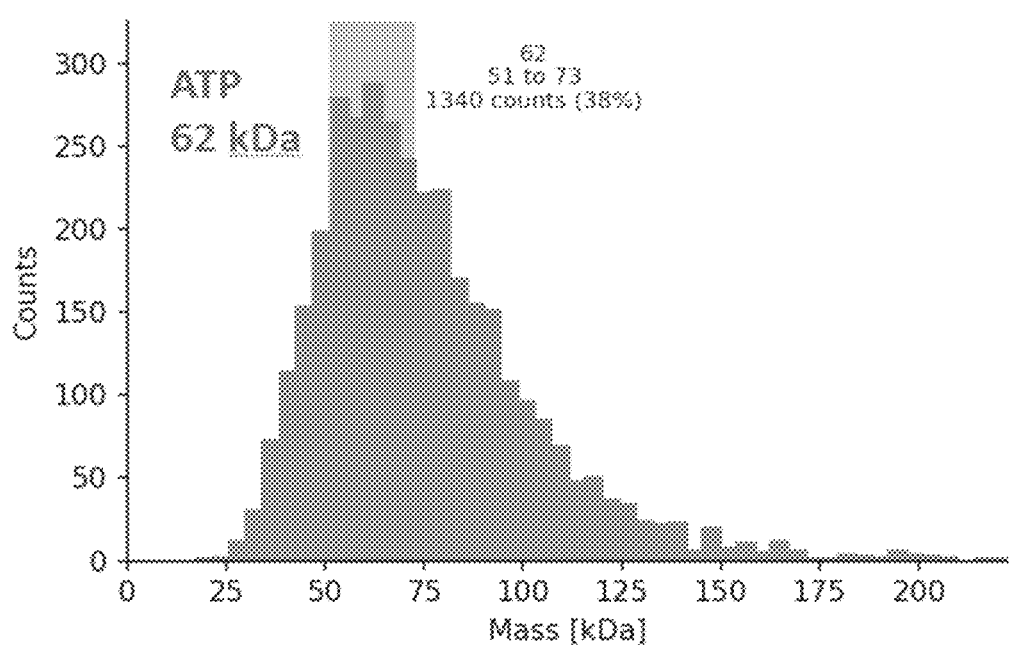

FIG. 10 provides the results of a mass photometry assessment of the same TAP1 NBD variant subject to chromatograph in FIG. 9. The results, obtained in the presence of 1 mM ATP, indicate dimerization of the TAP1 NBD variant.

FIG. 11 provides the results of dynamic light scattering (DLS) size determination for the TAP1 in the presence of (A) ADP or (B) ATP.

Figure 12:
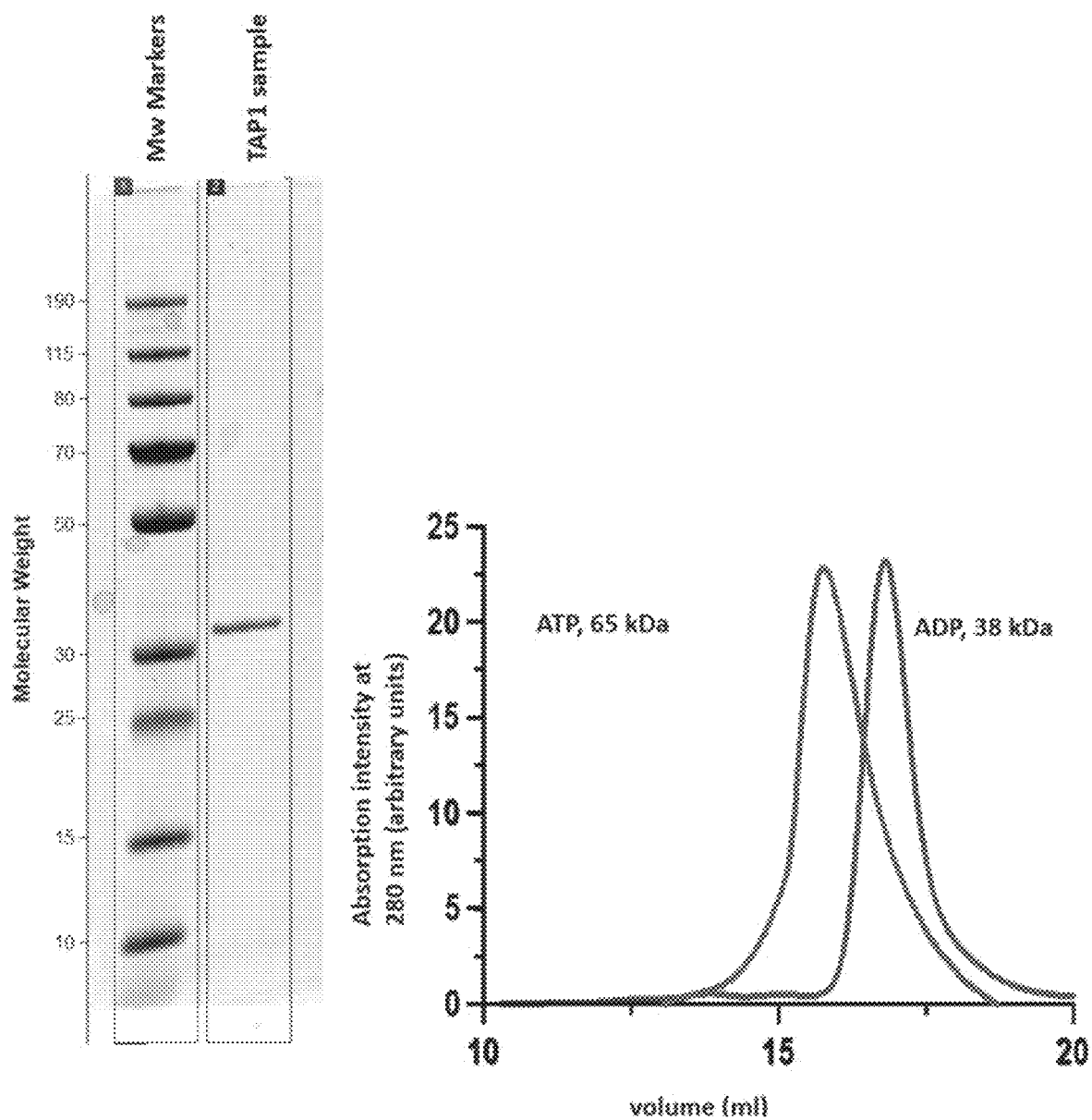

FIG. 12 provides a coomassie blue stained gel of purified TAP1 NBD of SEQ ID NO:87 modified to homodimerize and chromatographic analysis of the purified protein in the presence of ADP and ATP.

Figure 13:
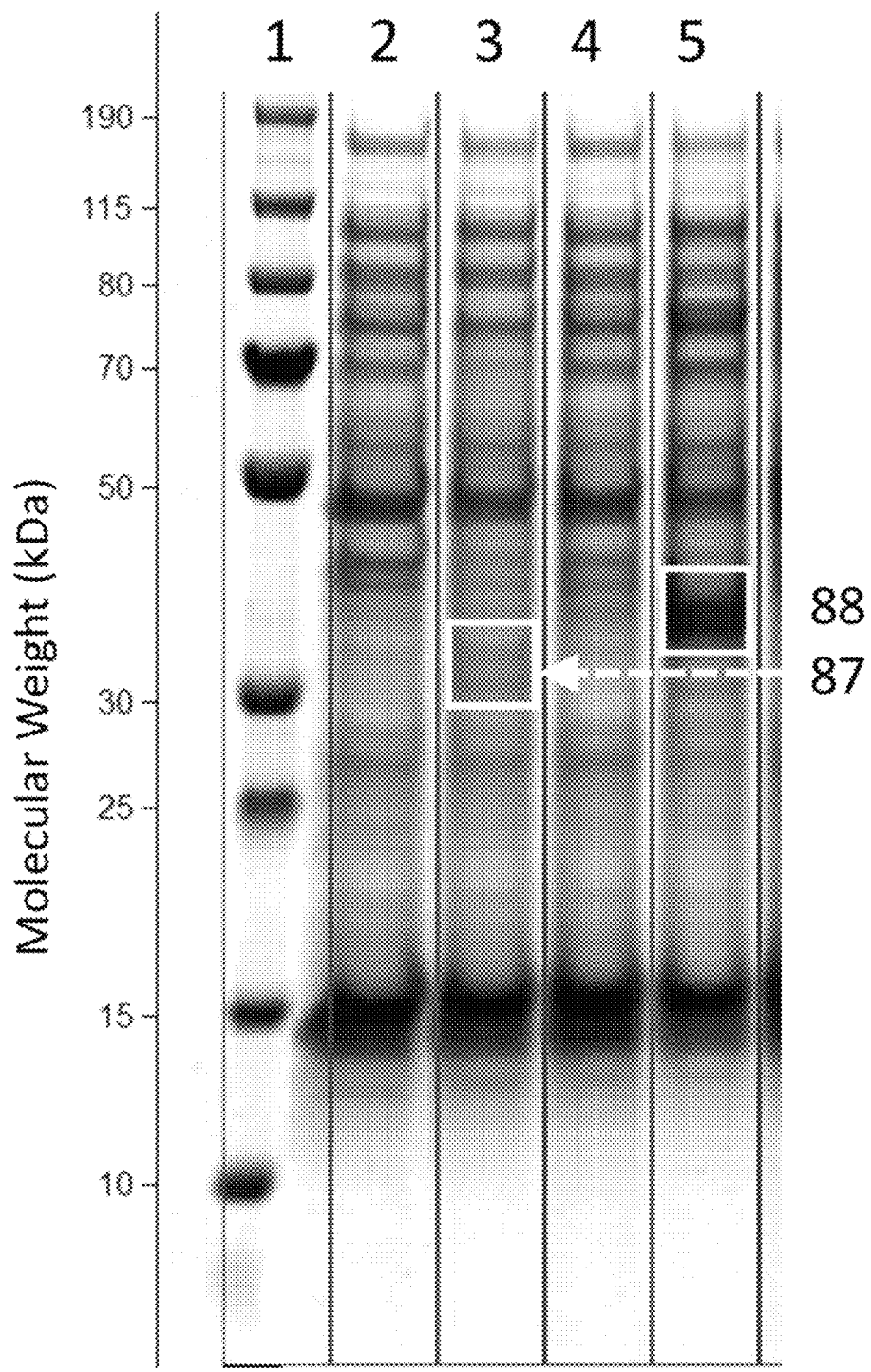
Figure 13:
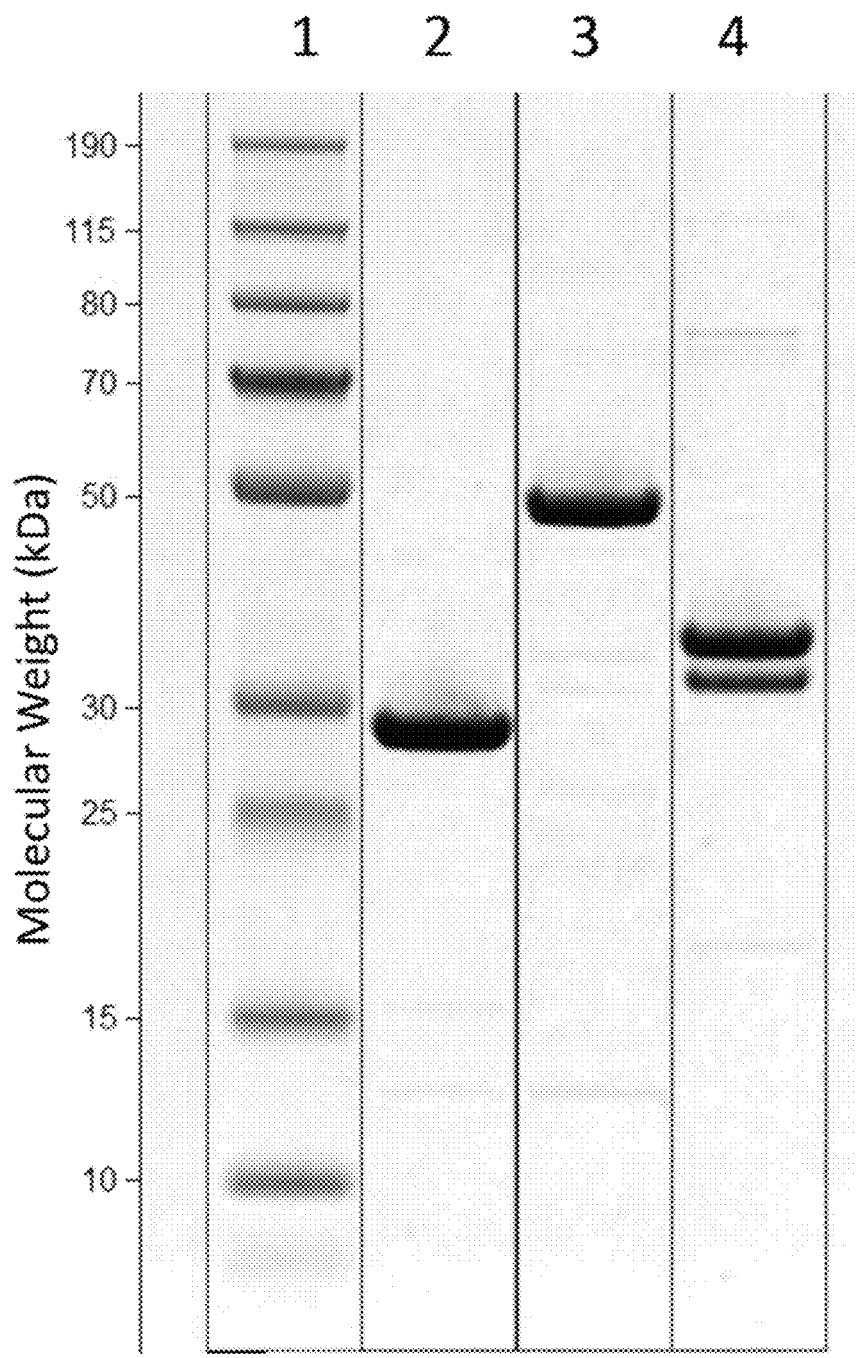

FIG. 13 show SDS-PAGE gels from: (A) the induced expression of the TAP1 NBD polypeptides provided by SEQ ID NO:87 and SEQ ID NO:88; and (B) the purification of the polypeptide of SEQ ID NO:88.

V. DETAILED DESCRIPTION

A. Definitions

As used herein amino acid ("aa" singular or "aas" plural) means the naturally occurring proteogenic amino acids incorporated into polypeptides and proteins in mammalian cell translation. Unless stated otherwise these are: L (Leu, leucine), A (Ala, alanine), G (Gly, glycine), S (Ser, serine), V (Val, valine), F (Phe, phenylalanine), Y (Tyr, tyrosine), H (His, histidine), R (Arg, arginine), N (Asn, asparagine), E (Glu, glutamic acid), D (Asp, asparagine), C (Cys, cysteine), Q (Gln, glutamine), I (Ile, isoleucine), M (Met, methionine), P (Pro, proline), T (Thr, threonine), K (Lys, lysine), and W (Trp, tryptophan). Aa also includes the aas hydroxyproline and selenocysteine, which appear in some proteins found in mammalian cells; however, unless their presence is expressly indicated, they are not understood to be included.

Substitutions of aa at specific locations in a sequence are indicated by the original aa given in single or triple letter code, the numerical position of that aa, and the aa which is substituted into the sequence in single or triple letter code. By way of example an alanine (A) at position 12 of a sequence substituted with a proline (P) would be indicated as A12P using single letter code, or Ala12Pro using triple letter code. Where more than one substitution appears in the same sequence they may be separated by a slash "/". Accordingly the above-mentioned A12P substitution in the same sequence as a V23A and a Q41G substitution may be indicated by the sequence A12P/V23A/Q41G.

The terms "polypeptide" and "protein" are used interchangeably herein, and refer to a polymeric form of aas, which unless stated otherwise are the naturally occurring proteinogenic L-aas that are incorporated biosynthetically into proteins during translation in a mammalian cell.

Alignments to identify corresponding residues of different sequences may be conducted using the US National Center for Biotechnology Information (NCBI) BLAST program (blastp release of BLAST+2.9.0 on the world wide web at blast.ncbi.nlm.nih.gov/Blast.cgi?PAGE=Proteins) or the European Bioinformatics Institute's Clustal Omega program (version 1.2.4 available at www.ebi.ac.uk/Tools/msa/clustalo/) using default parameters. Unless stated otherwise, Clustal Omega is used to identify corresponding residues in different sequences.

The percent sequence identity refers to the percentage of amino acids or nucleotides that are the same between two amino acid or nucleic acid sequences that have been aligned. Unless stated otherwise, the percentage sequence identity is determined using BLAST+release 2.9.0 employing a blastp alignment for polypeptides or a blastn alignment for nucleic acids with default parameters.

The term "substantially" is intended to encompass both "wholly" and "largely but not wholly" unless indicated otherwise. For example, an Ig Fc that "substantially does not induce cell lysis via ADCC or CDC" means an Ig Fc that induces no cell lysis at all or that largely but not wholly induces no cell lysis via ADCC or CDC.

B. Description

The microenvironment within tumors differs in a number of ways from nonmalignant tissues, including differences in any one or more of its pH, ATP content, limited oxygen levels (hypoxia), and tumor protease (e.g., MMPs) levels. Extracellular ATP levels in normal (non-tumor) tissues are typically in the range of 0.01-0.1 micromolar (UM) in normal tissues, whereas the extracellular level of ATP in solid tumors is generally in the range of 50-200 M. The present disclosure describes and provides for the use of the ATP levels found in tumor microenvironments to bring about an immune response to cells in the tumor. More specifically, some constructs described herein may comprise an immune cell activating domain ("AD") (i.e., an activating domain of an immunomodulatory molecule that engages and stimulates an immune cell) and at least one NBD that forms a substantial amount of dimers or other higher order complexes in the presence of ATP at the levels found in the tumor microenvironment (TME). Dimerization or higher order complex formation of the NBD results in a complex presenting two or more immune cell ADs. The use of immune cell ADs that can stimulate immune cells such as NK cells and CD8+ T cells when presented as dimers or higher order complexes, but that do not by themselves stimulate the same immune cells to the same degree when presented singly, permits intratumoral stimulation of an immune response within the TME.

Other constructs described herein may comprise tumor-specific binding domains that bind to TAAs or immune cell engaging domains and at least one NBD that forms a substantial amount of dimers or other higher order complexes in the presence of ATP at the levels found in the tumor microenvironment. Such constructs may optionally comprise an AD. Dimerization or higher order complex formation of the NBD results in dimers or higher order complexes that can recruit and/or stimulate immune cells in the TME. Because dimerization or other higher order complexes of such constructs do not form higher order complexes outside of the TME, they permit intratumoral stimulation of an immune response while limiting immune stimulation outside of the tumor.

Because the ADs, tumor-specific binding domains, and immune cell engagers of the uncomplexed constructs do not effectively stimulate cells such as NK cells and CD8+T effector cells when presented singly, the constructs do not result in systemic immune activation and the associated toxic effects. The constructs described herein do, however, provide immune stimulation localized to the TME where there is sufficient ATP to drive complex formation, and may thus be considered a form of ATP-dependent agonists of immune cell function whose action is limited to that environment. In addition, because the complexed forms of the constructs (e.g., dimers, trimers, etc.) have an increase in size and molecular weight, their diffusion from the TME is reduced further, restricting their action to the TME. Those dimers or higher order complexes that do diffuse out of the TME will dissociate into ineffective individual monomers as the ATP levels in the surrounding non-malignant tissue are too low to support their complexation. Accordingly, the immune stimulation provided by the complexes of the constructs described herein is understood to be reversible and restricted to microenvironments where ATP levels are sufficiently high to induce complexation.

C. The Structure of ATP-Dependent Agonists of Immune Cell Function

1. ATP-Dependent Agonists of Immune Cell Function Comprising NBDs and AD

Figure 2:
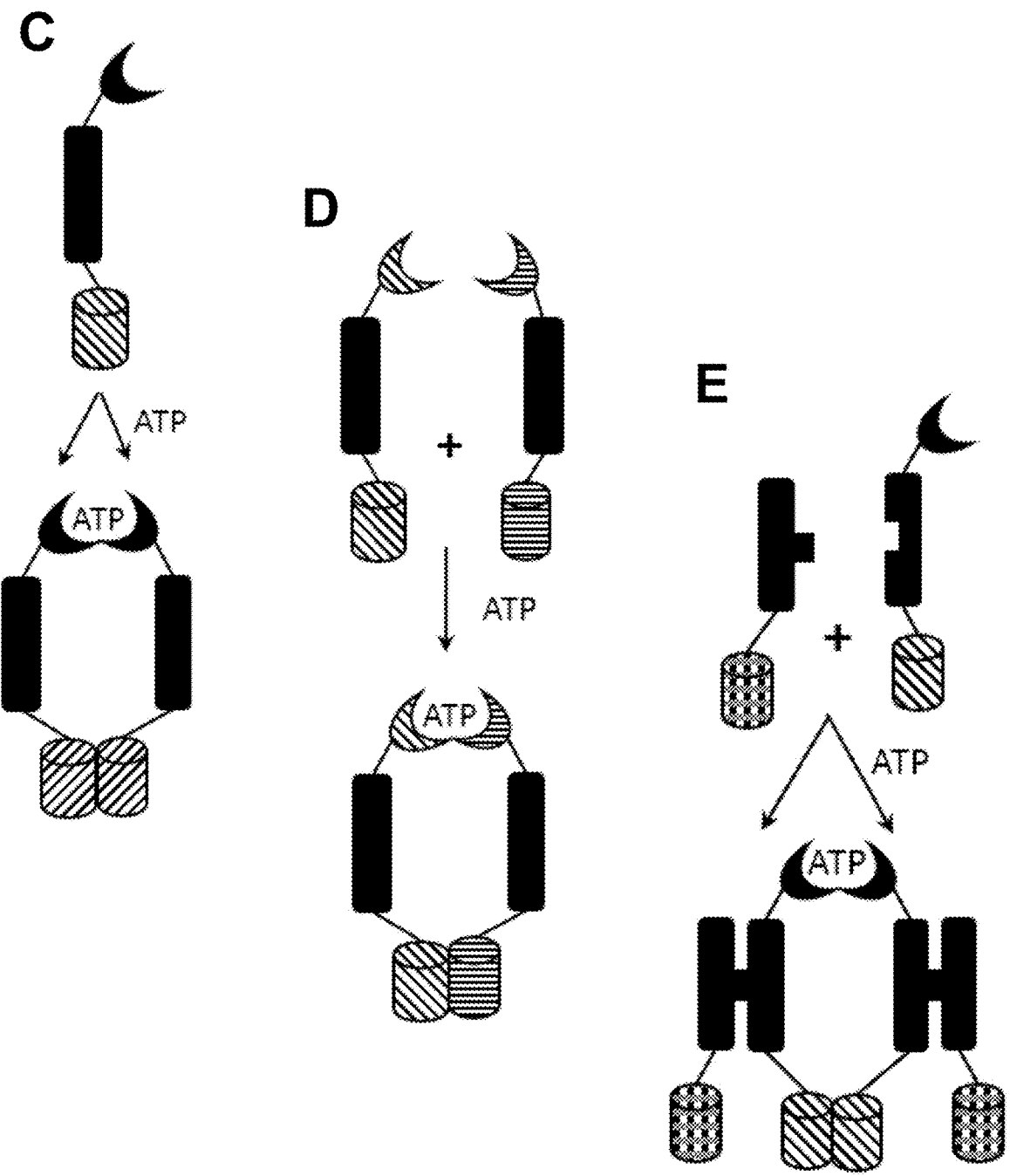

In their simplest form the NBD-containing molecular constructs described herein comprise a NBD and an AD that engages and stimulates an immune cell (e.g., CD8+ T cell, NK cell, etc.). The NBD comprises one or more ATP binding sites that when occupied by ATP result in two or more molecules of the construct forming a duplex or higher order complex (triplex, etc.) due to interactions between the construct's NBDs. Such molecular constructs optionally comprise one or more independently selected scaffold aa sequences and/or one or more independently selected linker sequences. See, e.g., FIG. 1, structure A, and FIG. 2, structures A-D. In some instances, interspecific scaffold sequences that form heterodimers may be incorporated into the constructs such that more than one type of AD may be present in the molecule as exemplified in FIG. 2 by structure E. The use of ADs that, when brought together (e.g., as a homodimer or heterodimer), can stimulate the targeted population of immune cells such as NK cells and/or T cells permits selective stimulation of an intratumoral immune response due to the high levels of ATP in the tumor microenvironment, while at the same time avoiding systemic activation of the targeted immune cells (e.g., NK cells or T cells) and/or an immune response in non-tumor tissues.

The NBD aa sequence, the scaffold aa sequence and the AD may be organized in any order. In a first case, the construct comprises (e.g., from N-terminus to C terminus) the NBD aa sequence, the scaffold aa sequence, and the AD. In a second case, the construct comprises from N-terminus to C-terminus the NBD aa sequence, the AD and the scaffold aa sequence. In a third case, the construct comprises from N-terminus to C-terminus, the AD, the scaffold aa sequence, and the NBD aa sequence. In a fourth case, the construct comprises from N-terminus to C-terminus, the AD, the NBD aa sequence, and the scaffold aa sequence. In a fifth case, the construct comprises from N-terminus to C-terminus, the scaffold aa sequence, the AD, and the NBD aa sequence. Lastly, in a sixth case, the construct comprises from N-terminus to C-terminus, the scaffold aa sequence, the NBD aa sequence, and the AD.

2. NBD-Containing Constructs Comprising Tumor-Specific Binders and/or Immune Cell Engagers The NBD-containing constructs described herein may, in addition to the NBDs, also comprise one or more tumor-specific binding domains and/or an immune cell engaging domain. As discussed in more detail below, tumor-specific binding domains, also referred to as tumor-specific binders, are domains of NBD-containing constructs that have affinity for TAAs expressed on the surface of tumor cells. Immune cell engaging domains, also referred to as immune cell engagers, which are also discussed in more detail below, are domains of NBD-containing constructs that have affinity for cell surface molecules (e.g., antigens) of immune cells. Unless stated otherwise, immune cell engagers, which may be, for example, antibody fragments, are monovalent to avoid the potential for off-target stimulation (e.g., systemic stimulation) of the immune cells to which they bind. NBD-containing constructs comprising one or more tumor-specific binders and/or an immune cell engager may also comprise one or more ADs. See FIG. 3, structures D, E, H, and I.

Tumor-specific binders and immune cell engagers may be incorporated into NBD-containing constructs that form heterodimers or other higher order complexes (e.g., trimers) in the presence of ATP at the concentration found in, for example, the TME environment. Heterodimer formation may be driven by the incorporation of a first ($1^{st}$) heterodimerizing NBD in the first member of the pair of constructs and a second ($2^{nd}$) heterodimerizing NBD in the second member of the pair of constructs. The $1^{st}$ and $2^{nd}$ heterodimerizing pairs of NBDs act as cognate binding partners. In order to exemplify the type of such NBD-containing construct pairs encompassed by the present disclosure, a series of non-limiting examples of such NBD-containing construct pairs is set forth in FIG. 3. In vivo the dimerized constructs direct immune cells bound by the immune cell engager to interact with target tumor cells recognized by the tumor-specific binder, bringing about an immune response to the target tumor cells. Such constructs permit the targeting of tumor cells in the TME as they require elevated ATP for complex formation, and thereby limit off-target binding and stimulation of immune cells. The paired constructs comprising tumor-specific binders and immune cell engagers may be augmented by the incorporation of one or more ADs that may be the same or different, and may require dimerization brought about by interaction of the first and second NBD-containing constructs to stimulate the target immune cells.

Figure 3:
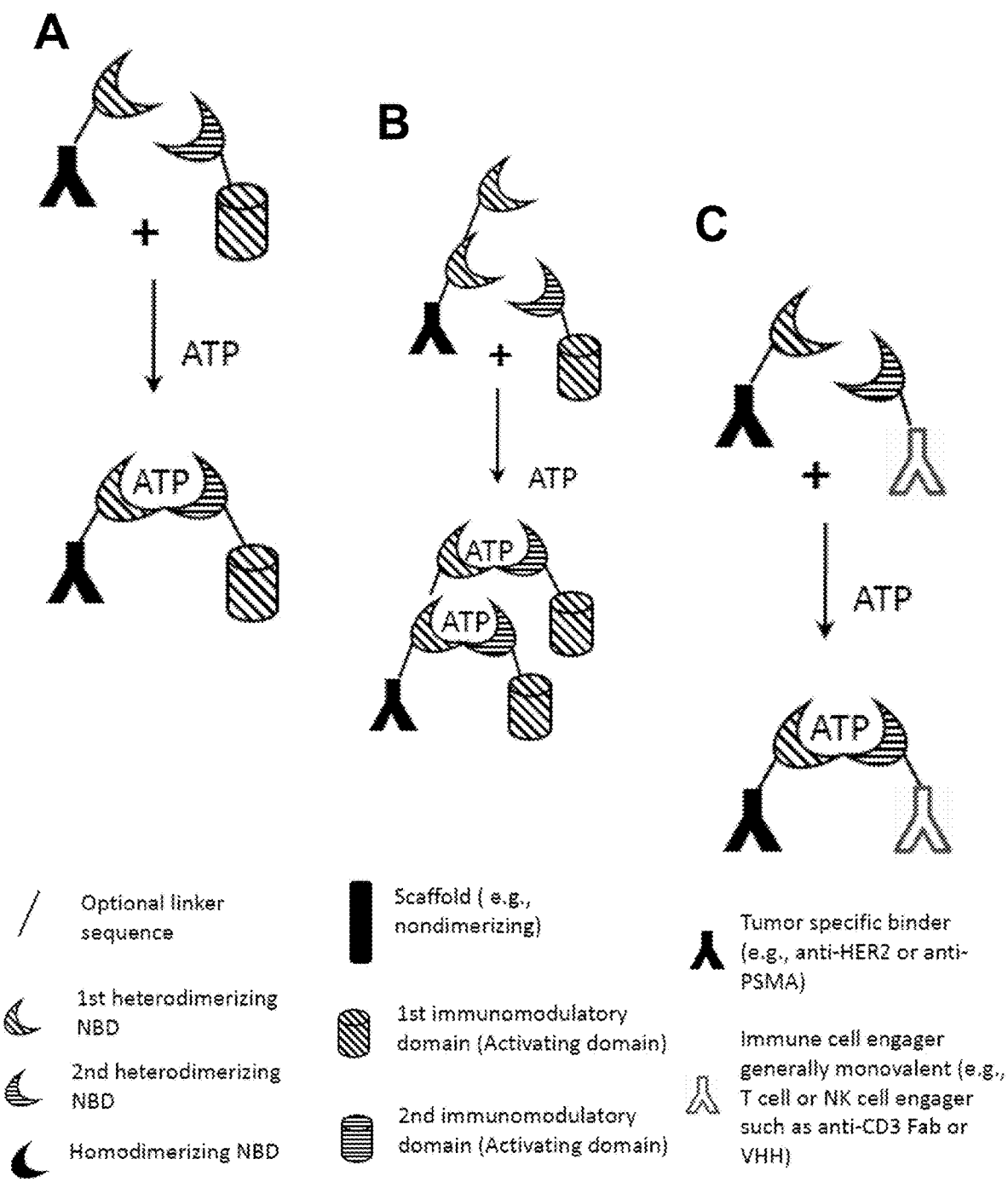
Figure 3:
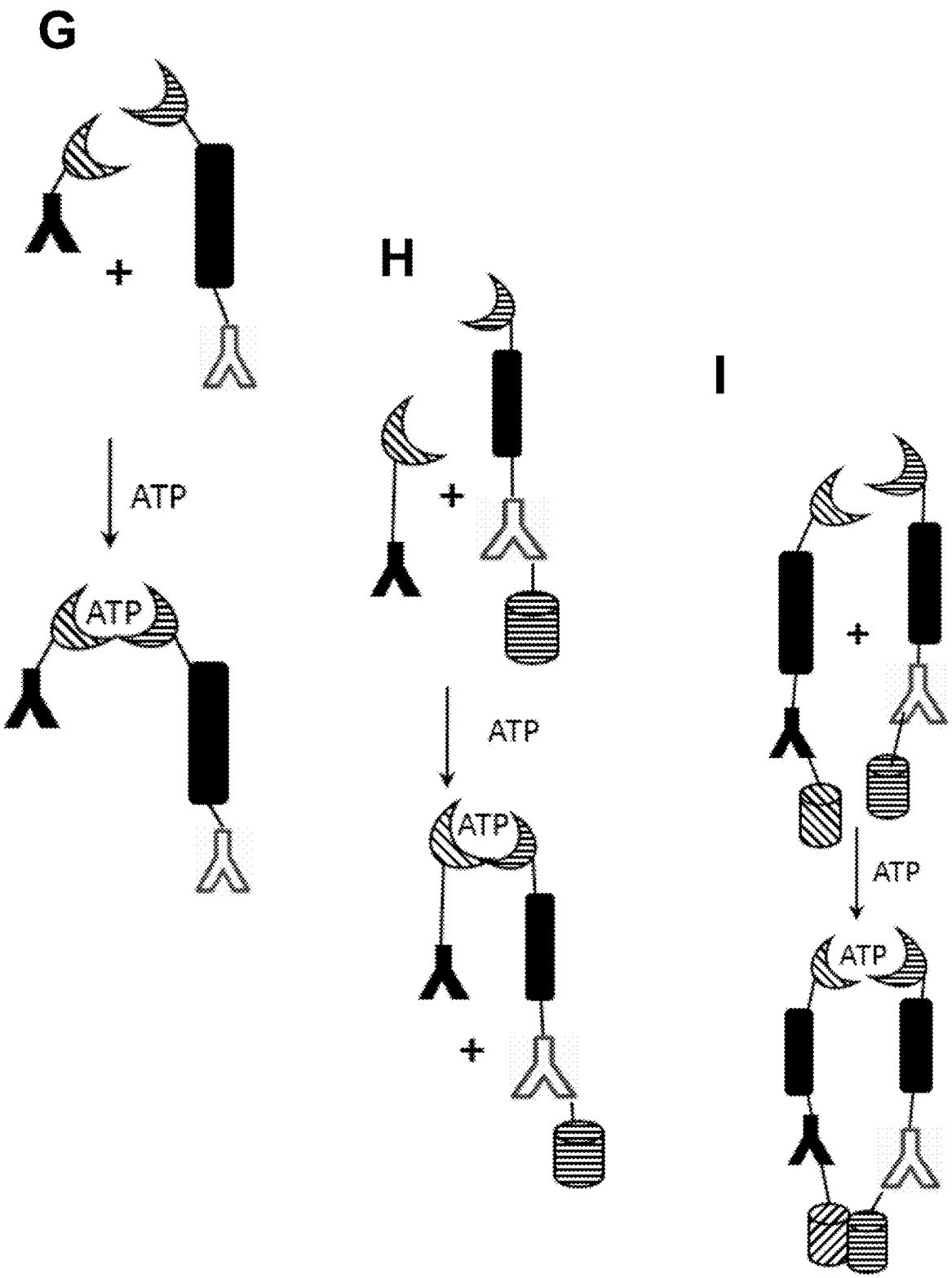
Figure 3:
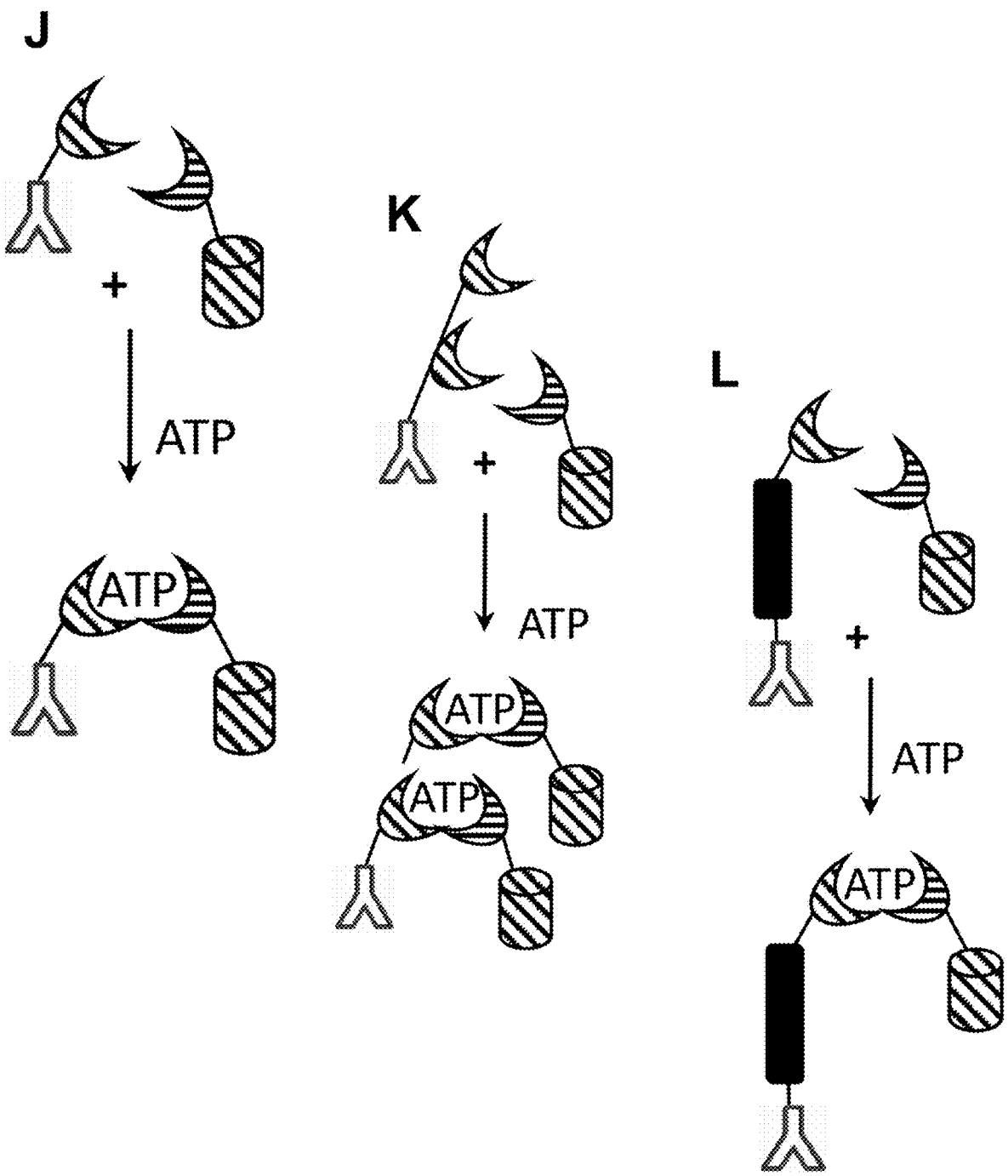
Figure 3:
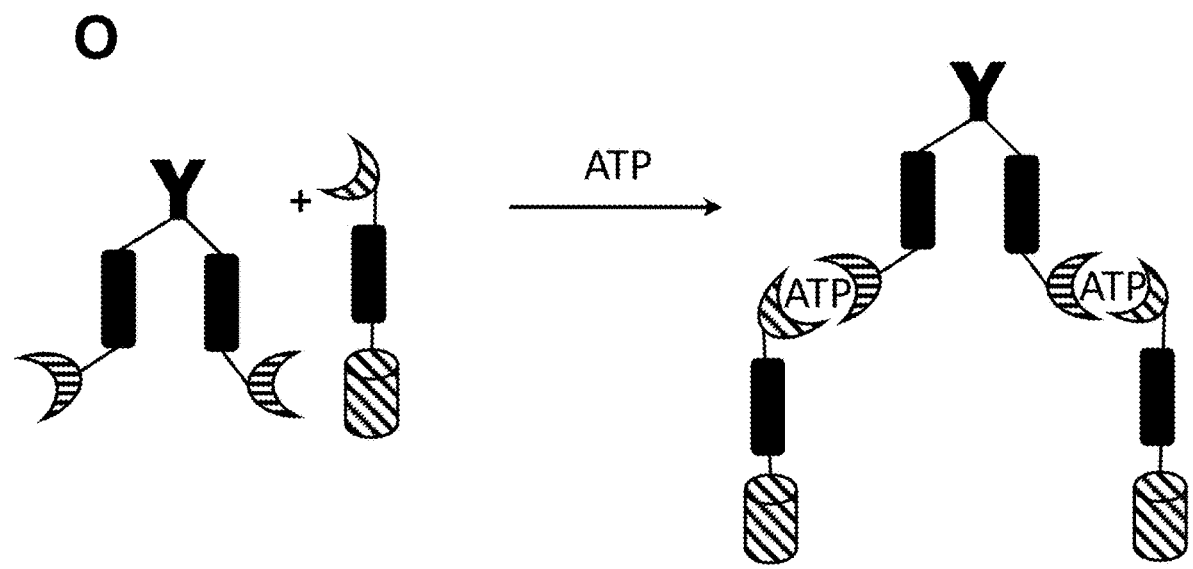

Entries A and B of FIG. 3 each provide a pair of constructs in which the first NBD-containing construct comprises (e.g., from N-terminus to C-terminus or from C-terminus to N-terminus) one or more $1^{st}$ heterodimerizing NBDs linked to a tumor-specific binder and the second NBD-containing construct comprises (e.g., from N-terminus to C terminus) a cognate $2^{nd}$ heterodimerizing NBD and an AD. The elements of the constructs are joined by optional linker sequences that are independently selected. Such constructs permit the targeting of ADs to tumor cells in the TME as they require elevated ATP to heterodimerize, and thereby limit off-target binding and avoid systemic stimulation of immune cells by the AD. In addition, the ADs of the constructs set forth at B may be the same or different and may require dimerization to function on the target immune cell. Although not shown in FIG. 3 at A or B, either or both of the heterodimerizing constructs in A or B may also comprise a scaffold aa sequence (see, e.g., entry E in FIG. 3).

An exemplary pair of constructs that illustrates heterodimerization of the type shown in entries A or B of FIG. 3 may comprise, for example: (i) a first NBD-containing construct comprising one or more TAP1 NBDs linked to a tumor-specific binder that has affinity for a TAA (e.g., NY ESO-1, mesothelin, CEA, PSMA, or a MAGE such as MAGE-A1, MAGE-A4, MAGE-A9, or MAGE-A11); and (ii) a second NBD-containing construct comprising a TAP2 NBD that acts as the cognate binding partner of the TAP1 NBD in the presence of ATP and an IL-2 sequence. When exposed to ATP at the levels present in the TME, such constructs heterodimerize and can act to stimulate T cells present in the TME.

Entries C and D of FIG. 3 each provide a heterodimerizing pair of constructs in which the first NBD-containing construct comprises (e.g., from N-terminus to C-terminus) one or more 1$^{st}$ heterodimerizing NBDs linked to a tumor-specific binder and the second NBD-containing construct comprises (e.g., from N-terminus to C terminus) a cognate 2$^{nd}$ heterodimerizing NBD and an immune cell engager. The elements of the constructs are joined by optional linker sequences that are independently selected. Either or both of the first and second constructs of the heterodimerizing pair may comprise a scaffold sequence (see, e.g., FIG. 3 at F to I). Constructs comprising a tumor-specific binder and/or an immune cell engager may further comprise an AD as in entries D, E, H, and I. Where an AD is present in a construct that also comprises an immune cell engager, the AD may be selected from those that require presentation to the T-cell as a dimer or higher order complex (e.g., TNF family members such as 4-1BBL) for immune cell stimulation to prevent off-target stimulation.

A pair of constructs that exemplify entry C of FIG. 3 comprises, for example: (i) a first NBD-containing construct comprising (a) a TAP1 NBD linked to (b) a tumor-specific binder; and (ii) a second NBD-containing construct comprising (a) a TAP2 NBD that acts as the cognate binding partner of the TAP1 NBD in the presence of ATP and (b) a monovalent T-cell engager (e.g., an anti-CD3 antibody fragment or single chain antibody construct such as a nanobody or scFv). The tumor specific binder may be an antibody, antibody fragment, or single chain antibody construct such as a scFv or nanobody) that has affinity for a TAA expressed on a tumor cell surface (e.g., NY ESO-1, mesothelin, CEA, PSMA, or a MAGE such as MAGE-A1, -A4, -A9, or -A11).

Entries A to I of FIG. 3 appear as combinations of two molecular constructs. Because the first construct comprising the tumor-specific binder in those combinations is separate from the second construct comprising an AD and/or an immune cell engager, a population (mixture) comprising more than one type of first or second construct may be formed. For example, a mixture of first and second constructs depicted in any one of entries A to I of FIG. 3 may be formed wherein the mixture comprises two or more first constructs each having tumor-specific binders targeting different TAAs. A mixture of first and second constructs depicted in any one of entries A or B of FIG. 3 may be formed wherein the mixture comprises two or more second constructs each having one or more ADs directed to different immune cell receptors. Similarly, a mixture of first and second constructs depicted in any one of entries C to I of FIG. 3 may be formed wherein the mixture comprises two or more second constructs each having different immune cell engagers directed to different immune cell surface antigens. In addition to populations where only one of the immune cell engager, tumor-specific binder, or AD is varied, the mixtures of first and second constructs may comprise two or more first and two or more second constructs that vary in two or more elements selected from the immune cell engager, tumor-specific binder, and AD.

Entries J through M of FIG. 3 each provide a pair of constructs in which the first NBD-containing construct comprises (e.g., from N-terminus to C terminus) one or more 1$^{st}$ heterodimerizing NBDs linked to an immune cell engager and the second NBD-containing construct comprises (e.g., from N-terminus to C terminus) a cognate 2$^{nd}$ heterodimerizing NBD and an AD. The elements of the constructs are joined by optional linker sequences that are independently selected. Such constructs permit the activation of immune cells in the TME while avoiding any substantial activation outside of the TME as they require elevated ATP to heterodimerize, and thereby limit off-target binding and avoid systemic stimulation of immune cells by the AD. In addition, the ADs of the constructs set forth in either K or M may be the same or different and may require dimerization to function on the target immune cell.

Exemplary pairs of constructs that illustrate heterodimerizing constructs of the type found in FIG. 3 at J and K comprise, for example: (i) a first NBD-containing construct comprising one or more TAP1 NBDs linked to an immune cell engager (e.g., an antibody, antibody fragment, or single chain antibody construct such as a VHH or nanobody) that has affinity for CD28 expressed on a T cell surface; and (ii) a second NBD-containing construct comprising a TAP2 NBD that acts as the cognate binding partner of the TAP1 NBD in the presence of ATP and an IL-2 sequence. Such constructs when complexed into a heterodimer by ATP at the levels present in the TME can act to stimulate T cells present in that environment.

Compositions comprising a mixture of constructs find use in therapeutic applications where the use of more than one tumor-specific binder directed against different TAAs can avoid having the tumors escape monotherapy with a single construct. Similarly, the use of more than one immune cell engager and/or AD can recruit more than one type of immune cell and provide a more vigorous immune response to the tumor cells, thereby effectuating a more robust immune response to the tumor than would occur using monotherapy with a single construct.

3. NBD-Containing Constructs Comprising Two or More NBDs and the Formation of Complexes of NBD-Containing Molecular Constructs The NBD-containing constructs described herein may comprise two or more NBDs that permit the constructs to effectively polymerize into complexes in the presence of ATP. The two or more NBDs may, for example, be arranged as a tandem pair. When placed in tandem the NBDs are adjacent to each other in the construct and are not separated by any element of the constructs other than an intervening linker aa sequence (e.g., no AD (s), scaffold, tumor-specific binding domain(s), or immune cell engaging domain(s) are present between the tandem NBDs). Additional NBDs may be located in the construct so that they are not placed in tandem. For example, NBD-containing constructs comprising two or more NBDs may be formed by replacing the NBD of the first through sixth cases described above in section C.1. (ATP-dependent agonists of immune cell function comprising NBDs and AD) with a pair of NBDs in tandem. NBD-containing constructs comprising two or more NBDs (e.g., in tandem) may also be formed from constructs comprising an immune cell engager or tumor-specific binder.

Complexes of NBD-containing molecular constructs comprising at least two NBDs can be formed by placing the constructs in an environment, such as a TME, where ATP levels are sufficiently high for ATP to occupy the binding sites. Such complexes are exemplified in FIG. 3 at N and O, and in FIG. 4A. Where, as in FIG. 4A more than one NBD aa sequence is incorporated into constructs of the present disclosure, the constructs may, in effect, reversibly polymerize in the presence of ATP to produce complexes. The complexes formed in the presence of ATP may be dimers, trimers, tetramers or even higher order structures. See, e.g., FIG. 4A. Incorporating more than one NBD in the constructs may permit maximization of potency and efficacy, and may affect other properties. For example, complexes that become polyvalent for an element expressed on the surface of target cells (e.g., for a tumor-specific engager or AD) may display an increased effective affinity for the target cells, larger complexes may remain in the TME longer thereby effectively extending the in vivo half-life of the complex, etc.

Complexes may comprise at least two NBDs arranged in tandem, with at most a linker aa sequence (e.g., a rigid linker) separating the NBD aa sequences (see FIG. 4A, structures A, B, and E) and an AD, immune cell engager and/or tumor-specific binder. Alternatively, the NBDs may be separately attached to the tumor-specific binder or immune cell engager (see FIG. 4A, structures C and D). NBD-containing constructs used to form complexes may comprise homodimerizing or heterodimerizing NBDs. Although not shown in FIG. 4A, homodimerizing NBDs in the same construct molecule may be prevented from self-associating by constructing the molecule such that a productive ATP binding interface between the domains cannot be formed. This may be accomplished by, for example, limiting the distance between the NBDs or by the use of a rigid peptide linker between the NBDs.

Figure 4A:
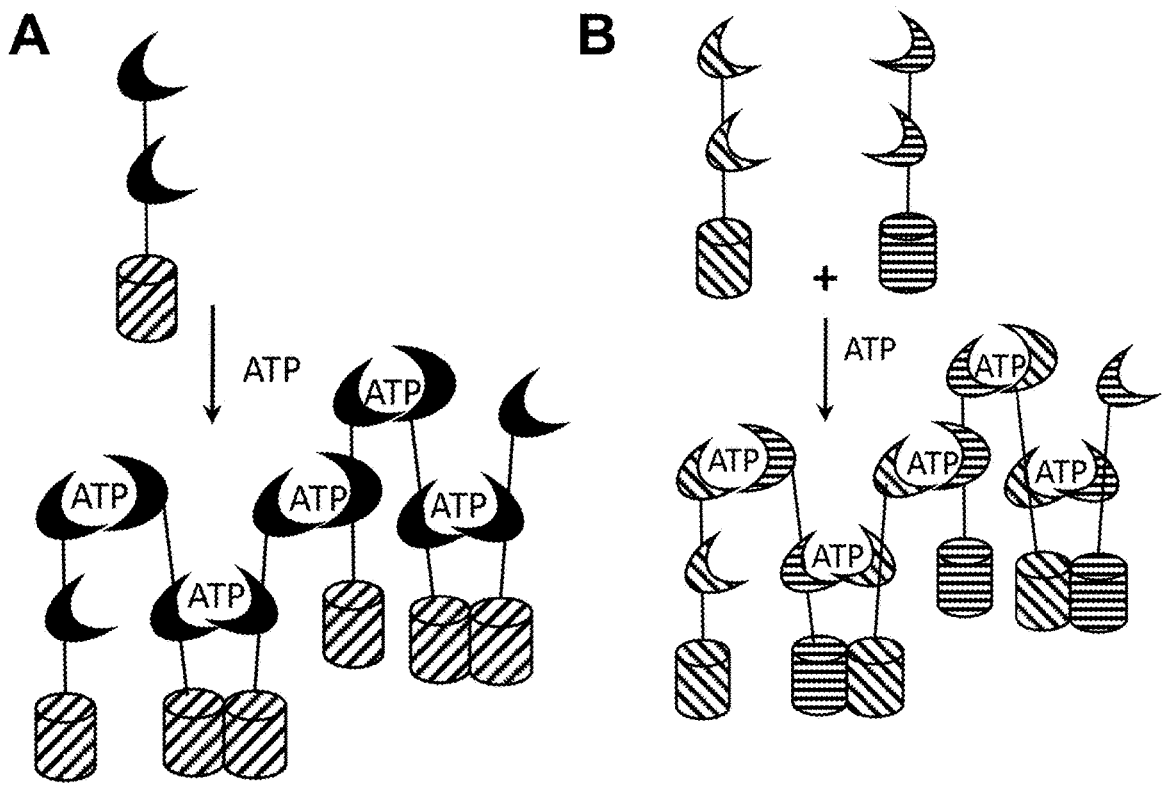

NBD-containing constructs comprising at least two NBDs and an AD are exemplified in FIG. 4A by structures A and B. Structure A employs a NBD that homodimerizes in the presence of ATP and may form dimers and/or a larger construct as shown in FIG. 4A, structure A. In contrast, structure B comprises a structure that forms a heterodimer or polymer in the presence of ATP. When exposed to ATP at the levels present in the TME the constructs may form large complexes presenting ADs (e.g., as AD homodimers or heterodimers). Complexes of such NBD-containing constructs may stimulate target immune cells, such as NK cells and/or T cells, in the TME. The ADs present in the complex may be the same (e.g., FIG. 4A, structure A) or different (e.g., FIG. 4A, structure B). For example the aa sequence of the $1^{st}$ AD and the $2^{nd}$ AD present in a complex may be identical and lead to activation of an immune cell response when presented in a dimer or higher order complex. Alternatively, the $1^{st}$ AD and the $2^{nd}$ AD present in a complex may be from different molecules (e.g., different interleukins) that when presented together cause immune cell activation. It is also possible that the aa sequence of the $1^{st}$ AD and the $2^{nd}$ AD present in a complex are different (nonidentical), and when combined form an active fragment of a dimeric immunomodulator such as IL-12, IL-23, or IL-27, each of which comprises two subunits (a and B polypeptide chains). NBD-containing constructs each comprising a single NBD may be assembled into a complex comprise two different (non-identical) ADs in the presence of ATP. Alternatively, active AD comprised of two subunits can assemble into an active AD using constructs each comprising a single NBD the presence of ATP (see, e.g., FIG. 2, structures A and B).

In addition to the NBD-containing constructs described above, this disclosure provides for NBD-containing constructs that comprise at least two NBDs and a tumor-specific binding aa sequence (tumor-specific binder) exemplified by FIG. 4A, structure C, and/or an immune cell binding aa sequence (immune cell engager), exemplified by FIG. 4A, structure D. Such molecular constructs optionally comprise one or more independently selected scaffold aa sequences and/or one or more independently selected linker sequences. Tumor-specific binders include, but are not limited to, antibodies that bind to TAAs (e.g., HER-2, MAGE-2, MAGE-4, NY-ESO, and the like). Immune cell engagers include molecules including, but not limited to, antibodies that bind to immune cell surface antigens (e.g., CD3, CD8, or CD4 on αβ T cells, TRGV9 on δγT cells, CD16 on NK cells, etc.). Unless stated otherwise, immune cell engagers are monovalent to avoid stimulation of immune cells outside of the TME and have sequences that can lead to antibody-dependent cell-mediated cytotoxicity (ADCC) or complement-dependent cytotoxicity (CDC) modified to substantially limit or prevent such responses.

Once present in the TME where ATP levels permit the NBD domains to form higher order complexes (e.g., dimers), constructs that comprise at least two NBDs and a tumor-specific binder and/or an immune cell engager form large complexes that can lead to immune stimulation. Constructs comprising at least two NBDs, a scaffold comprising an IgFc, and a tumor-specific binder can form a complex in the TME (see, e.g., FIG. 4A, structure C) that can, for example, lead to ADCC or CDC. Constructs comprising at least two NBDs and an immune cell engager can form a complex in the TME (see, e.g., FIG. 4A, structure D) that can, for example, lead to stimulation of the targeted immune cells due to crosslinking of the target antigen (e.g., CD3 on CD8+ T cells or CD16 on NK cells) on their surface.

Combining a NBD-containing construct comprising at least two NBDs and a tumor-specific binder (e.g., FIG. 4A, structure C) and a NBD-containing construct comprising at least two NBDs and an immune cell engager (e.g., FIG. 4A, structure D) may result in complexes that comprise both tumor-specific binders and immune cell engagers. The use of $1^{st}$ heterodimerizing NBDs with the tumor-specific binder and $2^{nd}$ heterodimerizing NBDs with the immune cell engager can ensure the complex formed in the presence of ATP contains both the binder and engager and can stimulate immune cell responses to the target tumor cell. This is exemplified with mixtures of constructs comprising at least two NBDs and a tumor-specific binder and constructs that comprise at least two NBDs and an immune cell engager, forming large complexes in the TME (see, e.g., the structures in FIG. 4A at E and F where the NBDs are shown in tandem). Complexes resulting from such structures in the presence of sufficient ATP can bind immune cells to tumor targets via the tumor-specific binder, and at the same time bring about activation of the immune cell by crosslinking of the receptors on the cell surface via the monomeric immune cell engager that is now complexed.

The tumor-specific binder and/or immune cell engager aa sequences present in each construct used to form a complex need not be the same. Accordingly, the complexes of FIG. 3, structures A to I, and FIG. 4A, structures C to I, may have more than one tumor-specific binder directed to different TAAs (e.g., two or more tumor-specific binders), and, when present, more than one immune cell engager. Using two or more different tumor-specific binders directed against different TAAs in a single complex not only permits the complex formed from constructs comprising two or more NBDs to be active against tumors expressing different tumor antigenic targets, but also may limit tumor escape from therapy by loss of tumor antigen expression. Using different immune cell engagers in a single complex permits the stimulation of an immune response from more than one type of immune cell (e.g., both CD8+ T cells and NK cells). It is also possible to incorporate ADs into complexes that form in the TME, including complexes containing a construct that includes a tumor-specific binder. This can be done by, for example, combining one or more constructs that comprise an AD and a NBD (e.g., two or more NBDs) in the complex such as is exemplified in FIG. 4A at H, or by combining one or more constructs that comprise an AD, a NBD (e.g., two or more NBDs), and a tumor-specific binder in the complex such as is exemplified in FIG. 4A at I.

Because the tumor-specific binders, immune cell engagers, and ADs are provided by different constructs that enter into the complex formed in the TME, the composition of the complex can be controlled by mixing different constructs (e.g., prior to or during administration to a patient). Thus, a single construct may find use in different therapeutic combinations.

D. Elements of NBD-Containing Constructs

1. NBDs and Interactions with ATP

NBDs for incorporation into the constructs described herein may be selected based on several criteria. Where the constructs are intended for human therapeutic use, the NBDs are preferentially derived from human ATP binding proteins to limit their immunogenicity and are preferably able to undergo solution phase dimerization or higher complex formation when exposed to sufficient ATP. Where non-human proteins that are immunogenic are employed, immunogenic portions may be humanized by altering the immunogenic regions to more closely or completely match their human homologs. The solution phase formation of dimers or higher order complexes used in the constructs described herein occurs at ATP concentrations found in the target TME, but not in normal tissues. Accordingly, a NBD for use in the constructs provided herein may have, for example, a dissociation constant for ATP from about an order of magnitude above (10 times above) the upper level found in the extracellular space of normal tissues (i.e., about 1 µM or higher) up to about the level of ATP found in the TME. In some cases the affinity of a NBD will be from about 1 µM to about 200 µM. For example, the ATP affinity of a NBD may be in a range from about 1 µM to about 5 µM, or from about 5 µM to about 25 µM. The ATP affinity of a NBD may be in a range from about 25 µM to about 50 M. In other examples, the affinity of a NBD may be in a range from about 50 µM to about 100 µM or from about 100 µM to about 200 µM.

NBDs of some proteins form homodimers in the presence of sufficient levels of ATP, while others form heterodimers in the presence of sufficient levels of ATP. Both homodimerizing NBDs and heterodimerizing NBDs may be employed in various aspects of the polypeptide constructs described herein. Where it is desirable to have the NBDs form homodimers in solution when sufficient levels of ATP are present, aa residues at the interface between the dimers may be modified to either remove or substitute aa residues that interfere with interface formation between two NBD molecules. Alternatively, it is possible to substitute aas not contributing to the interactions between the two NBD molecules with aas that will contribute to interactions resulting in homodimer formation.

a) ATP-Binding Cassettes as NBDs

Figure 5:
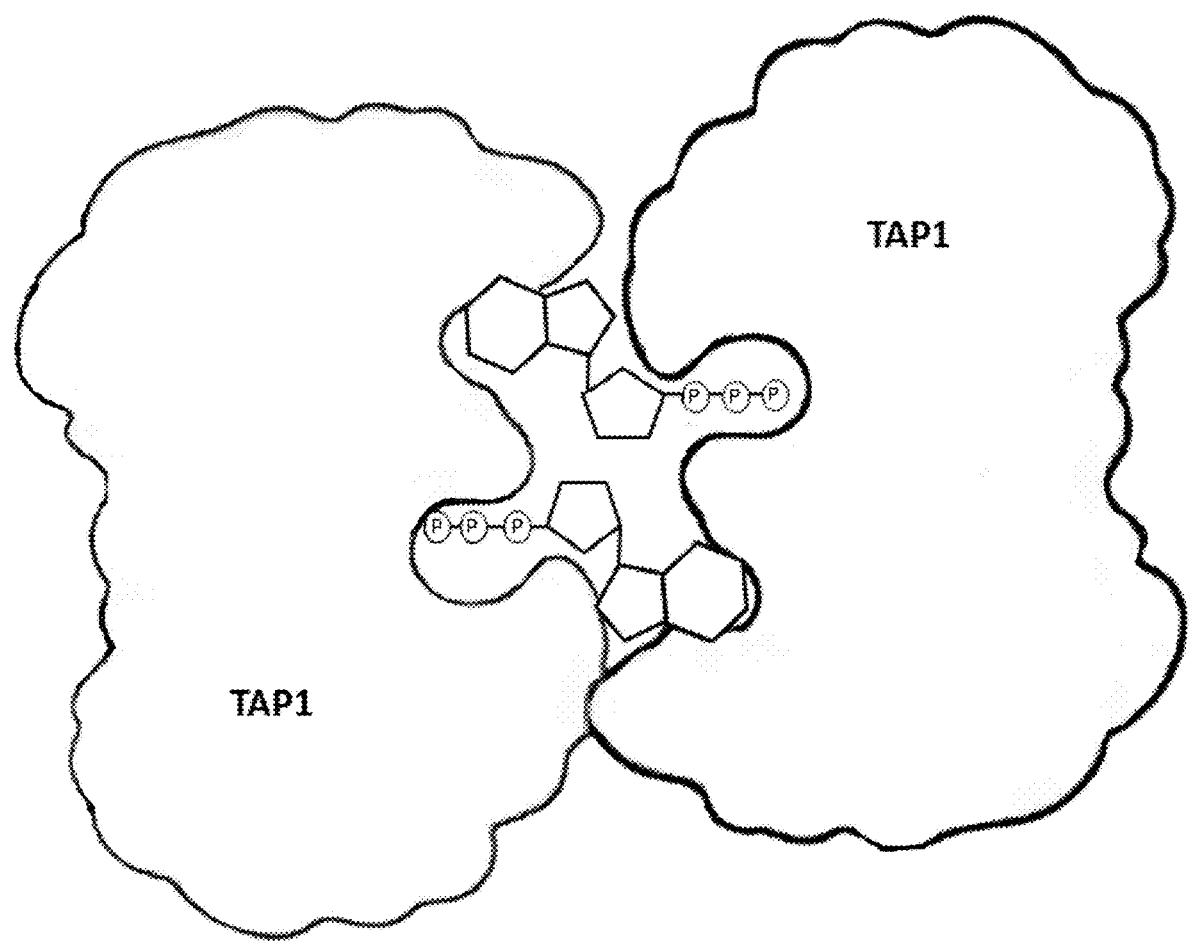

A number of proteins comprise NBDs that are suitable for use as NBDs of the constructs described herein. Among those proteins, ATP-binding cassette (ABC) transporters represent suitable candidates in part because they are an abundant transporter family that is highly conserved and as such unlikely to be immunogenic. ABC transporters are a large superfamily of membrane proteins with diverse functions that utilize the energy from ATP hydrolysis to facilitate transport of substrates either into or out of the cytoplasm. See, e.g., Locher, *Philos Trans R Soc Lond B Biol Sci.,* 364(1514): 239-245 (2009), and reference cited therein. The human genome codes for 48 or 49 distinct ABC transporters. Id. The ABC transporters are divided into seven distinct family members, ABC1, MDR/TAP, MRP, ALD, OABP, GCN20, and White. A representative member of each family including TAP1 are aligned in FIG. 6. The NBD of the ATP-binding cassette family is conserved and comprises two sub-domains. Id. The first resembles RecA protein and contains P-loops (Walker-A motifs). The second subdomain, referred to as the "helical sub-domain," comprises an LSGGQ motif. Id. The NBDs of the transporters assemble as dimers in head-to-tail orientation forming two ATP binding and hydrolysis sites sandwiched at their interface (see FIG. 5). In that orientation the LSGGQ motif in each of the two domains is adjacent to the opposing Walker-A sequence at the ATP-sandwich interface. Such interfaces are described, for example, in Loo et al., (2002) *J Biol Chem.,* 277(44): 41303-41306, and Smith et al., (2002) Mol Cell., 10(1): 139-149, at FIG. 3A. When a nucleotide (ATP) is not present in the binding sites there is a gap at the domain interface; however, when ATP is bound the NBD dimerizes and hydrolyzes ATP, and can then dissociate (see, e.g., Locher 2009 supra). Stabilized dimers can be formed by including aa substitutions that make the NBD domain sequences ATP hydrolysis deficient or substantially ATP hydrolysis deficient (e.g., by reducing the ATP hydrolysis rate by one or more orders of magnitude (see, e.g., Vakkasoglu et al., (2107) *PLOS ONE,* 12(5): e0178238, available at doi.org/10.1371/journal.pone.0178238). For example, the hydrolytic Asp or Glu residue found in NBD proteins may be substituted by an Asn or Gln residue (see, e.g., FIG. 3).

Where it is desirable to have the NBDs of ABC proteins form homodimers in solution when sufficient ATP is present, residues at the interface between the dimers may be modified to either remove or substitute aa residues that interfere with interface formation, or to substitute aas not contributing to the interface interactions with aas that can contribute to the interactions. By way of example, it is known that the NBD of rat TAP1 homodimerizes in solution and can be used as a model for the formation of the ATP-sandwich interface to bring about solution phase homodimerization in the presence of ATP (see, e.g., Vakkasoglu et al., (2107) *PLOS ONE,* 12(5): e0178238. https://doi.org/10.1371/journal.pone.0178238). Alignment of a NBD aa sequence with a sequence known to undergo homodimerization, e.g., the rat TAP1 NBD, can be used to guide alterations in a target sequence. Alignments may be carried out using the US National Center for Biotechnology Information (NCBI) BLAST program (blastp release of BLAST+2.9.0 on the world wide web at blast.ncbi.nlm.nih.gov/Blast.cgi?PAGE=Proteins) or the European Bioinformatics Institute's Clustal Omega program (version 1.2.4 available at www.ebi.ac.uk/Tools/msa/clustalo/) using default parameters. Unless stated otherwise Clustal Omega is employed.

A NBD aa sequence of an ABC containing protein may comprise all or part of the NBD domain of a Phospholipid-Transporting ATPase (ABC or ABCA1 transporter) encoded by the ABCA1 gene, UniProtKB—O95477 (SEQ ID NO:1). A NBD may comprise a sequence having at least about 90% or at least about 95% sequence identity to SEQ ID NO:1.

A NBD aa sequence may comprise all or part of the NBD domain of Multidrug Resistance Protein 1 (MDR/TAP) encoded by the ABCB1 gene, UniProtKB—P08183 (SEQ ID NO:2). A NBD may comprise a sequence having at least about 90% or at least about 95% sequence identity to SEQ ID NO:2.

A NBD aa sequence may comprise all or part of the NBD domain of a Multidrug resistance-associated protein (MRP, Multidrug resistance-associated protein 1) encoded by the ABCC1 gene, UniProtKB—P33527 (SEQ ID NO:3). A NBD may comprise a sequence having at least about 90% or at least about 95% sequence identity to SEQ ID NO:3.

A NBD aa sequence may comprise all or part of the NBD domain of an ATP-binding cassette subfamily D member 1 protein (ALD, Adrenoleukodystrophy Protein) encoded by the ABCD1 gene, UniProtKB/Swiss-Prot: P33897 (SEQ ID NO:4). A NBD may comprise a sequence having at least about 90% or at least about 95% sequence identity to SEQ ID NO:4.

A NBD aa sequence may comprise all or part of the NBD domain of an ATP-binding cassette subfamily E member 1 protein (OABP, 2'-5'-Oligoadenylate-Binding Protein) encoded by the ABCE1 gene, UniProtKB/Swiss-Prot: P61221 (SEQ ID NO:5). A NBD may comprise a sequence having at least about 90% or at least about 95% sequence identity to SEQ ID NO:5.

A NBD aa sequence may comprise all or part of the NBD domain of an ATP-binding cassette subfamily F member 1 protein (GCN20, TNFalpha-Inducible ATP-Binding Protein) encoded by the ABCF1 gene, UniProtKB—Q8NE71 (SEQ ID NO:6). A NBD may comprise a sequence having at least about 90% or at least about 95% sequence identity to SEQ ID NO:6.

A NBD aa sequence may comprise all or part of the NBD domain of an ATP-binding cassette subfamily G member 1 protein (White, Homolog Of Drosophila White) encoded by the ABCG2 gene, UniProtKB/Swiss-Prot: P45844 (SEQ ID NO:7). A NBD may comprise a sequence having at least about 90% or at least about 95% sequence identity to SEQ ID NO:7.

(1) TAP1 and TAP2 ATP Binding Cassettes as NBDs

The TAP1 and TAP2 proteins are cognate binding partners that act as a transporter coupling ATP binding and heterodimerization with peptide translocation across inner cell membranes. TAP1 and TAP2 are members of the ABC transporter superfamily that represents a source of NBDs for use in the constructs provided herein. Rat TAP1 NBD is known to undergo homodimerization in the presence of ATP. The NBD of human TAP1 does not undergo homodimerization in the presence of ATP, but can be induced to undergo homodimerization using previously defined substitutions. See, e.g., Vakkasoglu et al. (2017) "D-helix influences dimerization of the ATP-binding cassette (ABC) transporter associated with antigen processing 1 (TAP1) nucleotide-binding domain," *PLoS ONE,* 12(5): e0178238; on the world wide web at doi.org/10.1371/journal.pone.0178238. Substitutions leading to TAP1 homodimerization include those at one or more (e.g., each of) N676, S677, Q680, E682, and Q683, which are bolded and italicized in SEQ ID NO:8. For example, the TAP1 substitutions leading to homodimerization may include one or more (e.g., all) of N676G, S677N, Q680R, E682Q, and Q683R substitutions. The portions (e.g., domains) of TAP1 and TAP2 proteins employed as NBDs may also include substitutions of one or more cysteines present in the sequence (e.g., with serine residues) to prevent undesirable disulfide bond formation leading to non-functional folding or undesirable intermolecular disulfide bond formation. TAP1 and TAP2 NBDs may also include a His tag, for example at the C-terminus of the domain for purification of constructs comprising those NBDs.

A NBD aa sequence from human TAP1 (SEQ ID NO:9) may, for example, comprise an aa sequence having greater than 90% or greater than 95% sequence identity to the NBD aa sequence (aas 492-748) of NCBI Reference Sequence: NP_000584.3 of SEQ ID NO:8, or of UniProtKB—Q03518-2:

```
                         (Reference Sequence: NP_000584.2, SEQ ID NO: 8)
  1  MASSRCPAPR GCRCLPGASL AWLGTVLLLL ADWVLLRTAL PRIFSLLVPT ALPLLRVWAV

61  GLSRWAVLWL GACGVLRATV GSKSENAGAQ GWLAALKPLA AALGLALPGL ALFRELISWG

121  APGSADSTRL LHWGSHPTAF VVSYAAALPA AALWHKLGSL WVPGGQGGSG NPVRRLLGCL

181  GSETRRLSLF LVLVVLSSLG EMAIPFFTGR LTDWILQDGS ADTFTRNLTL MSILTIASAV

241  LEFVGDGIYN NTMGHVHSHL QGEVFGAVLR QETEFFQQNQ TGNIMSRVTE DTSTLSDSLS

301  ENLSLFLWYL VRGLCLLGIM LWGSVSLIMV TLITLPLLFL LPKKVGKWYQ LLEVQVRESL

361  AKSSQVAIEA LSAMPTVRSF ANEEGEAQKF REKLQEIKTL NQKEAVAYAV NSWTTSISGM

421  LLKVGILYIG GQLVTSGAVS SGNLVTFVLY QMQFTQAVEV LLSIYPRVQK AVGSSEKIFE

481  YLDRTPRCPP SGLLTPLHLE GLVQFQDVSF AYPNRPDVLV LQGLTFTLRP GEVTALVGPN

541  GSGKSTVAAL LQNLYQPTGG QLLLDGKPLP QYEHRYLHRQ VAAVGQEPQV FGRSLQENIA

601  YGLTQKPTME EITAAAVKSG AHSFISGLPQ GYDTEVDEAG SQLSGGQRQA VALARALIRK

661  PCVLILDDAT SALDA*NSQLQ* V*E*QLLYESPE RYSRSVLLIT QHLSLVEQAD HILFLEGGAI

721  REGGTHQQLM EKKGCYWAMV QAPADAPE;
```

The TAP1 NBD domain common to both the NCBI and UniProt sequence is:

1 GLLTPLHLEG LVQFQDVSFA YPNRPDVLVL QGLTFTLRPG EVTALVGPN GSGKSTVAALL 61 QNLYQPTGGQ LLLDGKPLPQ YEHRYLHRQV AAVGQEPQVF GRSLQENIA YGLTQKPTMEE 121 ITAAAVKSGA HSFISGLPQG YDTEVDEAGS QLSGGQRQAV ALARALIRKP CVLILDDATS 181 ALDANSQLQV EQLLYESPER YSRSVLLITQ HLSLVEQADH ILFLEGGAIR EGGTHQQLME 241 KKGCYWAMVQ APADAPE (SEQ ID NO:9). Residues N676, S677, Q680, E682, and Q683 of SEQ ID NO:8, associated with homodimerization, appear as N185, S186, Q189, E191, and Q192 in SEQ ID NO:9 and are bolded and italicized. A NBD aa sequence from human TAP1 may, for example, comprise an aa sequence having greater than 97% or greater than 98% sequence identity to at least 230 contiguous aas of the NBD of the aa sequence set forth in NCBI Reference Sequence: NP_000584.2 (aas 492-748) provided as SEQ ID NO:9.

A NBD aa sequence from human TAP1 may, for example, comprise substitutions at the aa residues corresponding to C662 (e.g., C662S) and C735 (e.g., C735S) of SEQ ID NO:8. The NBD aa sequence from human TAP1 may also, for example, comprise substitutions at aas corresponding to one or more of N676, S677, Q680, E682, and Q683 (e.g., N676G, S677N, Q680R, E682Q, and/or Q683R) of SEQ ID NO:8, which are bolded and italicized in SEQ ID NO: 10 below. The NBD aa sequence from human TAP1 may also comprise a substitution at, for example, the Asp corresponding to D668 of SEQ ID NO:8, which renders the NBD ATP hydrolysis-deficient. Accordingly, a NBD polypeptide aa sequence of TAP1 may, for example, comprise the aa sequence of SEQ ID NO:10, or an aa sequence having greater than 90% or greater than 95% sequence identity to that sequence:

```
                                                          (SEQ ID NO: 10)
  1  GLLTPLHLEG LVQFQDVSFA YPNRPDVLVL QGLTFTLRPG EVTALVGPNG SGKSTVAALL

61  QNLYQPTGGQ LLLDGKPLPQ YEHRYLHRQV AAVGQEPQVF GRSLQENIAY GLTQKPTMEE

121  ITAAAVKSGA HSFISGLPQG YDTEVDEAGS QLSGGQRQAV ALARALIRKP SVLILDNATS

181  GNQLRV QRLLYESPER YSRSVLLITQ HLSLVEQADH ILFLEGGAIR EGGTHQQLME

241  KKGSYWAMVQ APADAPE.
```

Alternatively, the NBD aa sequence may have greater than 97% or greater than 98% sequence identity to at least 230 or 240 contiguous aas of the sequence provided in SEQ ID NO: 10.

A NBD aa sequence from human TAP1 may, for example, comprise substitutions corresponding to those at C662 (e.g., C662S) and C735 (e.g., C735S) of SEQ ID NO:8. The NBD aa sequence from human TAP1 may also, for example, comprise substitutions corresponding to those at one or more of N676, S677, Q680, E682, and Q683 (e.g., N676G, S677N, Q680R, E682Q, and/or Q683R) in SEQ ID NO:8, which are bolded and italicized in SEQ ID NO:87 below. In addition, the NBD aa sequence from human TAP1 may comprise a substitution at the Asp corresponding to D668 of SEQ ID NO:8, which renders the NBD ATP hydrolysis-deficient. Accordingly, a NBD polypeptide aa sequence of TAP1 may, for example, comprise the aa sequence of SEQ ID NO:87 or an aa sequence having greater than 90% or greater than 95% sequence identity to that sequence:

```
                                                          (SEQ ID NO: 87)
  1  MPPSGLLTPL HLEGLVQFQD VSFAYPNRPD VLVLQGLTFT LRPGEVTALV GPNGSGKSTV

61  AALLQNLYQP TGGQLLLDGK PLPQYEHRYL HRQVAAVGQE PQVFGRSLQE NIAYGLTQKP

121  TMEEITAAAV KSGAHSFISG LPQGYDTEVD EAGSQLSGGQ RQAVALARAL IRKPSVLILD

181  NATSALDAGN QLRVQRLLYE SPERYSRSVL LITQHLSLVE QADHILFLEG GAIREGGTHQ

241  QLMEKKGSYW AMVQAPADAP E
```

Alternatively, the NBD aa sequence may have greater than 97% or greater than 98% sequence identity to at least 250 or 260 contiguous aas of the sequence provided in SEQ ID NO:87.

A NBD aa sequence from human TAP1 may, for example, comprise substitutions corresponding to those at C662 (e.g., C662S) and C735 (e.g., C735S) of SEQ ID NO:8. The NBD aa sequence from human TAP1 may also, for example, comprise substitutions corresponding to those at one or more of N676, S677, Q680, E682, and Q683 (e.g., N676G, S677N, Q680R, E682Q, and/or Q683R) in SEQ ID NO:8, which are bolded and italicized in SEQ ID NO:88 below. In addition, the NBD aa sequence from human TAP1 may comprise a substitution at the aa corresponding to D668 of SEQ ID NO:8 (e.g., a D668N substitution), which renders the NBD ATP hydrolysis-deficient. Accordingly, a NBD polypeptide aa sequence of TAP1 may, for example, comprise the aa sequence of SEQ ID NO:88 or an aa sequence having greater than 90% or greater than 95% sequence identity to that sequence:

```
                                                           (SEQ ID NO: 88)
  1   METEFFQQNQ   TGGGGSGLQT   VRSFGGGGGS   GGSGLLTPLH   LEGLVQFQDV   SFAYPNRPDV

61   LVLQGLTFTL   RPGEVTALVG   PNGSGKSTVA   ALLQNLYQPT   GGQLLLDGKP   LPQYEHRYLH

121   RQVAAVGQEP   QVFGRSLQEN   IAYGLTQKPT   MEEITAAAVK   SGAHSFISGL   PQGYDTEVDE

181   AGSQLSGGQR   QAVALARALI   RKPSVLILDN   ATSALDAGNQ   LRVQRLLYES   PERYSRSVLL

241   ITQHLSLVEQ   ADHILFLEGG   AIREGGTHQQ   LMEKKGSYWA   MVQAPADAPE
```

Alternatively, the NBD aa sequence may have greater than 97% or greater than 98% sequence identity to at least 300 or 310 contiguous aas of the sequence provided in SEQ ID NO:88. The NBD provided in SEQ ID NO:88 comprises, in addition to TAP1 NBD sequences, the coupling helix 1 (CH1, aas 2-11) from TAP1 and coupling helix 2 (CH2, aas 17-25) from TAP2, and associated GS linkers (aas 12-16 and 25-30), which together constitute a "cap" on the sequence. TAP1 NBD constructs express at substantially higher levels in biological expression systems as shown in Example 3.

In some cases NBDs from TAP proteins that do not homodimerize, but rather heterodimerize with a cognate NBD, are used to prepare pairs of constructs (see, e.g., FIG. 2 at B and D and FIG. 3) or complexes of constructs (see, e.g., FIG. 4A) of the present disclosure. For example, a pair of constructs bearing human TAP1 NBDs and human TAP2 NBDs can be prepared. The pair of constructs comprising TAP1 and TAP2 NBDs will form heterodimers through interaction of TAP1 and TAP2 in the presence of sufficient ATP. Using NBDs such as TAP1 and TAP2 that can heterodimerize permits different specific combinations of activating sequences to be combined for immune cell stimulation. By way of example, a construct comprising IL-12A (p35), an optional linker aa sequence, and TAP1 can heterodimerize in the presence of sufficient ATP with a construct comprising IL-12B (p40), an optional linker aa sequence, and TAP2 to form a pair of constructs presenting an active IL-12AB heterodimer. Such constructs may also comprise a scaffold aa sequence such as an Ig Fc aa sequence if desired.

FIG. 7 provides the sequence of human TAP2. In some cases a NBD of a construct of the present disclosure may comprise an aa sequence from the NBD from human TAP2 or an aa sequence having greater than 90% or greater than 95% sequence identity to a human TAP2 NBD. For example, the NBD may comprise an aa sequence having greater than 90% or greater than 95% sequence identity to the NBD aa sequence of UniProtKB—Q03519 (TAP2_HUMAN):

```
                                                           (SEQ ID NO: 11)
  1   MRLPDLRPWT   SLLLVDAALL   WLLQGPLGTL   LPQGLPGLWL   EGTLRLGGLW   GLLKLRGLLG

61   FVGTLLLPLC   LATPLTVSLR   ALVAGASRAP   PARVASAPWS   WLLVGYGAAG   LSWSLWAVLS

121   PPGAQEKEQD   QVNNKVLMWR   LLKLSRPDLP   LLVAAFFFLV   LAVLGETLIP   HYSGRVIDIL

181   GGDFDPHAFA   SAIFFMCLFS   FGSSLSAGCR   GGCFTYTMSR   INLRIREQLF   SSLLRQDLGF

241   FQETKTGELN   SRLSSDTTLM   SNWLPLNANV   LLRSLVKVVG   LYGFMLSISP   RLTLLSLLHM

301   PFTIAAEKVY   NTRHQEVLRE   IQDAVARAGQ   VVREAVGGLQ   TVRSFGAEEH   EVCRYKEALE

361   QCRQLYWRRD   LERALYLLVR   RVLHLGVQML   MLSCGLQQMQ   DGELTQGSLL   SFMIYQESVG

421   SYVQTLVYIY   GDMLSNVGAA   EKVFSYMDRQ   PNLPSPGTLA   PTTLQGVVKF   QDVSFAYPNR

481   PDRPVLKGLT   FTLRPGEVTA   LVGPNGSGKS   TVAALLQNLY   QPTGGQVLLD   EKPISQYEHC
```

```
541  YLHSQVVSVG QEPVLFSGSV RNNIAYGLQS CEDDKVMAAA QAAHADDFIQ EMEHGIYTDV

601  GEKGSQLAAG QKQRLAIARA LVRDPRVLIL DEATSALDVQ CEQALQDWNS RGDRTVLVIA

661  HRLQTVQRAH QILVLQEGKL QKLAQL
```

A NBD may, for example, comprise an aa sequence having greater than 90% or greater than 95% sequence identity to the human TAP2 aa sequence:

(SEQ ID NO: 12)
GTLAPTTLQG VVKFQDVSFA YPNRPDRPVL KGLTFTLRPG EVTALVGPNG SGKSTVAALL

QNLYQPTGGQ VLLDEKPISQ YEHCYLHSQV VSVGQEPVLF SGSVRNNIAY GLQSCEDDKV

MAAAQAAHAD DFIQEMEHGI YTDVGEKGSQ LAAGQKQRLA IARALVRDPR VLILDEATSA

LDVQCEQALQ DWNSRGDRTV LVIAHRLQTV QRAHQILVLQ EGKLQK.

The NBD may also comprise an aa sequence having greater than 96% or greater than 98% sequence identity to SEQ ID NO:12.

A mutation removing the catalytic acidic aa residue corresponding to the D668N substitution of TAP1 rendering it ATP hydrolysis deficient may be incorporated into a TAP2 NBD aa sequence.

(2) CFTR ATP Binding Cassettes as NBDs

In some cases a NBD of a construct of the present disclosure may comprise an aa sequence from the NBD from human cystic fibrosis transmembrane conductance regulator (CFTR) or an aa sequence having greater than 90% or greater than 95% sequence identity to a human CFTR. For example, the NBD may comprise an aa sequence having greater than 90% or greater than 95% sequence identity to the NBD aa sequence of UniProtKB—P13569 (SEQ ID NO:13):

```
  1  MQRSPLEKAS VVSKLFFSWT RPILRKGYRQ RLELSDIYQI PSVDSADNLS

51  EKLEREWDRE LASKKNPKLI NALRRCFFWR FMFYGIFLYL GEVTKAVQPL

101  LLGRIIASYD PDNKEERSIA IYLGIGLCLL FIVRTLLLHP AIFGLHHIGM

151  QMRIAMFSLI YKKTLKLSSR VLDKISIGQL VSLLSNNLNK FDEGLALAHF

201  VWIAPLQVAL LMGLIWELLQ ASAFCGLGEL IVLALFQAGL GRMMMKYRDQ

251  RAGKISERLV ITSEMIENIQ SVKAYCWEEA MEKMIENLRQ TELKLTRKAA

301  YVRYENSSAF FFSGFFVVFL SVLPYALIKG IILRKIFTTI SFCIVLRMAV

351  TRQFPWAVQT WYDSLGAINK IQDFLQKQEY KTLEYNLTTT EVVMENVTAF

401  WEEGFGELFE KAKQNNNNRK TSNGDDSLFF SNFSLLGTPV LKDINFKIER

451  GQLLAVAGST GAGKTSLLMV IMGELEPSEG KIKHSGRISF CSQFSWIMPG

501  TIKENIIFGV SYDEYRYRSV IKACQLEEDI SKFAEKDNIV LGEGGITLSG

551  GQRARISLAR AVYKDADLYL LDSPFGYLDV LTEKEIFESC VCKLMANKTR

601  ILVTSKMEHL KKADKILILH EGSSYFYGTF SELQNLQPDF SSKLMGCDSF

651  DQFSAERRNS ILTETLHRES LEGDAPVSWT ETKKQSFKQT GEFGEKRKNS

701  ILNPINSIRK FSIVQKTPLQ MNGIEEDSDE PLERRLSLVP DSEQGEAILP

751  RISVISTGPT LQARRRQSVL NLMTHSVNQG QNIHRKTTAS TRKVSLAPQA

801  NLTELDIYSR RLSQETGLEI SEEINEEDLK ECFFDDMESI PAVTTWNTYL

851  RYITVHKSLI FVLIWCLVIF LAEVAASLVV LWLLGNTPLQ DKGNSTHSRN
```

```
 901    NSYAVIITST  SSYYVFYIYV  GVADTLLAMG  FFRGLPLVHT  LITVSKILHH

951    KMLHSVLQAP  MSTLNTLKAG  GILNRFSKDI  AILDDLLPLT  IFDFIQLLLI

1001    VIGAIAVVAV  LQPYIFVATV  PVIVAFIMLR  AYFLQTSQQL  KQLESEGRSP

1051    IFTHLVTSLK  GLWTLRAFGR  QPYFETLFHK  ALNLHTANWF  LYLSTLRWFQ

1101    MRIEMIFVIF  FIAVTFISIL  TTGEGEGRVG  IILTLAMNIM  STLQWAVNSS

1151    IDVDSLMRSV  SRVFKFIDMP  TEGKPTKSTK  PYKNGQLSKV  MIIENSHVKK

1201    DDIWPSGGQM  TVKDLTAKYT  EGGNAILENI  SFSISPGQRV  GLLGRTGSGK

1251    STLLSAFLRL  LNTEGEIQID  GVSWDSITLQ  QWRKAFGVIP  QKVFIFSGTF

1301    RKNLDPYEQW  SDQEIWKVAD  EVGLRSVIEQ  FPGKLDFVLV  DGGCVLSHGH

1351    KQLMCLARSV  LSKAKILLLD  EPSAHLDPVT  YQIIRRTLKQ  AFADCTVILC

1401    EHRIEAMLEC  QQFLVIEENK  VRQYDSIQKL  LNERSLFRQA  ISPSDRVKLF

1451    PHRNSSKCKS  KPQIAALKEE  TEEEVQDTRL
```

A NBD may, for example, comprise an aa sequence having greater than 80% or greater than 85% sequence identity to the human CFTR aa sequence: VLKDINFKIERGQLLAVAGSTGAGKTSLLMVIMGELEPSEGK IKHSGRISFCSQFSWIMPGTIKENIIFGVSYDEYRYRSVIKACQLEEDISKFAEKDNIVLGEG-GITLSGGQRARISLARAV YKDADLYLLD-SPFGYLDVLTEKEIFESCVCKLMANKTRILVTSKMEH LKKADKILILHEGSSYFYGTFSELQNLQPDF (SEQ ID NO:14). Alternatively, the NBD may, for example, comprise an aa sequence having greater than 90% or greater than 95% sequence identity to SEQ ID NO:14. The NBD may also comprise an aa sequence having greater than 96% or greater than 98% sequence identity to SEQ ID NO: 14.

A NBD may, for example, comprise an aa sequence having greater than 80% or greater than 85% sequence identity to the human CFTR aa sequence Ser-NBD1[387-646(D405-436)] described in Atwell et al., (2010), Protein Engineering, Design & Selection, 23(5) 375-384: SXTTTE-VVMENVTAFWEEGGTPVLKDINFKIER GQLLAVAG-STGAGKTSLLMVIMGELEPSEGKIKHSGRIS-FCSQFSWIMPGTIKENIIFGVSYDEYRYRSVIKACQLE EDI SKFAEKDNIVLGEGGITLSGGQRARISLARAVYK-DADLYLLDSPFGYLDVLTEKEIFESCVCKL-MANKTRILVTSKMEHL KKADKILILH EGSSYFYGTFSELQNLQPDFSSKLMX (SEQ ID NO: 15), where X at position 2 may be absent or L; and X at position 229 is absent or G. Alternatively, the NBD may, for example, comprise an aa sequence having greater than 90% or greater than 95% sequence identity to SEQ ID NO:15. The NBD may also comprise an aa sequence having greater than 96% or greater than 98% sequence identity to SEQ ID NO: 15. A NBD may, for example, comprise an aa sequence having greater than 90% or greater than 95% sequence identity to aas 1-216 of SEQ ID NO:16, where X at position 2 may be absent or L.

2. Scaffolds

Scaffold aa sequences may be incorporated into the ATP-dependent agonists constructs described herein as a means of structural organization, to increase the half-life of the molecules in vivo, and, where capable of inducing ADCC, ADCP, and/or CDC, to act as a basis for those effector functions. The scaffolds may be capable of forming dimers and higher order complexes (e.g., trimers) or non-dimerizable (non-dimerizing) in which case they do not form dimers or higher order complexes. Scaffolds incorporated into the constructs described herein may, for example, comprise an immunoglobulin (Ig) aa sequence or non-immunoglobulin aa sequence.

In some embodiments, the scaffold polypeptide sequence comprises an immunoglobulin heavy chain constant region (CH2-CH3) polypeptide sequence that functions as a dimerization or multimerization sequence. Where the scaffold comprises an immunoglobulin (Ig) aa sequence, it may comprise an immunoglobulin heavy chain constant region (CH2-CH3) polypeptide aa sequence (e.g., an IgFc aa sequence). The scaffold aa sequence may, for example, comprise Ig CH2 and/or CH3 aa sequences modified to prevent dimerization. Any one or more cysteines involved in interchain disulfide bonds that stabilize an Ig heavy chain dimers may be substituted (e.g., with an alanine or serine) so that the Ig heavy chain sequence cannot homodimerize and form interchain disulfide bonds. A scaffold polypeptide may comprise the wild-type (wt) Homo sapiens IgG1 Fc polypeptide sequence of (SEQ ID NO:56):

1 DKTHTCPPCP APELLGGPSV FLFPPKPKDT LMIS-RTPEVT CVVVDVSHED PEVKENWYVD 61 GVEVHNAKTK PREEQYNSTY RVVSVLTVLH QDWLNGKEYK CKVSNKALPA PIEKTISKAK 121 GQPREPQVYT LPPSREEMTK NQVSLTCLVK GFYPS-DIAVE WESNGQPENN YKTTPPVLDS 181 DGSFFLY-SKL TVDKSRWQQG NVESCSVMHE ALHNHYTOKS LSLSPGK; optionally modified to prevent dimerization. Alternatively, the scaffold may, for example, comprise an aa sequence having greater than 90% or greater than 95% sequence identity to SEQ ID NO:56. The scaffold may also comprise an aa sequence having greater than 96% or greater than 98% sequence identity to SEQ ID NO:56.

A scaffold polypeptide may comprise a Homo sapiens IgG1 Fc aa sequence of SEQ ID NO:57, which comprises a LALA substitution (L234A, L235A substitutions, appearing as bolded and italicized aas 14 and 15 respectively):

1 DKTHTCPPCP APEAAGGPSV FLFPPKPKDT LMISRTPEVT CVVVDVSHED PEVKENWYVD 61 GVEVHNAKTK PREEQYNSTY RVVSVLTVLH QDWLNGKEYK CKVSNKALPA PIEKTISKAK 121 GQPREPQVYT LPPSRDELTK NQVSLTCLVK GFYPS-DIAVE WESNGQPENN YKTTPPVLDS 181 DGSFFLY-SKL TVDKSRWQQG NVFSCSVMHE ALHNHYTOKS LSLSPG; optionally modified to prevent dimerization. Alternatively, the scaffold may, for example, comprise an aa sequence having greater than 90% or greater than 95% sequence identity to SEQ ID NO:57. The scaffold may also comprise an aa sequence having greater than 96% or greater than 98% sequence identity to SEQ ID NO:57

Non-dimerizing scaffolds may be prepared as human single chain Fc (scFc) dimers. See, e.g., Zhou et al., Biomaterials 117:24-31 (2017). Such scFc dimers may be based on IgG1 and have the sequence:

1 DKTHTCPPCP APELLGGPSV FLFPPKPKDT LMIS-RTPEVT CVVVDVSHED PEVKENWYVD 61 GVEVHNAKTK PREEQYNSTY RVVSVLTVLH QDWLNGKEYK CKVSNKALPA PIEKTISKAK 121 GQPREPQVYT LPPSRDELTK NQVSLTCLVK GFYPS-DIAVE WESNGQPENN YKTTPPVLDS 181 DGSFFLY-SKL TVDKSRWQQG NVFSCSVMHE ALHNHYTQKS LSLSPGGGGG SGGGGSGGGG 241 SGGGGSGGGG SGGGGSDKTH TCPPCPAPEL LGGPSVFLFP PKPKDTLMIS RTPEVTCVVV 301 DVSHEDPEVK FNWYVDGVEV HNAKTKPREE QYNSTYRVVS VLTVLHQDWL NGKEYKCKVS 361 NKALPAPIEK TISKAKGQPR EPQVYTLPPS RDELTKNQVS LTCLVKGFYP SDIAVEWESN 421 GQPENNYKTT PPVLDSDGSF FLYSKLTVDK SRWQQGNVFS CSVMHEALHN HYTQKSLSLS 481 PG (SEQ ID NO:102). Alternatively, the scaffold may, for example, comprise an aa sequence having greater than 90% or greater than 95% sequence identity to SEQ ID NO:102. The scaffold may also comprise an aa sequence having greater than 96% or greater than 98% sequence identity to SEQ ID NO:102. The scaffold construct of SEQ ID NO: 102 is competent for the induction of ADCC, ADCP, and CDC, but substitutions including "LALA" discussed below may be introduced to selectively alter the ability of the scFc to induce those effector functions.

A scaffold polypeptide may comprise the wt *Homo sapiens* IgG2 Fc polypeptide of SEQ ID NO:58 (see GenBank AAN76044 amino acids 99-325):

1 STKGPSVEPL APCSRSTSES TAALGCLVKD YFPEPVTVSW NSGALTSGVH TFPAVLQSSG 61 LYS-LSSVVTV PSSNFGTQTY TCNVDHKPSN TKVDKTVERK CCVECPPCPA PPVAGPSVEL 121 FPPKPKDTLM ISRTPEVTCV VVDVSHEDPE VQFNWYVDGV EVHNAKTKPR EEQFNSTERV 181 VSVLTVVHOD WLNGKEYKCK VSNKGLPAPI EKTISKTKGQ PREPQVYTLP PSREEMTKNQ 241 VSLTCLVKGF YPSDIAVEWE SNGQPENNYK 45 TTPPMLDSDG SFFLYSKLTV DKSRWQQGNV 301 FSCSVMHEAL HNHYTOKSLS LSPGK; optionally modified to prevent dimerization. Alternatively, the scaffold may, for example, comprise an aa sequence having greater than 90% or greater than 95% sequence identity to SEQ ID NO:58. The scaffold may also comprise an aa sequence having greater than 96% or greater than 98% sequence identity to SEQ ID NO:58.

A scaffold polypeptide may comprise the wt *Homo sapiens* IgG3 Fc polypeptide of SEQ ID NO:59 (see, e.g., GenBank AAW65947 amino acids 19-246):

1 HKPSNTKVDK RVELKTPLGD TTHTCPPCPA PELLGGPSVF LFPPKPKDTL MISRTPEVTC 61 VVVDVSHEDP EVKENWYVDG VEVHNAKTKP REEQYNSTYR VVSVLTVLHQ DWLNGKEYKC 121 KVSNKALPAP IEKTISKAKG QPREPQVYTL PPSRDELTKN QVSLTCLVKG FYPSDIAVEW 181 ESNGQPENNY KTTPPVLDSD GSFFLYSKLT VDKSRWQQGN VFSCSVMHEA LHNHYTQKSL 241 SLSPGK; optionally modified to prevent dimerization. Alternatively, the scaffold may, for example, comprise an aa sequence having greater than 90% or greater than 95% sequence identity to SEQ ID NO:59. The scaffold may also comprise an aa sequence having greater than 96% or greater than 98% sequence identity to SEQ ID NO:59.

A scaffold polypeptide may comprise the wt *Homo sapiens* IgG4 Fc polypeptide of SEQ ID NO:60:

1 PPCPSCPAPE FLGGPSVFLF PPKPKDTLMI SRTPE-VTCVV VDVSQEDPEV QFNWYVDGVE 61 VHNAKTKPRE EQFNSTYRVV SVLTVLHQDW LNGKEYKCKV SNKGLPSSIE KTISKAKGQP 121 REPQVYTLPP SQEEMTKNQV SLTCLVKGFY PSDIA-VEWES NGQPENNYKT TPPVLDSDGS 181 FFLY-SRLTVD KSRWQEGNVF SCSVMHEALH NHYTQKSLSL SPG; optionally modified to prevent dimerization. Alternatively, the scaffold may, for example, comprise an aa sequence having greater than 90% or greater than 95% sequence identity to SEQ ID NO:60. The scaffold may also comprise an aa sequence having greater than 96% or greater than 98% sequence identity to SEQ ID NO:60.

Interactions of the IgG class of antibodies that lead to, for example, ADCC and ADCP, occur by their Fc region engaging with members of the Fcγ family of receptors (FcγRs). The human protein family is comprised of FcγRI (CD64), FcγRII (CD32, which includes isoforms FcγRIIa, FcγRIIb, and FcγRIIc), and FcγRIII (CD16, which includes isoforms FcγRγIIIa and FcγRIIIb). See, e.g., Lazar et al. (2006) PNAS: 103 (11), 4005-4010.

Among the variants that can enhance one or more antibody related effector functions (e.g., ADCC, ADCP, and/or CDC responses) are: the individual substitutions S239D and I332E; and the double and triple substitutions at S239D/I332E and S239D/I332E/A330L in human IgG1. Substitutions corresponding to S239D, I332E, and A330L in the human IgG1 Fc sequence (SEQ ID NO:56) are S19D, 1112E, and A110L. In an embodiment, the substitutions are the double and triple mutants S239D/I332E or S239D/I332E/A330L. See Lazar et al., 2006.

Other substitutions that enhance one or more antibody related effector function in IgG1 antibodies include, but are not limited to: Ser298Ala/Glu333Ala/Lys334Ala; Ser239Asp/Ala330Leu/Ile332Glu; Ser239Asp/Ile332Glu; Gly236Ala/Ser239Asp/Ala330Leu/Ile332Glu; Gly236Ala; Ser239Asp/Ile332Glu/Gly236Ala; Leu234Tyr/Gly236Trp/Ser298Ala; Phe243Leu/Arg292Pro/Tyr300Leu/Val305Ile/Pro396Leu; Lys326Trp/Glu333Ser; Lys326Ala/Glu333Ser; Lys326Met/Glu333Ser; Cys221Asp/Asp222Cys; Ser267Glu/His268Phe/Ser324Thr; His268Phe/Ser324Thr; and Glu345Arg. See, Saunders KO (2019) Front. Immunol. 10:1296.doi: 10.3389/fimmu.2019.01296. The corresponding location in the IgG1 Fc sequence of SEQ ID NO:56 can be obtained by subtracting 220 from the indicated positions. In an embodiment at least ADCC is enhanced by the substitutions. In an embodiment at least ADCP is enhanced by the substitutions. In an embodiment at least CDC is enhanced by the substitutions. In an embodiment at least complement fixation is enhanced by the substitutions.

Variants that can substantially diminish one or more antibody related effector functions of IgG1 antibodies (e.g., ADCC, ADCP, and/or CDC responses) include, but are not limited to: Leu235Glu; Leu234Ala/Leu235Ala (LALA); Ser228Pro/Leu235Glu; Leu234Ala/Leu235Ala/Pro329Gly; Pro331Ser/Leu234Glu/Leu235Phe; Asp265Ala; Gly237Ala; Glu318Ala; Glu233Pro; and Gly236Arg/Leu328Arg. As indicated above, the corresponding location of those substitutions in the IgG1 Fc sequence provided as SEQ ID NO:56 can be obtained by subtracting 220 from the indicated positions. In an embodiment, the scaffold sequence comprises an IgG1 Fc sequence with a LALA substitution (see, e.g., SEQ ID NO:57). In an embodiment at least ADCC is substantially diminished by the substitutions. In an embodiment at least ADCP is substantially diminished by the substitutions. In an embodiment at least CDC is substantially diminished by the substitutions. In an embodiment at least complement fixation is substantially diminished by the substitutions. See, e.g., Saunders 2019 and citations therein. In an embodiment the IgG1 Fc substitutions may be S239D/I332E/A330L, which permit enhancement of ADCC without substantially altering the CDC function (see Lazar et al., 2006).

Other variants in IgG1, IgG2, and IgG4 antibody sequences that can substantially diminish one or more antibody related effector functions include, but are not limited to: His268Gln/Val309Leu/Ala330Ser/Pro331Ser (IgG2m4); Val234Ala/Gly237Ala/Pro238Ser/His268Ala/Val309Leu/Ala330Ser/Pro331Ser (IgG2g); Leu234Ala/L235Ala/Gly237Ala/P238Ser/His268Ala/Ala330Ser/Pro331Ser (IgG10); and S228P/Phe234Ala/Leu235Ala (IgG4PAA). See, e.g., Saunders 2019 and citations therein.

Alternative non-dimerizing scaffold domains include, but are not limited to, XTENylation, PEGylation, Lipidation (see pubs.acs.org/doi/10.1021/acsmedchemlett.8b00226 on the world wide web "www"), Human Serum Albumin (HSA) fusions (see nature.com/articles/s42003-021-01790-2 on the www) and anti HSA binding domains, including but not limited to anti-HSA peptides (see pubs.acs.org/doi/10.1021/acs.molpharmaceut.2c00106 on the www), antibody and antibody fragments (e.g. ScFvs, FABs, etc) and VHH domains (see semanticscholar.org/paper/Serum-albumin %E2%80%90binding-VHHs-with-variable-pH-enable-Faassen-Ryan/d34256a0d39a0ab92db9195210fa0fc7430758b6 on the www).

3. Linkers

The constructs of the present disclosure optionally have linkers located between any two elements. The linkers can be located between any two of the NBD aa sequence, the scaffold aa sequence, and the AD. Linkers are typically comprised of aa sequences from 4 to 50 aas in length (e.g., from 4 to 25 aas or from 25 to 50 aas) and may be chosen for, among other things, their rigidity. Linkers are each selected independently.

In some instances, linkers are flexible aa sequences that are comprised of glycine, serine, and/or alanine residues. In other instances, linkers are aa sequences comprised of glycine and serine. For example, the sequence GGGS (SEQ ID NO: 16) or the sequence GGGGS (SEQ ID NO:26) may appear or be repeat from 1-10 times in the linkers (GGGS)$_{1-10}$ (SEQ ID NOs: 16-25) or (GGGGS)$_{1-10}$ (SEQ ID NOs:26-35). In some cases where linkers comprise a GGGS or GGGGS sequence, those sequences may appear from 1-5 or from 5-10 times.

Rigid linkers may be employed where it is desirable to maintain a substantially fixed distance or spatial separation between the domains to reduce or substantially eliminate unfavorable interactions between domains of the constructs (e.g., between NBDs in the same construct). For example, a pair of NBDs present in a single molecule may kept from self-associating through the use of rigid linkers. Exemplary rigid peptide or polypeptide linkers include linkers comprising the sequence X(EAAAK)n X, where EAAAK may appear in the linker from 1-20 times (i.e., 1, 2, 3, 4, 5, 6, 7, 8, 9, 10, 11, 12, 13, 14, 15, 16, 17, 18, 19, or 20 times, SEQ ID NOs:36-55) and where X is absent or alanine. In some cases where linkers comprise the X(EAAAK)n X sequence, n may be from 1-5 or from 5-10. In some cases where linkers comprise the X(EAAAK)n X sequence, n may be from 11-15 or from 16-20. Alternatively, rigid peptide linkers may comprise repeats of (Lys-Pro), (Glu-Pro), (Thr-Pro-Arg), and (Ala-Pro) having a length of 4 to 40 (e.g., 4-20 or 20-40 amino acids). Other rigid linkers include linkers comprising repeats of the dipeptide sequence KP or EP from 2 to 10 or 10 to 20 times.

4. Immune Cell Engaging Domains

Immune cell engaging domains (also referred to as an immune cell engager, "ICE" or "ICEs" when plural) are domains of the NBD-containing constructs that can bind to immune cell surface molecules. Immune cell engagers are typically antibody-related molecules/aa sequences (e.g., an antigen binding fragment of an antibody, Fab, Fab', single chain antibody, scFv, peptide aptamer, or nanobody). Unless stated otherwise, immune cell engagers are understood to be monovalent to prevent individual molecules from crosslinking the cellular target (e.g., immune cell surface antigen) and off target stimulation of the immune cell. Individual immune cell engagers are generally incapable of acting as an agonist and stimulating the immune cells to which they bind; however, when multiple constructs bearing an immune cell engager are localized in a complex (see, e.g., FIG. 4A at D or E) or immobilized on the surface of a tumor cell (e.g., using a construct such as in FIG. 3 at C), the immune cell engager may function as an agonist of the immune cell stimulation/activation.

Immune cell engagers may be directed to a number of different immune cells that appear or may be recruited into the TME. Such immune cells and the targets of their corresponding immune cell engagers include those set forth in Table 1.

TABLE 1

Some Immune cells and their corresponding immune cell engager

| Immune cell | Immune cell engager target/immune cell engager (e.g., antibody or antibody-related molecules‡ directed against target) |
| --- | --- |
| CD4+ T cell | CD3/ anti-CD3γ or anti-CD3ε; αβTCR/ anti-TCRα chain or anti-TCRβ chain; CD4/anti-CD4 |
| CD4+ T regs | CD25; |
| CD8+ T cell | CD3/ anti-CD3γ or anti-CD3ε; αβTCR/ anti-TCRα chain or anti-TCRβ chain CD8/anti-CD8 |
| δγ T cell | δγ TCR/ anti-TCRδ chain or anti-TCRγ chain (e.g., TRGV9/ anti-TRGV9 |
| NK Cell | CD16/ anti-CD16 |
| MDSC (myeloid derived suppressor cells) | CD84/anti-CD84; CXCR1/anti-CXCR1; DR5/anti-DR5; CD13/ anti-CD13; CD33/anti-CD33; CD34/anti-CD34; CD16/ anti-CD16 |

‡Antibody related molecules include, but are not limited to, antigen binding fragments of an antibody, Fabs, Fab's, and polypeptides comprising single chain antibody, scFv, peptide aptamer, or nanobody aa sequences.

When immune cell engagers such as those listed in Table 1 are incorporated into a first NBD-containing polypeptide construct that can pair or complex with a second NBD-containing construct comprising a tumor-specific binder directed against a TAA, then trans-targeting of tumor cells leading to their cytolysis may be observed (see, e.g., FIG. 3 at C, D, and F-H, and also complexes in FIG. 4A at E, F, H, and I). The incorporation of antibody-related molecules/aa sequences directed against immune cell surface proteins including, but not limited to, CD3, TCRs, and/or CD16 in such constructs and complexes may produce potent cytolytic action. Cytolytic activity may be enhanced when immune cell engagers that interact with more than one type of immune cell are employed. Some exemplary anti-CD3 immune cell engagers are provide below.

An immune cell engager polypeptide may be a scFv, anti-human CD3 based upon the UCHT-1 monoclonal antibody having the sequence: AIQMTQSPSSLSASVGDRVTITCRASQDIRNYLNWYQQKPGKAPKLLIYYTSRLESGVPSRFSGSGSGTDYTLTISSLQPEDFATYYCQQGNTLPWTFGQGTKVEIKGGGGSGGGGSGGGGSGGGGSGGGGSEVQLVESGGGLVQPGGSLRLSCAASGYSFTGYTMNWVRQAPGKGLEWVALIN PYKGVTTYADSVKGRFTISVDKSKNTAYLQMNSLRAEDTAVYYCARSGYYGDSDWYFDVWGQGTLVTVSS (SEQ ID NO:61). The immune cell engager may also comprise an aa sequence having greater than 90% or greater than 95% sequence identity to SEQ ID NO:61. In addition the immune cell engager may comprise an aa sequence having greater than 96% or greater than 98% sequence identity to SEQ ID NO:61.

An immune cell engager polypeptide may be a scFv, anti-human CD3 based upon the UCHT-1 monoclonal antibody having the sequence: AIQMTQSPSSLSASVGDRVTITCRASQDIRNYLNWYQQKPGKAPKLLIYYTSRLESGVPSRFSGSGSGTDYTLTISSLQPEDFATYYCQQGNTLPWTFGQGTKVEIKGGGGSGGGGSGGGGSGGGGSEVQLVESGGGLVQPGGSLRLSCAASGYSFTGYTMNWVRQAPGKGLEWVALIN PYKGVSTYNQKFKDRFTISVDKSKNTAYLQMNSLRAEDTAVYYCARSGYYGDSDWYFDVWGQGTLVTVSS (SEQ ID NO:62). The immune cell engager may also comprise an aa sequence having greater than 90% or greater than 95% sequence identity to SEQ ID NO:62. In addition the immune cell engager may comprise an aa sequence having greater than 96% or greater than 98% sequence identity to SEQ ID NO:62.

An immune cell engager polypeptide may be an anti-human CD3 VHH having the sequence: QVQLVESGGGLVQPGGSLRLSCAASGSIFSANTMGWYRQAPGKQRELVAGMNTSGSTVYGDSVKGRFTIS RDNAKNIAYLQMNSLIPEDTAVYYCTLVQRGPNYWGQGTQVTVSS (SEQ ID NO:63). The immune cell engager may also comprise an aa sequence having greater than 90% or greater than 95% sequence identity to SEQ ID NO:63. In addition the immune cell engager may comprise an aa sequence having greater than 96% or greater than 98% sequence identity to SEQ ID NO:63.

An immune cell engager polypeptide may be an anti-human CD3 scFv (vH-vL) based upon the L2K antibody having the sequence: DVQLVQSGAEVKKPGASVKVSCKASGYTFTRYTMHWVRQAPGQGLEWIGY INPSRGYTNYADSVKGRFTITTDKSTSTAYMELSSLRSEDTATYYCARYYDDHYCLDYWGQ GTTVTVSSG GGGSGGGGSGGGGSDIVLTQSPATLSLSPGERATLSCRASQSVSYMNWYQQKPGKAPKRWIYDTSKVASG VPARFSGSGSGTDYSLTINSLEAEDAATYYCQQWSSNPLTFGGGTKVEIK (SEQ ID NO:64). The immune cell engager may also comprise an aa sequence having greater than 90% or greater than 95% sequence identity to SEQ ID NO:64. In addition the immune cell engager may comprise an aa sequence having greater than 96% or greater than 98% sequence identity to SEQ ID NO:64.

An immune cell engager polypeptide may be an anti-human CD3 scFv (vH-vL) based upon the L2K antibody having the sequence set forth in SEQ ID NO:65, which includes a disulfide bond between the cysteine substitutions at Q43C and G99C (G233C as shown): DVQLVQSGAEVKKPGASVKVSCKASGYTFTRYTMHWVRQAPGCGLEWIGYINPSRGYTNYADSVKGRFTITTDKSTSTAYMELSSLRSEDTATYYCARYYDDHYCLD YWGQGTTVTVSSGGGGSGGGGSGGGGSDIVLTQSPATLSLSPGERATLSCRASQSVSYMNWYQQKPGKAP KRWIYDTSKVASGVPARFSGSGSGTDYSLTINSLEAEDAATYYCQQ WSSNPLTFGCGTKVEIK (SEQ ID NO:65). The immune cell engager may also comprise an aa sequence having greater than 90% or greater than 95% sequence identity to SEQ ID NO:65. In addition the immune cell engager may comprise an aa sequence having greater than 96% or greater than 98% sequence identity to SEQ ID NO:65.

An immune cell engager polypeptide may be an anti-human CD3 scFv (vH-vL) based upon the L2K antibody having the sequence set forth in SEQ ID NO:66, which includes a disulfide bond between the cysteine substitutions at Q43C and G100C (G234C as shown): DVQLVQSGAEVKKPGASVKVSCKASGYTFTRYTMHW VRQAPGCGLEWIGYINPSRGYTNYADSVKGRFTITTDKSTSTAYMELSSLRSEDTATYYCARYYDDHYCL DYWGQGTTVTVSSGGGGSGGGGSGGGGSDIVLTQSPATLSLSPGERATLSCRASQSVSYMNWYQQKPGKA PKRWIYDTSKVASGVPARFSGSGSGTDYSLTINSLEAEDAATYYCQQ WSSNPLTFGGCTKVEIK (SEQ ID NO:66). The immune cell engager may also comprise an aa sequence having greater than 90% or greater than 95% sequence identity to SEQ ID NO:66. In addition the immune cell engager may comprise an aa sequence having greater than 96% or greater than 98% sequence identity to SEQ ID NO:66.

An immune cell engager polypeptide may be an anti-human CD3 scFv (vH-vL) based upon the L2K antibody having the sequence set forth in SEQ ID NO:67, which includes a disulfide bond between the cysteine substitutions at G44C and: G99C (G233C as shown): DVQLVQSGAEVKKPGASVKVSCKASGYTFTRYTMHWV RQAPGQCLEWIGYINPSRGYTNYADSVKGRFTITTDKSTSTAYMELSSLRSEDTATYYCARYYDDHYCLD YWGQGTTVTVSSGGGGSGGGGSGGGGSDIVLTQSPATLSLSPGERATLSCRASQSVSYMNWYQQKPGKAP KRWIYDTSKVASGVPARFSGSGSGTDYSLTINSLEAEDAATYYCQQ WSSNPLTFGCGTKVEIK (SEQ ID NO:67). The immune cell engager may also comprise an aa sequence having greater than 90% or greater than 95% sequence identity to SEQ ID NO:67. In addition the immune cell engager may comprise an aa sequence having greater than 96% or greater than 98% sequence identity to SEQ ID NO:67.

An immune cell engager polypeptide may be an anti-human CD3 scFv (vH-vL) based upon the L2K antibody having the sequence set forth in SEQ ID NO:68, which includes a disulfide bond between the cysteine substitutions at G44C and G100C (G234C as shown):

1 DVQLVQSGAE VKKPGASVKV SCKASGYTFT RYTMHWVRQA PGQCLEWIGY INPSRGYTNY 61 ADSVKGRFTI TTDKSTSTAY MELSSLRSED TATYY-CARYY DDHYCLDYWG QGTTVTVSSG 121 GGGSGGGGSG GGGSDIVLTQ SPATLSLSPG ERATLSCRAS QSVSYMNWYQ QKPGKAPKRW 181 IYDTSKVASG VPARFSGSGS GTDYSLTINS LEAE-DAATYY CQQWSSNPLT FGGCTKVEIK (SEQ ID NO:68). The immune cell engager may also comprise an aa sequence having greater than 90% or greater than 95% sequence identity to SEQ ID NO:68. In addition the immune cell engager may comprise an aa sequence having greater than 96% or greater than 98% sequence identity to SEQ ID NO:68.

The GGGS (SEQ ID NO: 16) and/or GGGGS (SEQ ID NO:26) containing repeats in SEQ ID NOs:61-62 and 64-68, are linker sequences between domains.

5. Immune Cell Activating Domains (Activating Domains)

Activating Domains ("ADs" or "AD" when singular) that can be incorporated into constructs of the present disclosure include a variety of molecules or fragments of molecules (e.g., fragments of cytokines) that are capable of stimulating anti-tumor cell immune responses when presented as dimers or higher order complexes, but that have a limited ability to stimulate immune cells when presented singly. Some immune cell agonists that require receptor crosslinking for maximal activity include, but are not limited to, CD40L, CD28, IFN-g, and IL-12. Anti-tumor cell immune responses may result, for example, from the stimulation of NK cells or T cells (e.g., CD8+ T cells) by constructs comprising ADs, and may include granule dependent and granule independent responses.

ADs may comprise, for example, aa sequences of TNF superfamily members such as TNF, lymphotoxin α, lymphotoxin αβ, and BAFF (CD25). ADs may also comprise, for example, aa sequences of B7 superfamily members, such as CD80 and CD86. An AD may also comprise, for example, the aa sequence of all or part of IL-15, IL-12, IL-2, or IL-7 (e.g., all or part of the extracellular domain). An AD may comprise, for example, all or part of the aa sequence of IL-12 (e.g., one or both subunits of human IL-12).

By way of example some ADs that may be employed in constructs that homodimerize (see, e.g., FIG. 2 at A and C) or form homomeric complexes (see, e.g., FIG. 4A at A) in the presence of ATP levels found in the TME include, but are not limited to, immunomodulatory aa sequences of: IL-15, IL-12, or IL-7. Antibody related sequences (e.g., single chain scFV or nanobody sequences) having anti-PD1, anti-PDL1, anti-CD40, anti-CD40L, anti-CD137/4-1BB, anti-TGFβ, anti-IL-10, or anti-IL10R binding activity may also be employed.

In addition to the foregoing, nucleic acids, including nucleic acids with CpG repeats or one or more IMT504 sequences, may be used as ADs and may be incorporated into homodimerizing or heterodimerizing NBD-containing constructs.

An AD may comprise, for example, the CD80 polypeptide aa sequence:

1 VIHVTKEVKE VATLSCGHNV SVEELAQTRI YWQKEKKMVL TMMSGDMNIW PEYKNRTIFD 61 ITNNLSIVIL ALRPSDEGTY ECVVLKYEKD AFKREH-LAEV TLSVKADFPT PSISDFEIPT 121 SNIRRIICST SGGFPEPHLS WLENGEELNA INTTVSQDPE TELYAVSSKL DENMTTNHSF 181 MCLIKYGHLR VNQTENWNTT K (SEQ ID NO:99). Alternatively, an AD may comprise a sequence having at least 90% or at least 95% sequence identity with SEQ ID NO:99. An AD may also comprise a sequence having at least 96% or at least 98% sequence identity to at least 170 or 180 contiguous aas of SEQ ID NO:99.

An AD may comprise, for example, the CD86 polypeptide aa sequence comprising the CD86 (IgV-IgC domain):

```
                                                            (SEQ ID NO: 100)
  1   LKIQAYFNET ADLPCQFANS QNQSLSELVV FWQDQENLVL NEVYLGKEKF DSVHSKYMNR

61   TSFDSDSWTL RLHNLQIKDK GLYQCIIHHK KPTGMIRIHQ MNSELSVLAN FSQPEIVPIS

121   NITENVYINL TCSSIHGYPE PKKMSVLLRT KNSTIEYDGI MQKSQDNVTE LYDVSISLSV

181   SFPDVTSNMT IFCILETDKT RLLSSPFSIE LEDPQPPPDH IP,;
``` or the CD86 IgV domain:

```
                                                            (SEQ ID NO: 101)
  1   LKIQAYFNET ADLPCQFANS QNQSLSELVV FWQDQENLVL NEVYLGKEKF DSVHSKYMGR

61   TSFDSDSWTL RLHNLQIKDK GLYQCIIHHK KPTGMIRIHQ MNSELSVLA, .
```

Alternatively, an AD may comprise a sequence having at least 90% or at least 95% sequence identity with SEQ ID NOs: 100 or 101. An AD may also comprise a sequence having at least 96% or at least 98% sequence identity to at least 100 or 110 contiguous aas of SEQ ID NOs: 100 or 101.

An AD may comprise, for example, an aa sequence that binds the IL-12 as an agonist (e.g., IL-12 or an anti-CD28 scFv or nanobody aa sequence). An AD may comprise, for example, a single chain IL-12 that comprises the sequence:

1 IWELKKDVYV VELDWYPDAP GEMVVLTCDT PEEDGITWTL DQSSEVLGSG KTLTIQVKEF 61 GDAGQYTCHK GGEVLSHSLL LLHKKEDGIW STDILKDQKE PKNKTFLRCE AKNYSGRFTC 121 WWLTTISTDL TFSVKSSRGS SDPQGVTCGA ATL- SAERVRG DNKEYEYSVE CQEDSACPAA 181 EESLPIEVMV DAVHKLKYEN YTSSFFIRDI IKPDPPKNLQ LKPLKNSRQV EVSWEYPDTW 241 STPHSYFSLT FCVQVQGKSK REKKDRVFTD KTSAT- VICRK NASISVRAQD RYYSSSWSEW 301 ASVPCSGGGG SGGGGGGGG SRNLPVATPD PGMFPCLHHS QNLLRAVSNM LQKARQTLEF 361 YPCTSEEIDH EDITKDKTST VEACLPLELT KNES- CLNSRE TSFITNGSCL ASRKTSEMMA 421 LCLSSI- YEDL KMYQVEFKTM NAKLLMDPKR QIFLDQNMLA VIDELMQALN FNSETVPQKS 481 SLEEPDFYKT KIKLCILLHA FRIRAVTIDR VMSYLNAS (SEQ ID NO:90), which comprises a fragment of the p40 subunit, a linker repeat of GGGGS, and a fragment of the P35 subunit. Alternatively, an AD may comprise a sequence having at least 90% or at least 95% sequence identity with SEQ ID NO:90. An AD may also comprise a sequence having at least 96% or at least 98% sequence identity to at least 480 or 500 contiguous aas of SEQ ID NO:90.

As discussed above, the constructs of the present disclosure may comprise NBDs that heterodimerize in the presence of ATP. Accordingly, a complex between a first construct and a second construct that comprise heterodimerizing NBDs can be used to assemble an AD see, e.g., FIG. 2 at B and D). For example, an IL-12 AD may be formed in the presence of ATP by employing:
(i) a first construct comprising a p40 subunit (as a 1st immunomodulatory domain) comprising the sequence:
1 IWELKKDVYV VELDWYPDAP GEMVVLTCDT PEEDGITWTL DQSSEVLGSG KTLTIQVKEF 61 GDAGQYTCHK GGEVLSHSLL LLHKKEDGIW STDILKDQKE PKNKTFLRCE AKNYSGRFTC 121 WWLTTISTDL TFSVKSSRGS SDPQGVTCGA ATLSAERVRG DNKEYEYSVE CQEDSACPAA 181 EESLPIEVMV DAVHKLKYEN YTSSFFIRDI IKPDPPKNLQ LKPLKNSRQV EVSWEYPDTW 241 STPHSYFSLT FCVQVQGKSK REKKDRVETD KTSATVICRK NASISVRAQD RYYSSSWSEW 301 ASVPCS, (SEQ ID NO:91) or a sequence having at least 90% or at least 95% sequence identity with SEQ ID NO:91; and
(ii) a second construct comprising a p35 subunit (as a 2nd immunomodulatory domain) comprising the sequence:
1 RNLPVATPDP GMFPCLHHSQ NLLRAVSNML QKARQTLEFY PCTSEEIDHE DITKDKTSTV 061 EACLPLELTK NESCLNSRET SFITNGSCLA SRKTSEMMAL CLSSIYEDLK MYQVEFKTMN 121 AKLLMDPKRQ IFLDQNMLAV IDELMQALNF NSETVPQKSS LEEPDFYKTK IKLCILLHAF 181 RIRAVTIDRV MSYLNAS (SEQ ID NO:92), or a sequence having at least 90% or at least 95% sequence identity with SEQ ID NO:92.

An AD may comprise, for example, all or part of an aa sequence that binds to PD1 (e.g., an anti-PD1 scFv or nanobody aa sequence) or an aa sequence that binds to PDL1 (e.g., an anti-PDL1 scFv or nanobody aa sequence).

An AD may comprise, for example, an aa sequence that binds to CD40 (e.g., an anti-CD40 scFv or nanobody aa sequence or a CD40L aa sequence) or an aa sequence that binds to CD40L (e.g., an anti-CD40L scFv or nanobody aa sequence, or a CD40 aa sequence). A polypeptide that may be employed as an AD may comprise the CD40L aa sequence:

1 GDQNPQIAAH VISEASSKTT SVLQWAEKGY YTMSNNLVTL ENGKOLTVKR QGLYYIYAQV 61 TFCSNREASS QAPFIASLCL KSPGRFERIL LRAANTHSSA KPCGQQSIHL GGVFELQPGA 121 SVFVNVTDPS QVSHGTGFTS FGLLKL (SEQ ID NO:96), or an aa sequence having at least 90% or at least 95% sequence identity to SEQ ID NO:96. Alternatively, a polypeptide that may be employed as an AD comprises a trimer of CD40L aa sequences separated by linker sequences (e.g., linker sequences comprising GGGGS repeats):
1 GDQNPQIAAH VISEASSKTT SVLQWAEKGY YTMSNNLVTL ENGKOLTVKR QGLYYIYAQV 61 TFCSNREASS QAPFIASLCL KSPGRFERIL LRAANTHSSA KPCGQQSIHL GGVFELQPGA 121 SVFVNVTDPS QVSHGTGFTS FGLLKLGGGG SGGGGSGGGG SGDQNPQIAA HVISEASSKT 181 TSVLQWAEKG YYTMSNNLVT LENGKOLTUK RQGLYYIYAQ VTFCSNREAS SQAPFIASLC 241 LKSPGRFERI LLRAANTHSS AKPCGQQSIH LGGVFELQPG ASVFVNVTDP SQVSHGTGFT 301 SFGLLKLGGG GSGGGGSGGG GSGDQNPQIA AHVISEASSK 361 TTSVLQWAEK GYYTMSNNLV TLENGKOLTV KRQGLYYIYA QVTFCSNREA SSQAPFIASL CLK- SPGRFER ILLRAANTHS 421 SAKPCGQQSI HLGGVFELQP GASVFVNVTD PSQVSHGTGF TSFGLLKL (SEQ ID NO:95), or an aa sequence having at least 90% or at least 95% sequence identity to SEQ ID NO:95.

An AD may comprise, for example, an aa sequence that binds to CD137/4-1BB (e.g., an anti-CD137 scFv or nanobody aa sequence, or a CD137L/4-1BBL aa sequence), or an aa sequence that binds to TGFβ (e.g., an anti-TGFβ scFv or nanobody aa sequence, or a TGFBRII aa sequence). A polypeptide that may be employed as an AD may comprise the 4-1BBL aa sequence:
1 ACPWAVSGAR ASPGSAASPR LREGPELSPD DPAGLLDLRQ GMFAQLVAQN VLLIDGPLSW 61 YSDPGLAGVS LTGGLSYKED TKELVVAKAG VYYVFFQLEL RRVVAGEGSG SVSLALHLQP 121 LRSAAGAAAL ALTVDLPPAS SEARNSAFGF QGRLLHLSAG QRLGVHLHTE ARARHAWQLT 181 QGATVLGLER VTPEIPAGLP SPRSE (SEQ ID NO:94), or an aa sequence having at least 90% or at least 95% sequence identity to SEQ ID NO:94. Alternatively, a polypeptide that may be employed as an AD comprises a trimer of 4-1BBL aa sequences separated by linker sequences (e.g., linker sequences comprising GGGGS repeats):
1 ACPWAVSGAR ASPGSAASPR LREGPELSPD DPAGLLDLRQ GMFAQLVAQN VLLIDGPLSW 61 YSDPGLAGVS LTGGLSYKED TKELVVAKAG VYYVFFQLEL RRVVAGEGSG SVSLALHLQP 121 LRSAAGAAAL ALTVDLPPAS SEARNSAFGF QGRLLHLSAG QRLGVHLHTE ARARHAWQLT 181

QGATVLGLFR VTPEIPAGLP SPRSEGGGGS GGGGSGGGGS ACPWAVSGAR ASPGSAASPR 241 LREGPELSPD DPAGLLDLRQ GMFAQLVAQN VLLIDGPLSW YSDPGLAGVS LTGGLSYKED 301 TKELVVAKAG VYYVFFQLEL RRVVAGEGSG SVSLA- LHLQP LRSAAGAAAL ALTVDLPPAS 361 SEARN- SAFGF QGRLLHLSAG QRLGVHLHTE ARARHAWQLT QGATVLGLER VTPEIPAGLP 421 SPRSEGGGGS GGGGSGGGGS ACPWAVSGAR ASPGSAASPR LREG- PELSPD DPAGLLDLRQ 481 GMFAQLVAQN VLLIDG- PLSW YSDPGLAGVS LTGGLSYKED TKELVVAKAG VYYVFFQLEL 541 RRVVAGEGSG SVSLALHLQP LRSAAGAAAL ALTVDLPPAS SEARNSAFGF QGRLLHLSAG 601 QRLGVHLHTE ARARHAWQLT QGATVLGLER VTPEIPAGL PSPRSE (SEQ ID NO:93), or an aa sequence having at least 90% or at least 95% sequence identity to SEQ ID NO:93.

An AD may comprise, for example, an aa sequence that binds to IL-10 (e.g., an anti-IL-10 scFv or nanobody aa sequence) or an aa sequence that binds to IL-10R (e.g., an anti-IL-10R scFv or nanobody aa sequence).

An AD may comprise, for example, an aa sequence that binds to CD3 (e.g., an anti-CD3 scFv or nanobody aa sequence).

An AD may comprise, for example, an aa sequence that binds to CTLA-4 (e.g., an anti-CTLA-4 scFv or nanobody aa sequence).

An AD may comprise, for example, an aa sequence that binds to CD28 (e.g., an anti-CD28 scFv or nanobody aa sequence). An anti-CD28 scFv that may be used as an AD may comprise the sequence:

1 DIELTQSPAS LAVSLGQRAT ISCRASESVE YYVT- SLMQWY QQKPGOPPKL LIFAASNVES 61 GVPARFSGSG SGTNESLNIH PVDEDDVAMY FCQQSRKVPY TFGGGTKLEI KRGGGGSGGG 121 GSGGGGSQVK LQQSGPGLVT PSQSLSITCT VSGFSLSDYG VHWVRQSPGQ GLEWLGVIWA 181 GGGTNYNSAL MSRKSISKDN SKSQVELKMN SLQADDTAVY YCARDKGYSY YYSMDYWGQG 241 TTVTVSS (SEQ ID NO:89). Alternatively, an AD may comprise a sequence having at least 90% or at least 95% sequence identity with SEQ ID NO:89. An AD may also comprise a sequence having at least 96% or at least 98% sequence identity to at least 220 or 230 contiguous aas of SEQ ID NO:89.

An AD may comprise, for example, an interferon-γ (IFN-γ) polypeptide sequence, or an aa sequence that binds to the IFN-γ receptor (e.g., an anti-IFN-γ receptor scFv or nanobody aa sequence). A scIFN-γ polypeptide that may be employed as an IFN-γ AD may comprise the sequence:

1 MQDPYVKEAE NLKKYFNAGH SDVADNGTLF LGILKNWKEE SDRKIMQSQI VSFYFKLFKN 61 FKDDQSIQKS VETIKEDMNV KFFNSNKKKR DDFEKLTNYS VTDLNVQRKA IDELIQVMAE 121 FSTEEQQEGP YVKEAENLKK YFNAGHSDVA DNGTLFLGIL KNWKEESDRK IMQSQIVSFY 181 FKLFKNFKDD QSIQKSVETI KEDMNVKFEN SNKKKRDDFE KLTNYSVTDL NVQRKAIHEL 241 IQVMAELSPA AKTGKRKRSQ MLFRG (SEQ ID NO:97). Alternatively, an AD may comprise a sequence having at least 90% or at least 95% sequence identity with SEQ ID NO:97. An AD may also comprise a sequence having at least 96% or at least 98% sequence identity to at least 220 or 230 contiguous aas of SEQ ID NO:97.

An AD may comprise, for example, an aa sequence that binds to CD16 (e.g., an anti-CD16 scFv or nanobody aa sequence). Anti-CD16 VHH polypeptides that may be employed as an AD may comprise one of:

1 EVOLVESGGG LVQPGESLTL SCVVAGSIFS FAM- SWYRQAP GKERELVARI GSDDRVTYAD 61 SVKGRFTISR DNIKRTAGLQ MNSLKPEDTA VYYCNAQTDL RDWTVREYWG QGTQVTVSS (SEQ ID NO:98); or

1 EVOLVESGGE LVQPGGSLRL SCAASGLTFS SYN- MGWERRA PGKEREFVAS ITWSGRDTFY 61 ADSVKGRFTI SRDNAKNTVY LQMSSLKPED TAVYY- CAANP WPVAAPRSGT YWGQGTQVTV 121 SS (SEQ ID NO:103). Alternatively, an AD may comprise a sequence having at least 90% or at least 95% sequence identity with SEQ ID NOs:98 or 103. An AD may also comprise a sequence having at least 96% or at least 98% sequence identity to at least 100 or 110 contiguous aas of SEQ ID NOs:98 or 103.

ADs do not have to be comprised of an aa sequence, and may, for example, be comprised of nucleic acid sequences. Non-limiting examples of nucleic acid ADs include nucleic acid sequences with CpG repeats (e.g., a CpG oligodeoxynucleotide sequence) or IMT504 (TCATCATTTTGTCAT-TTTGTCATT (SEQ ID NO:69, see, e.g., Insula et al., 2007 Stem Cells, 25:1047-1054) optionally having 1, 2 or 3 nucleotide substitutions, deletions, or insertions.

6 Tumor-Specific Binding Domains

A tumor-specific binding domain of the constructs described herein (also referred to as tumor-specific binder, or "TSB") is a polypeptide aa sequence that functions as a targeting sequence directing the construct to tumor cells by binding to target molecules expressed on the tumor cell surface. The target molecules may be a tumor-associated antigen ("TAA") (also referred to herein as a cancer associated antigen or "CAA") whose cell surface expression is restricted, or substantially restricted, to one or more cancer cell types. In addition to molecules whose expression is restricted or substantially restricted to tumor cells, other molecules present on a tumor cell's surface may be targeted including, but not limited to, cell proteins expressed on normal (non-transformed) cells, which may be upregulated in the tumor cell. Checkpoint proteins (e.g., V-domain Ig suppressor of T cell activation or "VISTA", T-cell immunoglobulin and mucin domain 3 or "Tim-3", and Programmed Death Ligand 1 or "PD-L1"), which are expressed on normal and many tumor cells (e.g., transformed tumor cells), may also serve as target molecules for TSBs. Targeting checkpoint proteins, which are often upregulated by tumor cells as a means of immune evasion or escape, both offers a target that may be abundantly expressed on the tumor cell's surface and provides checkpoint inhibition by the TSB. Proteins not substantially restricted to expression on transformed tumor cells are considered as targets of TSBs when expressed on tumor cells. They are considered targets of TSBs because any immune response directed by the TSB is limited to the TME where ATP levels are sufficiently high to permit pairing or complexation of the TSB to an AD or immune cell engager and through the NBDs coupled to those elements (see, e.g., FIGS. 3, 4A, and 4B). TSBs include, for example, polypeptides and other molecules such as antibodies, antigen binding fragments of an antibody, Fabs, Fab's, and polypeptides comprising single chain antibody, scFv, peptide aptamer, or nanobody aa sequences.

Some TAAs associated with a solid tumor that may be targeted by TSBs include, but are not limited to: carbonic anhydrase IX (CAIX), cadherins, carcinoembryonic antigen (CEA), cellular-mesenchymal epithelial transition factor (c-MET), Cytotoxic T-Lymphocyte Associated Protein 4

(CTLA-4), Epidermal Growth Factor Receptor (EGFR) family members, Epithelial Cell Adhesion Molecule (Ep-CAM), Ephrin Type-A Receptor 3 (EphA3), Fibroblast Activation Protein Alpha (FAP), folate-binding protein, Folate Receptor alpha (FR-alpha), Erb-B2 Receptor Tyrosine Kinase 2 (HER2), Erb-B2 Receptor Tyrosine Kinase 3 (HER3), Insulin Like Growth Factor 1 Receptor (IGF-1R), integrin αVβ3, integrin α5β1, Solute Carrier Family 39 Member 6 (Liv1), a Melanoma-Associated Antigen family A member (MAGEA), a Melanoma-Associated Antigen family C member (MAGEC), mesothelin, a mucin (e.g., MUC1), a New York Esophageal Squamous Cell Carcinoma 1 protein (NY-ESO-1, Cancer/Testis Antigen 1A, Cancer/Testis Antigen 1B), Cancer/Testis Antigen 2 (NY-ESO-2, CTAG2), Prostate-Specific Membrane Antigen (PSMA), Receptor Activator of Nuclear Factor Kappa B Ligand (RANKL), Receptor Tyrosine Kinase Like Orphan Receptor 1 (ROR1), tenascin, TNF Receptor Superfamily Member 10a (TRAILR1), TNF Receptor Superfamily Member 10b (TRAILR2), and Vascular Endothelial Growth Factor Receptor (VEGFR).

Some TAAs associated with a solid tumor that may be targeted by TSBs include, but are not limited to: Cancer/Testis Antigen 1A, Cancer/Testis Antigen 1B, or Cancer/Testis Antigen 2 (NY-ESO-2, CTAG2), Some TAAs associated with a solid tumor that may be targeted by TSBs include, but are not limited to: MAGEA-1, MAGEA-4, or MAGEA-9.

Some TAAs associated with a solid tumor that may be targeted by TSBs include, but are not limited to: MAGEC-1, MAGEC-2, or MAGEC-3.

Some checkpoint proteins that may serve as targets of TSBs include, but are not limited to, VISTA, TIM-3, PD-L1, CTLA-4, and LAG-3.

A TSB polypeptide may be an anti-human mesothelin scFv polypeptide related to the murine-derived SS1 antibody, also employed in Amatuximab having the sequence: QVQLQQSGPELEKPGASVKISCKASGYSFTGY TMNWVKQSHGKSLEWIGLITPYNGASSYN-QKFRGKATLTVDKSSSTAYMDLLSLTSED-SAVYFCARGGYD GRGFDYWGSGTPVTVSSGXGGSGGGGSGGGGSDIEL TQSPAIMSASPGEKVTMTCSASSSVSYMHWYQQK SGTSPKRWIYDTSKLASGVPGRFSGSGSGNSYS-LTISSVEAEDDATYYCQQWSKHPLTFGSGTKVEIK, where X is V or G (SEQ ID NO:70). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human mesothelin scFv (vH-vL) polypeptide related to the monoclonal antibody YP218, having the sequence: QEQLVESGG-GLVQPGASLTLTCTASGIDESRYYMCWVRQ APGKG-LEGIACIYIGGSGSTYYAS-WAKGRFTISKASSTTVTLQMTSLTAADTATYFCARGT NLNYIFRLW GPGTLVTVSSGXGGSGGGGSGGGGSDVVMTQT-PASVSEPVGGTVTIKCQASQRIS-SYLSWYQQKPGQRPK LLIFGAST-LASGVPSRFKGSGSGTEYTLTISDLECADAATYYCQS YAYFDSNNWHAFGGGTEVVV, where X is V or G (SEQ ID NO:71). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human mesothelin scFv (vL-vH) polypeptide related to the monoclonal antibody YP218, having the sequence: DVVMTQT-PASVSEPVGGTVTIKCQASQRISSYLSWYQQK PGQRPKLLIFGAST-LASGVPSRFKGSGSGTEYTLTISDLEC-ADAATYYCQSYAYFDSNNWHAFGGGTEVV VGXGGSGGGGSGGGGSQEQLVESGGGLVQP-GASLTLTCTASGIDFSRYYMCWVRQAPGKGLEGI-ACIYIG GSGSTYYASWAKGRFTISKASSTTVTLQMT-SLTAADTATYFCARGTNLNYIFRLWGPGTLVTVSS, where X is V or G (SEQ ID NO:72). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human mesothelin scFv (vH-vL) polypeptide related to the monoclonal antibody 15B6, having the sequence: EVQLQQSGPVLVKPGASVKISCK-ASGYSFTGYYMHWVRQS NGKSLEWIGRINPY-TGVPSYKHNFKDKASLTVDKSSSTAYMELHSLTSED-SAVYYCARELGGYWGQGTTL TVSSGXGGSGGGGSGGGGSQAVVTQESALTT-SPGETVTLTCRSST-GAVTTGNYPNWVQEKPDHLFTGLIA GTNNRAPGV-PARESGSLIGDKAALTITGAQTEDEAIYFCALWFSSHW VFGGGTKLTVLG, where X is V or G (SEQ ID NO:73). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human mesothelin scFv (vL-vH) polypeptide related to the monoclonal antibody 15B6, having the sequence: PDHLFTGLI-AGTNNRAPGVPARFSGSLIGDKAALTITGAQ TEDEAIYFCALWFSSH-WVFGGTKLTVLGGXGGSGGGGSGGGG-SEVQLQQSGPVLVKPGASVKISCKASG YSFTGYYMHWVRQSNGKSLEWIGRINPY-TGVPSYKHNFKDKASLTVDKSSSTAYMELHSLTSED-SAVYYC ARELGGYWGQGTTLTVSS, where X is V or G (SEQ ID NO:74). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human mesothelin scFv (vL-vH) polypeptide related to the monoclonal antibody 15B6 with a disulfide linkage between the vL and vH positions G102C and K43C (K 168C as shown), having the sequence: QAVVTQESALTTSPGETVTLTCRSST-GAVTTGNYPNWVQEKPDHLFTGLIA GTNN-RAPGVPARFSGSLIGDKAALTITGAQT-EDEAIYFCALWFSSHWVFGCGTKLTVLGGGGGSGG GGSG GGGSEVQLQQSGPVLVKPGASVKISCK-ASGYSFTGYYMHWVRQSNGCSLEWIGRINPY-TGVPSYKHNEKD KASLTVDKSSSTAYMELHSLTSED-SAVYYCARELGGYWGQGTTLTVSS (SEQ ID NO:75). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human mesothelin scFv (vL-vH) polypeptide related to the monoclonal antibody 15B6 with a disulfide linkage between the vL and vH positions G102C and S44C (S169C as shown), having the sequence: QAVVTQESALTTSPGETVTLTCRSSTGAVTTGNYPNWVQEKPDHLFTGLIA GTNNRAPGVPARFSGSLIGDKAALTITGAQTEDEAIYFCALWFSSHWVFGCGTKLTVLGGGGGSGGG GSG GGGSEVQLQQSGPVLVKPGASVKISCKASGYSFTGYYMHWVRQSNGKCLEWIGRINPYTGVPSYKHNEKD KASLTVDKSSSTAYMELHSLTSEDSAVYYCARELGGYWGQGTTLTVSS (SEQ ID NO:76). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human mesothelin scFv (vL-vH) polypeptide related to the monoclonal antibody 15B6 with a disulfide linkage between the vL and vH positions G103C and K43C (K168C as shown), having the sequence: QAVVTQESALTTSPGETVTLTCRSSTGAVTTGNYPNWVQEKPDHLFTGLIA GTNNRAPGVPARFSGSLIGDKAALTITGAQTEDEAIYFCALWFSSHWVFGGCTKLTVLGGGGGSGG GGSG GGGSEVQLQQSGPVLVKPGASVKISCKASGYSFTGYYMHWVRQSNGCSLEWIGRINPYTGVPSYKHNFKD KASLTVDKSSSTAYMELHSLTSEDSAVYYCARELGGYWGQGTTLTVSS (SEQ ID NO:77). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human mesothelin scFv (vL-vH) polypeptide related to the monoclonal antibody 15B6 with a disulfide linkage between the vL and vH positions G103C and S44C (S169C as shown), having the sequence: QAVVTQESALTTSPGETVTLTCRSSTGAVTTGNYPNWVQEKPDHLFTGLIA GTNNRAPGVPARFSGSLIGDKAALTITGAQTEDEAIYFCALWFSSHWVFGGCTKLTVLGGGGGSGG GGSG GGGSEVQLQQSGPVLVKPGASVKISCKASGYSFTGYYMHWVRQSNGKCLEWIGRINPYTGVPSYKHNFKD KASLTVDKSSSTAYMELHSLTSEDSAVYYCARELGGYWGQGTTLTVSS (SEQ ID NO:78). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB binder polypeptide may comprise an anti-human mesothelin (VHH) polypeptide related to the monoclonal antibody SD1, having the sequence: QVQLVQSGGGLVQPGGSLRLSCAASDEDFAAYEMSWVRQA PGQGLEWVAIISHDGIDKYYTDSVKGRFTISRDNSKNTLYLQMNTLRAEDTATYYCLRLGAVGQGTLVTV SSS (SEQ ID NO:79). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human EpCAM scFv (vH-vL) polypeptide related to the monoclonal antibody MT201 and Adecatumumab, having the sequence: EVQLLESGGGVVQPGRSLRLSCAASG FTFSSYGMHWVRQAPGKGLEWVAVISYDGSNKYYADSVKGRFTISRDNSKNTLYLQMNSLRAEDTAVYYC AKDMGWGSGWRPYYYYGMDVWGQGTTVTVSSG XGGSGGGGSGGGGSELQMTQSPSSLSASVGDRVTITCR TSQSISSYLNWYQQKPGQPPKLLIYWASTRESGVPDRFSGSGSGTDFTLTISSLQPEDSATYYCQQS YDI PYTFGQGTKLEIKRTV, where X is V or G (SEQ ID NO:80). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human EpCAM scFv (vL-vH) polypeptide related to the monoclonal antibody MT201 and Adecatumumab, having the sequence: ELQMTQSPSSLSASVGDRVTITCRTS QSISSYLNWYQQKPGQPPKLLIYWASTRESGVPDRFSGSGSGTDFTLTISSLOPEDSATYYCQQSYDIPY TFGQGTKLEIKRTVGXGGSGGGGSGGGGSEVQLLESGGGVVQPGRSLRLSCAASGFTFSSYGMHWVRQAP GKGLEWVAVISYDGSNKYYADSVKGRFTISRDNSKNTLYLQMNSLRAEDT AVYYCAKDMGWGSGWRPYYY YGMDVWGQGTTVTVSS, where X is V or G (SEQ ID NO:81). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human CTLA-4 scFv (vL-vH) polypeptide related to Ipilimumab, having the sequence: EIVLTQSPGTLSLSPGERATLSCRASQSVGSSYLAWYQQKPGQAPRLLIYGAFSRAT GIPDRFSGSGSGTDFTLTISRLEPEDFAVYYCQQYGSSPWTFGQGTKVEIKRGGGGSGGGG SGGGGSQVQ LVESGGGVVQPGRSLRLSCAASGFTFSSYTMHWVRQAPGKGLEWVTFISYDGNNKYYADSVKGRFTISRD NSKNTLYLQMNSLRAEDTAIYYCARTGWLGPFDYWGQGTLVTVSS (SEQ ID NO:82). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human CTLA-4 scFv (vL-vH) polypeptide related to Ipilimumab with a disulfide linkage between the vL and vH positions Q101C and K43C (K 167C as shown), having the sequence: EIVLTQSPGTLSLSPGERATLSCRASQSVGSSYLAWYQQKPGQAPRLLIYGAFSRATGIPDRESGSGSGT DETLTISRLEPEDFAVYYCQQYGSSPWTFGCGTKVEIKRGGGGSGGGGS GGGGSQVQLVESGGGVVQPGR SLRLSCAASGFTFSSYTMHWVRQAPGCGLEWVTFISYDGNNKYYADSVKGRFTISRDNSKNTLYLQMNSL RAEDTAIYYCARTGWLGPFDYWGQGTLVTVSS (SEQ ID NO:83). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human CTLA-4 scFv (vL-vH) polypeptide related to Ipilimumab with a disulfide linkage between the vL and vH positions Q101C and G44C (G167C as shown), having the sequence: IVLTQSPGTLSLSPGERATLSCRASQSVGSSY-LAWYQQKPGQAPRLLIYGAFSRATGIEPDRFSGSGS GT DETLTISRLEPED-FAVYYCQQYGSSPWTFGCGTKVEIKRGGGGSGGGGS GGGGSQVQLVESGGGVVQPGR SLRLSCAASGFTFS-SYTMHWVRQAPGKCLEWVTFISYDGNNKYY-ADSVKGRFTISRDNSKNTLYLQMNSL RAEDTAIYY-CARTGWLGPFDYWGQGTLVTVSS (SEQ ID NO:84). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

A TSB polypeptide may comprise an anti-human CTLA-4 scFv (vL-vH) polypeptide related to Ipilimumab with a disulfide linkage between the vL and vH positions G102C and K43C (K167C as shown), having the sequence: EIVLTQSPGTLSLSPGERATLSCRASQSVGSSY-LAWYQQKPGQAPRLLIYGAFSRATGIPDRESGSGSGT DFTLTISRLEPED-FAVYYCQQYGSSPWTFGQCTKVEIKRGGGGSGGGGS GGGGSQVQLVESGGGVVQPGR SLRLSCAASGFTFS-SYTMHWVRQAPGCGLEWVTFISYDGNNKYY-ADSVKGRFTISRDNSKNTLYLQMNSL RAEDTAIYY-CARTGWLGPFDYWGQGTLVTVSS (SEQ ID NO:85). The tumor-specific binder polypeptide may also comprise an aa sequence having greater than 90% or greater than 95% sequence identity to that sequence. Alternatively, the tumor-specific binder polypeptide may comprise an aa sequence having greater than 96% or greater than 98% sequence identity to that sequence.

A TSB polypeptide may comprise an anti-human CTLA-4 scFv (vL-vH) polypeptide related to Ipilimumab with a disulfide linkage between the vL and vH positions G102C and G44C (G168C as shown), having the sequence: EIVLTQSPGTLSLSPGERATLSCRASQSVGSSY-LAWYQQKPGQAPRLLIYGAFSRATGIPDRESGSGSGT DETLTISRLEPED-FAVYYCQQYGSSPWTFGQCTKVEIKRGGGGSGGGGS GGGGSQVQLVESGGGVVQPGR SLRLSCAASGFTFS-SYTMHWVRQAPGKCLEWVTFISYDGNNKYY-ADSVKGRFTISRDNSKNTLYLQMNSL RAEDTAIYY-CARTGWLGPFDYWGQGTLVTVSS (SEQ ID NO:86). The TSB polypeptide may also comprise an aa sequence having greater than 90% or greater than 95% sequence identity to that sequence. Alternatively, the TSB polypeptide may comprise an aa sequence having greater than 96% or greater than 98% sequence identity to that sequence.

The linker sequences in SEQ ID NOs:70-86 are bolded and italicized.

E. Methods of Preparation

The present disclosure includes and provides for the preparation of the constructs disclosed herein by transcription and translation of nucleic acids encoding the constructs in mammalian cells (CHO cells), yeast cells (e.g., pica pastoris), sodoptera cells, or bacterial cells (e.g., *E. coli* cells). Portions of the constructs may also be prepared separately, such as by cellular expression as discussed above, chemical synthesis, etc., and then conjugated together using one or more chemical or enzymatic processes. Indeed, enzymatic means, self-catalyzed protein splicing, or chemical crosslinking (e.g., with a heterobifunctional cross-linker) can be used to couple (e.g. covalently attach), for example, ADs to NBDs, TSBs to NBDs, and/or NBDs to immune cell engagers. Where the components to be coupled are both comprised of aa sequences, enzymatic means and self-catalyzed protein splicing represent coupling options that permit both the stoichiometry and structure of the coupling reaction, while substantially avoiding potential secondary coupling reactions. For example, sortases and split inteins may be utilized to append a sequence comprising a NBD to an AD, a TSB binder, or an immune cell engager. See, e.g., Bhagawati et al., *Proc Natl Acad Sci USA*, 116(44):22164-22172 (2019). Alternatively, the enzyme catalyzed SpyTag/SpyCatcher system, which may employ the CnaB2 domain of the FbaB protein from *Streptococcus pyogenes*, can be utilized for conjugating an AD to a polypeptide comprising a NBD. See, e.g., Reddington and Howarth, *Curr. Opin in Chem. Biol.*, 29: 94-99 (2015).

In addition to pure enzymatic and chemical conjugation methods for coupling components of the constructs described herein, affinity guided methods that combine the specificity of protein-protein interactions with chemical conjugation may be employed. Affinity guided chemical conjugations offer efficient, facile, and specific chemical conjugation reactions. One such method, PEptide-Directed Photo-cross-linking (PEDIP) has been described by Park et al. (2018), Bioconjug Chem., 29:3240-3244, and demonstrated for coupling polypeptides to antibody heavy chain constant regions. See also Kishomoto et al., (2019), Bioconjug Chem., 30(3):697-702.

Where the AD is not an aa sequence that can be translated in a biological system (e.g., it is a nucleic acid such as a CpG oligodeoxynucleotide), it may be coupled to the other portions of the molecule using, for example, bifunctional cross-linkers (e.g., homobifunctional or heterobifunctional cross-linkers).

The constructs may be purified using a variety of methods known in the art. For example, where the construct comprises an IgFc region as a scaffold, it may be purified by protein A or protein G chromatography. The constructs may be purified by nucleotide affinity chromatography or dye-ligand affinity chromatography using Cibacron Blue F3GA, Procion Blue HB, or Reactive blue 2 as affinity ligands. Size exclusion chromatography may also be used alone or in combination with affinity chromatography to purify the products.

F. Formulations and Methods of Treatment

The NBD-containing constructs and complexes disclosed herein (see, e.g., FIGS. 2-4) may be formulated into compositions comprising pharmaceutically acceptable components.

The compositions may be prepared for parenteral and/or other forms of administration. The constructs or compositions comprising the constructs may be administered by any suitable route, such as intravenously, intramuscularly, subcutaneously, intratumorally, or intralymphatically. The constructs may also be administered in conjunction with one or more other agents that act synergistically or non-synergistically with the constructs. For example, constructs of the present disclosure (e.g., those with IL-12 activating domains) may be administered with immune checkpoint inhibitors such as Pembrolizumab (Keytruda®, targeting PD-1), Avelumab (Bavencio®, targeting PD-L1), or Ipilimumab (Yervoy®, targeting CTLA-4).

Any solid tumor that contains elevated levels of ATP relative to normal tissue may be treated utilizing the constructs of the present disclosure. Treatable tumors include mesotheliomas, melanomas, sarcomas, carcinomas, carcinosarcomas, lymphomas, and germ cell tumors. Representative carcinomas include, but are not limited to, colorectal carcinoma, breast carcinoma, neuroendocrine tumors, lung carcinoma, and gastric carcinoma. For example, the tumors may be lung, liver, skin, gastrointestinal, pancreatic, brain, or reproductive tissue (e.g., ovarian sarcomas) tumors.

VI. ASPECTS

1. A polypeptide construct comprising a nucleotide binding domain (NBD) amino acid (aa) sequence, and an activating domain (AD) aa sequence, optionally joined by a linker peptide sequence; wherein the NBD comprises one or more adenosine triphosphate (ATP) binding sites and can homodimerize or heterodimerize with a cognate non-identical NBD in the presence of ATP (e.g., the NBD of TAP1 or TAP2 which can heterodimerize).
2. The polypeptide construct of aspect 1, wherein the construct is organized in the N-terminal to C-terminal direction as (i) NBD, optional linker, and AD aa sequences, or (ii) AD, optional linker, and NBD aa sequences.
3. The polypeptide construct of aspect 1 or 2, comprising a NBD aa sequence, scaffold aa sequence, and AD sequence optionally joined by independently selected linker aa sequences.
4. The polypeptide construct of aspect 3, wherein the construct comprises in the N-terminal to C-terminal direction the NBD, scaffold, and AD aa sequences.
5. The polypeptide construct of aspect 3, wherein the construct comprises in the N-terminal to C-terminal direction the NBD, AD, and scaffold aa sequences.
6. The polypeptide construct of aspect 3, wherein the construct comprises in the N-terminal to C-terminal direction, the AD, scaffold, and NBD aa sequences.
7. The polypeptide construct of aspect 3, wherein the construct comprises in the N-terminal to C-terminal direction, the AD, NBD, and scaffold aa sequences.
8. The polypeptide construct of aspect 3, wherein the construct comprises in the N-terminal to C-terminal direction, the scaffold, AD, and NBD aa sequences.
9. The polypeptide construct of aspect 3, wherein the construct comprises in the N-terminal to C-terminal direction, the scaffold, NBD, and AD aa sequences.
10. The polypeptide construct of any one of aspects 1-9, comprising two or more (e.g., three or more) independently selected AD aa sequences, wherein the AD aa sequences are optionally placed in tandem.
11. The polypeptide construct of any one of aspects 1-10, comprising two or more (e.g., three or more) independently selected NBD aa sequences, optionally placed in tandem (constrained so that no two NBDs within the same molecule can interact to form a complex in the presence of ATP).
12. The polypeptide construct of aspect 11, further comprising a rigid linker that substantially prevents interactions between the two or more NBD aa sequences in the presence of ATP.
13. The polypeptide construct of any one of aspects 1-12, wherein each NBD aa sequence may homodimerize in the presence of ATP (e.g. comprises an identical homodimerizing aa sequence).
14. The polypeptide construct of aspect 13, wherein the construct comprises a NBD (e.g., a single NBD) aa sequence. See e.g., FIG. 2 at A, C, and E.
15. The polypeptide construct of aspect 11 or 12, comprising two or more NBD aa sequences that may homodimerize to form a dimer or higher order complex of the construct in the presence of ATP. See, e.g., FIG. 4A at A.
16. The polypeptide construct of any of aspects 13-15, wherein each NBD aa sequence comprises an identical or substantially identical homodimerizing aa sequence.
17. The polypeptide construct of any one of aspects 1-12, wherein each NBD aa sequence may heterodimerize with a cognate NBD in the presence of ATP.
18. The polypeptide construct of aspect 17, wherein the construct comprises a NBD (e.g., a single NBD) aa sequence (see, e.g., each of the constructs in FIG. 2 at B and D), or one or more (e.g., two or more) NBD aa sequences.
19. A composition comprising a first polypeptide construct and a second polypeptide construct of any of aspects 13-18, wherein the first polypeptide construct comprises a first NBD aa sequence and the second polypeptide construct comprises a second NBD aa sequence, and the first and second NBD aa sequences are cognate sequences that may homodimerize or heterodimerize in the presence of ATP to form a homodimer or heterodimer complex. See, e.g., FIG. 2 at B and D.
20. A composition comprising the first polypeptide construct and the second polypeptide construct of aspect 19, wherein the first polypeptide construct comprises one or more (e.g., two or more) first NBD aa sequences and the second polypeptide construct comprises one or more (e.g., two or more) second NBD aa sequences, and the first and second NBD aa sequences are cognate sequences that may homodimerize or heterodimerize in the presence of ATP to form a homodimer, heterodimer or higher order complex. See, e.g., FIG. 2 at B and D where each construct comprises a NBD (e.g., a single NBD) aa sequence, and FIG. 4A at B wherein at least one of the first and second (e.g., both) constructs comprises two or more NBD aa sequences.
21. A polypeptide construct comprising a nucleotide binding domain (NBD) amino acid (aa) sequence, and tumor-specific binder (TSB) aa sequence, optionally joined by a linker peptide sequence wherein: the NBD comprises one or more adenosine triphosphate (ATP) binding sites and can homodimerize or heterodimerize with a cognate non-identical NBD in the presence of ATP (e.g., the NBD of TAP1 or TAP2 which can heterodimerize); and wherein the polypeptide construct optionally comprises one or more ADs.
22. The polypeptide construct of aspect 21, wherein the construct is organized in the N-terminal to C-terminal direction as (i) NBD, optional linker, and TSB aa sequences, or (ii) TSB, optional linker, and NBD aa sequences.
23. The polypeptide construct of aspect 21 or 22, comprising a NBD aa sequence, a scaffold aa sequence, and a TSB aa sequence optionally joined by independently selected linker aa sequences.

24. The polypeptide construct of aspect 23, wherein the construct comprises in the N-terminal to C-terminal direction the NBD, scaffold, and TSB aa sequences.
25. The polypeptide construct of aspect 23, wherein the construct comprises in the N-terminal to C-terminal direction the NBD, TSB, and scaffold aa sequences.
26. The polypeptide construct of aspect 23, wherein the construct comprises in the N-terminal to C-terminal direction, the TSB, scaffold, and NBD aa sequences.
27. The polypeptide construct of aspect 23, wherein the construct comprises in the N-terminal to C-terminal direction, the TSB, NBD, and scaffold aa sequences.
28. The polypeptide construct of aspect 23, wherein the construct comprises in the N-terminal to C-terminal direction, the scaffold, TSB, and NBD aa sequences.
29. The polypeptide construct of aspect 23, wherein the construct comprises in the N-terminal to C-terminal direction, the scaffold, NBD, and TSB aa sequences.
30. The polypeptide construct of any one of aspects 21-29, comprising two or more (e.g., three or more) independently selected TSB aa sequences, wherein the TSB aa sequences are optionally placed in tandem.
31. The polypeptide construct of any one of aspects 21-30, comprising two or more (e.g., three or more) independently selected NBD aa sequences, optionally placed in tandem (constrained so that no two NBDs within the same molecule can interact to form a complex in the presence of ATP).
32. The polypeptide construct of aspect 31, further comprising a rigid linker that substantially prevents interactions between the two or more NBD aa sequences in the presence of ATP.
33. The polypeptide construct of any one of aspects 21-32, wherein each NBD aa sequence may homodimerize in the presence of ATP (e.g. comprises an identical homodimerizing aa sequence).
34. The polypeptide construct of aspect 33, wherein the construct comprises a NBD (e.g., a single NBD) aa sequence. See e.g., FIG. 4B at A-D.
35. The polypeptide construct of aspect 31 or 32, comprising two or more NBD aa sequences that may homodimerize to form a dimer or higher order complex of the construct in the presence of ATP. See, e.g., FIG. 4A at C.
36. The polypeptide construct of aspect 35, wherein each NBD aa sequence comprises an identical or substantially identical homodimerizing aa sequence.
37. The polypeptide construct of any one of aspects 21-32, wherein each NBD aa sequence may heterodimerize with a cognate NBD in the presence of ATP.
38. The polypeptide construct of aspect 37, wherein the construct comprises a NBD (e.g., a single NBD) aa sequence, or one or more (e.g., two or more) NBD aa sequences.
39. A composition comprising a first polypeptide construct and a second polypeptide construct of any of aspects 33-38, wherein the first polypeptide construct comprises a first NBD aa sequence and the second polypeptide construct comprises a second NBD aa sequence, and the first and the second NBD aa sequences are cognate sequences that may homodimerize or heterodimerize in the presence of ATP to form a homodimer or heterodimer complex.
40. A composition comprising the first polypeptide construct and the second polypeptide construct of aspect 39, wherein the first polypeptide construct comprises one or more (e.g., two or more) first NBD aa sequences and the second polypeptide construct comprise one or more (e.g., two or more) second NBD aa sequences, and the first and second NBD aa sequences are cognate sequences that may homodimerize or heterodimerize in the presence of ATP to form a homodimer or heterodimer or higher order complex.
41. The composition of aspect 39 or aspect 40, wherein the TSB of the first polypeptide construct and the TSB of the second polypeptide construct recognize a single tumor-associated antigen (TAA) or different (non-identical) TAAs.
42. A polypeptide construct comprising a nucleotide binding domain (NBD) amino acid (aa) sequence, and an immune cell engager (ICE) aa sequence, optionally joined by a linker peptide sequence wherein: the NBD comprises one or more adenosine triphosphate (ATP) binding sites and can homodimerize or heterodimerize with a cognate non-identical NBD in the presence of ATP (e.g., the NBD of TAP1 or TAP2 which can heterodimerize); and wherein the polypeptide construct optionally comprises one or more ADs.
43. The polypeptide construct of aspect 42, wherein the construct is organized in the N-terminal to C-terminal direction as (i) NBD, optional linker, and ICE aa sequences, or (ii) ICE, optional linker, and NBD aa sequences.
44. The polypeptide construct of aspect 42 or 43, comprising a NBD aa sequence, scaffold aa sequence, and ICE aa sequence optionally joined independently by selected linker aa sequences.
45. The polypeptide construct of aspect 43, wherein the construct comprises in the N-terminal to C-terminal direction the NBD, scaffold, and ICE aa sequences.
46. The polypeptide construct of aspect 43, wherein the construct comprises in the N-terminal to C-terminal direction the NBD, ICE, and scaffold aa sequences.
47. The polypeptide construct of aspect 43, wherein the construct comprises in the N-terminal to C-terminal direction, the ICE, scaffold, and NBD aa sequences.
48. The polypeptide construct of aspect 43, wherein the construct comprises in the N-terminal to C-terminal direction, the ICE, NBD, and scaffold aa sequences.
49. The polypeptide construct of aspect 43, wherein the construct comprises in the N-terminal to C-terminal direction, the scaffold, ICE, and NBD aa sequences.
50. The polypeptide construct of aspect 43, wherein the construct comprises in the N-terminal to C-terminal direction, the scaffold, NBD, and ICE aa sequences.
51. The polypeptide construct of any one of aspects 42-50, comprising two or more (e.g., three or more) independently selected ICE aa sequences, wherein the ICE aa sequences are optionally placed in tandem.
52. The polypeptide construct of any one of aspects 42-51, comprising two or more (e.g., three or more) independently selected NBD aa sequences, optionally placed in tandem (constrained so that no two NBDs within the same molecule can interact to form a complex in the presence of ATP).
53. The polypeptide construct of aspect 52, further comprising a rigid linker that substantially prevent interactions between the two or more NBD aa sequences in the presence of ATP.
54. The polypeptide construct of any one of aspects 42-53, wherein the each NBD aa sequence may homodimerize in the presence of ATP (e.g. comprises an identical homodimerizing aa sequence).

55. The polypeptide construct of aspect 54, wherein the construct comprises a NBD (e.g., a single NBD) aa sequence. See e.g., FIG. 4A at D.
56. The polypeptide construct of aspect 53 or 54, comprising two or more NBD aa sequences that may homodimerize to form a dimer or higher order complex of the construct in the presence of ATP.
57. The polypeptide construct of any one of aspects 42-53, wherein the each NBD aa sequence may heterodimerize with a cognate NBD in the presence of ATP.
58. The polypeptide construct of aspect 57, wherein the construct comprises a NBD (e.g., a single NBD) aa sequence, or one or more (e.g., two or more) NBD aa sequences.
59. A composition comprising a first polypeptide construct and a second polypeptide construct of aspect 58, wherein the construct comprises a first NBD aa sequence and a second polypeptide construct comprise a second NBD aa sequence, and the first and the second NBD aa sequences are cognate sequences that may heterodimerize in the presence of ATP to form a heterodimer complex.
60. A composition comprising the first polypeptide construct and the second polypeptide construct of aspect 59, wherein the first polypeptide construct comprises one or more (e.g., two or more) first NBD aa sequences and the second polypeptide construct comprise one or more (e.g., two or more) second NBD aa sequences, and the first and second NBD aa sequences are cognate sequences that may heterodimerize in the presence of ATP to form a heterodimer or higher order complex.
61. The composition of aspect 59 or aspect 60, wherein the ICE of the first polypeptide construct and the ICE of the second polypeptide construct recognize a single immune cell surface molecule or different (non-identical) immune cell surface molecules.
62. A composition comprising a first polypeptide construct of any one of aspects 1-18, and a second polypeptide construct of any one of aspects 42-58, wherein:
    (i) the first polypeptide construct comprises one or more (e.g., two or more) first heterodimerizing NBD aa sequences and the second polypeptide construct comprises one or more (e.g., two or more) second heterodimerizing NBD aa sequences;
    (ii) each of the one or more first heterodimerizing NBD aa sequences are cognate binding partners of the one or more second heterodimerizing NBD aa sequences; and
    (iii) the first polypeptide construct and the second polypeptide construct bind to each other through interactions between at least one of the one or more first heterodimerizing NBD aa sequences and at least one of the one or more second heterodimerizing NBD sequences in the presence of ATP to form a heterodimer or higher order complex of the first and second polypeptide constructs.
63. The composition of aspect 62, wherein the first polypeptide construct comprises a single first heterodimerizing NBD, and the second polypeptide construct comprises a single heterodimerizing NBD. See, e.g., FIG. 3 at J.
64. The composition of aspect 62, wherein the first polypeptide construct comprises two or more first heterodimerizing NBDs, and the second polypeptide construct comprises a single heterodimerizing NBD. See, e.g., FIG. 3 at K where the NBDs are in tandem.
65. The composition of aspect 62, wherein the first polypeptide construct comprises a single first heterodimerizing NBD, and the second polypeptide construct comprises two or more second heterodimerizing NBDs.
66. The composition of aspect 62, wherein the first polypeptide construct comprises two or more first heterodimerizing NBDs, and the second polypeptide construct comprises two or more second heterodimerizing NBDs.
67. The compositions of any one of aspects 62-66, wherein the first and/or second polypeptide construct comprises a scaffold sequence.
68. A composition comprising a first polypeptide construct of any one of aspects 21-38, and a second polypeptide construct of any one of aspects 1-18, wherein:
    (i) the first polypeptide construct comprises one or more (e.g., two or more) first heterodimerizing NBD aa sequences and the second polypeptide construct comprises one or more (e.g., two or more) second heterodimerizing NBD aa sequences;
    (ii) each of the one or more first heterodimerizing NBD aa sequences are cognate binding partners of the one or more second heterodimerizing NBD aa sequences; and
    (iii) the first polypeptide construct and the second polypeptide construct bind to each other through interactions between at least one of the one or more first heterodimerizing NBD aa sequences and at least one of the one or more second heterodimerizing NBD sequences in the presence of ATP to form a heterodimer or higher order complex of the first and second polypeptide constructs.
69. The composition of aspect 68, wherein the first polypeptide construct comprises a single first heterodimerizing NBD, and the second polypeptide construct comprises a single heterodimerizing NBD. See, e.g., FIG. 3 at A and E.
70. The composition of aspect 68, wherein the first polypeptide construct comprises two or more first heterodimerizing NBDs, and the second polypeptide construct comprises a single heterodimerizing NBD. See, e.g., FIG. 3 at B where the NBDs are in tandem, and N and O where the NBDs are not in tandem.
71. The composition of aspect 68, wherein the first polypeptide construct comprises a single first heterodimerizing NBD, and the second polypeptide construct comprises two or more second heterodimerizing NBDs.
72. The composition of aspect 68, wherein the first polypeptide construct comprises two or more first heterodimerizing NBDs, and the second polypeptide construct comprises two or more second heterodimerizing NBDs. See, e.g., FIG. 4A at G.
73. The composition of any one of aspects 62-66, wherein the first and/or second polypeptide construct comprises a scaffold sequence.
74. A composition comprising a first polypeptide construct of any of aspects 21-38, and a second polypeptide construct of any of aspects 42-58, wherein:
    (i) the first polypeptide construct comprises one or more (e.g., two or more) first heterodimerizing NBD aa sequences and the second polypeptide construct comprises one or more (e.g., two or more) second heterodimerizing NBD aa sequences;

(ii) each of the one or more first heterodimerizing NBD aa sequences are cognate binding partners of the one or more second heterodimerizing NBD aa sequences; and (iii) the first polypeptide construct and the second polypeptide construct bind to each other through interactions between at least one of the one or more first heterodimerizing NBD aa sequences and at least one of the one or more second heterodimerizing NBD sequences in the presence of ATP to form a heterodimer or higher order complex of the first and second polypeptide constructs.

75. The composition of aspect 74, wherein the first polypeptide construct comprises a single first heterodimerizing NBD, and the second complex comprises a single heterodimerizing NBD. See, e.g., FIG. 3 at C, F, and G.

76. The composition of aspect 74, wherein the first polypeptide construct comprises two or more first heterodimerizing NBDs, and the second complex comprises a single heterodimerizing NBD. See, e.g., FIG. 3 at M, F, G, and L, wherein the NBDs are in tandem, and N and O where the NBDs are not in tandem.

77. The composition of aspect 74, wherein the first polypeptide construct comprises a single first heterodimerizing NBD, and the second complex comprises two or more second heterodimerizing NBDs.

78. The composition of aspect 74, wherein the first polypeptide construct comprises two or more first heterodimerizing NBDs, and the second complex comprises two or more second heterodimerizing NBDs. See, e.g., FIG. 4A at E.

79. The composition of any one of aspects 62-67 and 74-78, further comprising an AD. See, e.g., 3 at D and FIG. 4A at I.

80. The polypeptide construct of any one of aspects 1-18, 21-38, and 42-58, wherein the construct comprises a scaffold.

81. The composition of any one of aspects 19-20, 39-41, and 59-61, wherein the first and/or second polypeptide construct comprises an independently selected scaffold.

82. The composition of any one of aspects 62-79, wherein the first and/or second polypeptide construct comprises an independently selected scaffold.

83. The polypeptide construct or composition of any one of aspects 80-82, wherein at least one scaffold (e.g., each scaffold present) does not comprise an immunoglobulin polypeptide aa sequence (e.g., it does not comprise an immunoglobulin Fc, $C_H1$, $C_H2$, or $C_H3$ domain).

84. The polypeptide construct or composition of any one of aspects 80-82, wherein at least one scaffold (e.g., each scaffold present) comprises an immunoglobulin polypeptide aa sequence (e.g., an IgFc, a CH2, or, a CH3 aa sequence).

85. The polypeptide construct or composition of aspect 84, wherein at least one (e.g., each) scaffold comprises an independently selected immunoglobulin polypeptide aa sequence of an IgG1 IgFc of SEQ ID NO:56 or 57, or a sequence having at least 90% or at least 95% sequence identity to SEQ ID NO:56 or 57.

86. The polypeptide construct or composition of aspect 84, wherein the at least one (e.g., each) scaffold comprises an independently selected non-dimerizing IgFc polypeptide aa sequence.

87. The polypeptide construct or composition of aspect 86, wherein at least one (e.g., each) scaffold comprises the IgFc polypeptide aa sequence of SEQ ID NO: 102, or a sequence having at least 90% or at least 95% sequence identity to SEQ ID NO: 102.

88. The polypeptide construct or composition of aspect 84, wherein the at least one (e.g., each) scaffold comprises an independently selected immunoglobulin polypeptide aa sequence of an IgG2, IgG3, or IgG4 IgFc of any one of SEQ ID NOs:58-60, or a sequence having at least 90% or at least 95% sequence identity to any one of SEQ ID NOs:58-60.

89. The polypeptide construct or composition of any one of aspects 85-88, wherein the immunoglobulin Fc (IgFc) polypeptide aa sequence may induce antibody related effector functions (e.g., ADCC, ADCP, and/or CDC) or the IgFc polypeptide sequence comprises one or more substitutions that enhance (e.g., substantially enhance) at least one (e.g., all) antibody related effector function selected from ADCC, ADCP, and CDC. Changes in function may be assessed relative to the polypeptide construct lacking the one or more substitutions.

90. The polypeptide construct or composition of any one of aspects 85-88, wherein the immunoglobulin Fc polypeptide aa sequence comprises one or more substitutions that diminish (e.g., substantially diminish) at least one (e.g., all) antibody related effector functions selected from ADCC, ADCP, and CDC (e.g., a LALA substitution). Changes in function may be assessed relative to the polypeptide construct lacking the one or more substitutions.

91. The polypeptide construct or composition of any preceding aspect, wherein, when one or more ADs are present, at least one (e.g., each) AD comprises an aa sequence of all or part of the polypeptides of: CD40L, CD28, IFN-γ, TNF superfamily members, TNF, lymphotoxin α, lymphotoxin αβ, BAFF (CD25), B7 superfamily members, CD80, CD86, IL-15, IL-2, IL-7, IL-10, IL-12, PD1, anti-CD3, anti-CTLA4, anti-CD28.

92. The polypeptide construct or composition of aspect 91, wherein the at least one (e.g., each) AD comprises an aa sequence having greater than 90% or greater than 95% sequence identity to IL-15, IL-12, or IL-7 (e.g., greater than 97% or greater than 99% sequence identity to IL-15, IL-12, or IL-7).

93. The polypeptide construct or composition of aspect 91, wherein the at least one (e.g., each) AD comprises the (i) single chain IL-12 of SEQ ID NO:90, or (ii) the IL-12 p40 subunit of SEQ ID NO:91 and/or the p35 subunit of SEQ ID NO:92, or an aa sequence having greater than 95% or greater than 98% sequence identity to any of those IL-12 sequences.

94. The polypeptide construct or composition of any preceding aspect, wherein, when one or more ADs are present, at least one (e.g., each) AD comprises an aa sequence that binds to PD1 (e.g., an anti-PD1 scFv or nanobody aa sequence that may act as an agonist of PD1) or an aa sequence that binds to PDL1 (e.g., an anti-PDL1 scFv or nanobody aa sequence).

95. The polypeptide construct or composition of any preceding aspect, wherein, when one or more ADs are present, at least one (e.g., each) AD comprises an aa sequence that binds to CD40 (e.g., an anti-CD40 scFv or nanobody aa sequence that may act as an agonist of CD40 signaling) or an aa sequence that binds to CD40L (e.g., an anti-CD40L scFv or nanobody aa sequence).

96. The polypeptide construct or composition of aspect 95, wherein the at least one (e.g., each) AD comprises the CD40L aa sequence of SEQ ID NO:96, the CD40L trimer aa sequence of SEQ ID NO:95, or an aa sequence having at least 90% or at least 95% sequence identity to either SEQ ID NO:95 or 96 (e.g., greater than 97% or greater than 99% sequence identity to either SEQ ID NO:95 or 96).

97. The polypeptide construct or composition of any preceding aspect, wherein, when one or more ADs are present, at least one (e.g., each) AD comprises an aa sequence that binds to CD137/4-1BB (e.g., an anti-CD137 scFv or nanobody aa sequence) or an aa sequence that binds to TGFβ (e.g., an anti-TGFβ scFv or nanobody aa sequence).

98. The polypeptide construct or composition of aspect 97, wherein the at least one (e.g., each) AD comprises the 4-1BBL sequence of SEQ ID NO:94, the 4-1BBL trimer aa sequence of SEQ ID NO:93, or an aa sequence having at least 90% or at least 95% sequence identity to either SEQ ID NO:93 or 94 (e.g., greater than 97% or greater than 99% sequence identity to either SEQ ID NO:93 or 94).

99. The polypeptide construct or composition of any preceding aspect, wherein, when one or more ADs are present, at least one (e.g., each) AD comprises an aa sequence that binds to IL-10 (e.g., an anti-IL-10 scFv or nanobody aa sequence) or an aa sequence that binds to the IL-10 receptor ("IL-10R") (e.g., an anti-IL-10R scFv or nanobody aa sequence).

100. The polypeptide construct or composition of any preceding aspect, wherein, when one or more ADs are present, at least one (e.g., each) AD comprises an aa sequence that binds to CTLA-4 (e.g., an anti-CTLA-4 scFv or nanobody aa sequence).

101. The polypeptide construct or composition of any preceding aspect, wherein, when one or more ADs are present, at least one (e.g., each) AD comprises an aa sequence that binds to CD3 (e.g., an anti-CD3 scFv or nanobody aa sequence).

102. The polypeptide construct or composition of any preceding aspect, wherein, when one or more ADs are present, at least one (e.g., each) AD comprises an aa sequence that binds to CD28 (e.g., an anti-CD28 scFv or nanobody aa sequence).

103. The polypeptide construct or composition of aspect 102, wherein the at least one (e.g., each) AD comprises the anti-CD28 scFv sequence of SEQ ID NO:89, or an aa sequence having at least 90% or at least 95% sequence identity to SEQ ID NO:89 (e.g., greater than 96% or greater than 99% sequence identity to SEQ ID NO:89).

104. The polypeptide construct or composition of any preceding aspect, wherein, when one or more ADs are present, at least one (e.g., each) AD comprises an aa sequence that binds to IFN-γ receptor (e.g., an anti-IFN-γ receptor scFv or nanobody aa sequence).

105. The polypeptide construct or composition of aspect 104, wherein the at least one (e.g., each) AD comprises the scIFN-γ polypeptide of SEQ ID NO:97, or an aa sequence having at least 90% or at least 95% sequence identity to SEQ ID NO:97 (e.g., greater than 96% or greater than 99% sequence identity to SEQ ID NO:97).

106. The polypeptide construct or composition of any preceding aspect, wherein, when one or more ADs are present, at least one (e.g., each) AD comprises an aa sequence that binds to CD16 (e.g., an anti-CD16 scFv or nanobody aa sequence).

107. The polypeptide construct or composition of aspect 106, wherein the at least one (e.g., each) AD comprises the anti-CD16 VHH polypeptide of SEQ ID NO:98 or 103, or an aa sequence having at least 90% or at least 95% sequence identity to either SEQ ID NO:98 or 103 (e.g., greater than 96% or greater than 99% sequence identity to either SEQ ID NO:98 or 103).

108. The polypeptide construct or composition of any preceding aspect, wherein, when one or more ADs are present, at least one (e.g., each) AD comprises the CD80 aa sequence of SEQ ID NO:99, or an aa sequence having at least 90% or at least 95% sequence identity to SEQ ID NO:99 (e.g., greater than 96% or greater than 99% sequence identity to SEQ ID NO:99).

109. The polypeptide construct or composition of any preceding aspect, wherein, when one or more ADs are present, at least one (e.g., each) AD comprises the CD86 aa sequence of either SEQ ID NO:100 or 101, or an aa sequence having at least 90% or at least 95% sequence identity to either SEQ ID NO: 100 or 101 (e.g., greater than 96% or greater than 99% sequence identity to either SEQ ID NO: 100 or 101).

110. The polypeptide construct or composition of any preceding aspect, wherein, when one or more ADs are present, at least one (e.g., each) AD comprises a nucleic acid with CpG repeats (e.g., a CpG oligodeoxynucleotide sequence).

111. The polypeptide construct or composition of any preceding aspect, wherein, when one or more ADs are present, at least one (e.g., each) AD comprises a nucleic acid comprising the sequence TCATCATTTTGTCAT-TTTGTCATT (SEQ ID NO:69) optionally having 1, 2 or 3 nucleotide substitutions, deletions, or insertions.

112. The polypeptide construct or composition of any preceding aspect, wherein, when one or more (e.g., two or more) TSBs are present in the construct or composition at least one (e.g., at least two, or each) TSB is independently selected to display affinity for a TAA selected from the group consisting of: carbonic anhydrase IX (CAIX), cadherins, carcinoembryonic antigen (CEA), cellular-mesenchymal epithelial transition factor (c-MET), Cytotoxic T-Lymphocyte Associated Protein 4 (CTLA-4), Epidermal Growth Factor Receptor (EGFR) family members, Epithelial Cell Adhesion Molecule (EpCAM), Ephrin Type-A Receptor 3 (EphA3), Fibroblast Activation Protein Alpha (FAP), folate-binding protein, Folate Receptor alpha (FR-alpha), Erb-B2 Receptor Tyrosine Kinase 2 (HER2), Erb-B2 Receptor Tyrosine Kinase 3 (HER3), Insulin Like Growth Factor 1 Receptor (IGF-1R), integrin αVβ3, integrin α5β1, Solute Carrier Family 39 Member 6 (Liv1), a Melanoma-Associated Antigen family A member (MAGEA), a Melanoma-Associated Antigen family C member (MAGEC), mesothelin, a mucin (e.g., MUC1), a New York Esophageal Squamous Cell Carcinoma 1 protein (NY-ESO-1, Cancer/Testis Antigen 1A, Cancer/Testis Antigen 1B), Cancer/Testis Antigen 2 (NY-ESO-2, CTAG2), Prostate-Specific Membrane Antigen (PSMA), Receptor Activator of Nuclear Factor Kappa B Ligand (RANKL), Receptor Tyrosine Kinase Like Orphan Receptor 1 (ROR1), tenascin, TNF Receptor Superfamily Member 10a (TRAILR1), TNF Receptor Superfamily Member 10b (TRAILR2), and Vascular Endothelial Growth Factor Receptor (VEGFR).

113. The polypeptide construct or composition of aspect 112, wherein the at least one (e.g., at least two, or each)

TSB comprises an anti-human mesothelin scFv of SEQ ID NO:70 or an aa sequence having greater than 90% or greater than 95% sequence identity to SEQ ID NO:70 (e.g., greater than 96% or greater than 98% sequence identity to SEQ ID NO:70).

114. The polypeptide construct or composition of aspect 112 or 113, wherein the at least one (e.g., at least two, or each) TSB comprises an anti-human mesothelin scFv (vH-vL) of SEQ ID NO:71 or an aa sequence having greater than 90% or greater than 95% sequence identity to SEQ ID NO:71 (e.g., greater than 96% or greater than 98% sequence identity to SEQ ID NO:71).

115. The polypeptide construct or composition of any one of aspects 112-114, wherein the at least one (e.g., at least two, or each) TSB comprises an anti-human mesothelin scFv (vL-vH) of SEQ ID NO:72 or an aa sequence having greater than 90% or greater than 95% sequence identity to SEQ ID NO:72 (e.g., greater than 96% or greater than 98% sequence identity to SEQ ID NO:72).

116. The polypeptide construct or composition of any one of aspects 112-115, wherein the at least one (e.g., at least two, or each) TSB comprises an anti-human mesothelin scFv (vH-vL) of SEQ ID NO:73 or an aa sequence having greater than 90% or greater than 95% sequence identity to SEQ ID NO:73 (e.g., greater than 96% or greater than 98% sequence identity to SEQ ID NO:73).

117. The polypeptide construct or composition of any one of aspects 112-116, wherein the at least one (e.g., at least two, or each) TSB comprises an anti-human mesothelin scFv (vL-vH) of any of SEQ ID NOs:74-78 or an aa sequence having greater than 90% or greater than 95% sequence identity to any of SEQ ID NOs: 74-78.

118. The polypeptide construct or composition of aspect 117, wherein the anti-human mesothelin scFv (vL-vH) has greater than 96% or greater than 98% sequence identity to any of SEQ ID NOs:74-78.

119. The polypeptide construct or composition of any one of aspects 112-118, wherein the at least one (e.g., at least two, or each) TSB comprises an anti-human mesothelin VHH (nanobody) of SEQ ID NO:79, or an aa sequence having greater than 90% or greater than 95% sequence identity to SEQ ID NO:79 (e.g., greater than 96% or greater than 98% sequence identity to SEQ ID NO:79).

120. The polypeptide construct or composition of any one of aspects 112-119, wherein the at least one (e.g., at least two, or each) TSB comprises an anti-human EpCAM scFv (vH-vL) of SEQ ID NO:80 or an aa sequence having greater than 90% or greater than 95% sequence identity to SEQ ID NO:80 (e.g., greater than 96% or greater than 98% sequence identity to SEQ ID NO:80).

121. The polypeptide construct or composition of any one of aspects 112-120, wherein the at least one (e.g., at least two, or each) TSB comprises an anti-human EpCAM scFv (vL-vH) of SEQ ID NO:81 or an aa sequence having greater than 90% or greater than 95% sequence identity to SEQ ID NO:81 (e.g., greater than 96% or greater than 98% sequence identity to SEQ ID NO:81).

122. The polypeptide construct or composition of any one of aspects 112-121, wherein the at least one (e.g., at least two, or each) TSB comprises an anti-human CTLA-4 scFv (vL-vH) of any of SEQ ID NOs:82-86 or an aa sequence having greater than 90% or greater than 95% sequence identity to any of SEQ ID NOs: 82-86.

123. The polypeptide construct or composition of aspect 122, wherein the anti-human CTLA-4 scFv (vL-vH) has greater than 96% or greater than 98% sequence identity to any of SEQ ID NOs: 82-86.

124. The polypeptide construct or composition of any of aspects 1-111, wherein, when one or more TSBs are present in the construct or composition, at least one (e.g., at least two, or each) TSB displays affinity for a checkpoint protein.

125. The polypeptide construct or composition of aspect 124, wherein the checkpoint protein is selected from the group consisting of V-domain Ig suppressor of T cell activation (VISTA), T-cell immunoglobulin and mucin-domain containing-3 (TIM-3), PD-L1, CTLA-4, and lymphocyte-activation gene 3 (LAG-3).

126. A polypeptide construct or composition of any of aspects 1-125, wherein when one or more immune cell engagers (ICEs) are present in the construct or composition at least one (e.g., at least two, or each) independently selected ICE aa sequences has affinity for (e.g., binding to) a protein selected from the group consisting of: CD3, CD4, CD8, αβTCR, CD2, TCRα chain, TCRβ chain, δγ TCR, TCR γ chain, TCR δ chain, TRGV9, CD84, CXCR1, CD13, CD33, CD34, and CD16.

127. A polypeptide construct or composition aspect 126, wherein the at least one ICE aa sequence (e.g., at least two, or each ICE sequence) is selected independently from the group consisting of antibody, antigen binding fragment(s) of an antibody, Fab, Fab', scFv, aptamer, and nanobody aa sequences.

128. The polypeptide construct or complex of aspect 126 or 127, wherein the at least one (e.g., at least two, or each) ICE comprises a scFv, an anti-human CD3 comprising the sequence of SEQ ID NO:61 or 62, or a sequence having greater than 90% or greater than 95% sequence identity to either SEQ ID NO:61 or 62 (e.g., an aa sequence having greater than 96% or greater than 98% sequence identity to either SEQ ID NO:61 or 62).

129. The polypeptide construct or composition of any one of aspects 126-128, wherein the at least one (e.g., at least two, or each) ICE comprises an anti-human CD3 VHH comprising the sequence of SEQ ID NO:63, or a sequence having greater than 90% or greater than 95% sequence identity to SEQ ID NO:63 (e.g., an aa sequence having greater than 96% or greater than 98% sequence identity to SEQ ID NO:63).

130. The polypeptide construct or composition of any one of aspects 126-129, wherein the at least one (e.g., at least two, or each) ICE comprises an anti-human CD3 scFv (vH-vL) comprising the sequence of any one of SEQ ID NOs:64-68, or a sequence having greater than 90% or greater than 95% sequence identity to any of SEQ ID NO:64-68 (e.g., an aa sequence having greater than 96% or greater than 98% sequence identity to either SEQ ID NO: 64-68).

131. The polypeptide construct or composition of any preceding aspect, wherein each NBD is a NBD of an ATP-binding cassette (ABC) transporter.

132. The polypeptide construct or composition of aspect 131, wherein the ABC transporter is a member of the ABC1, MDR/TAP, MRP, ALD, OABP, GCN20, or White ABC transporter family.

133. The polypeptide construct or composition of aspect 131, wherein the ABC transporter NBD comprises an aa sequence selected from ABCA1 (SEQ ID NO:1), ABCB1 (SEQ ID NO:2), ABCC1 (SEQ ID NO:3), ABCD1 (SEQ ID NO:4), ABCE1 (SEQ ID NO:5), ABCF1 (SEQ ID NO:6), ABCG2 (SEQ ID NO:7), and TAP1 (SEQ ID NO:9), or a sequence having greater than 90% or greater than 95% sequence identity to any one of those sequences.

134. The polypeptide construct or composition of aspect 133, wherein the NBD comprises an aa sequence having greater than 97% or greater than 98% sequence identity to any one of the aa sequences of SEQ ID NOs: 1-7 and 9.

135. The polypeptide construct or composition of aspect 131, wherein the NBD comprises aTAP2 aa sequence, a TAP2 aa sequence of SEQ ID NO:11, or an aa sequence having greater than 90% or greater than 95% sequence identity to the aa sequence of SEQ ID NO:11.

136. The polypeptide construct or composition of aspect 135, wherein the NBD comprises an aa sequence having greater than 97% or greater than 98% sequence identity to the aa sequences of SEQ ID NO:11.

137. The polypeptide construct or composition of aspect 131, wherein the NBD comprises a TAP1 NBD aa sequence.

138. The polypeptide construct or composition of aspect 137, wherein the NBD comprises the aa sequence of SEQ ID NO:9, or a sequence having greater than 90% or greater than 95% sequence identity to the sequence of SEQ ID NO:9.

139. The polypeptide construct or composition of aspect 138, wherein the NBD comprises an aa sequence having greater than 97% or greater than 98% sequence identity to the aa sequence of SEQ ID NO:9.

140. The polypeptide construct or composition of aspect 131, wherein the NBD comprises the TAP1 aa sequence of any one of SEQ ID NOs: 10, 87, or 88, or a sequence having greater than 90% or greater than 95% sequence identity to any one of those sequences.

141. The polypeptide construct or composition of aspect 140, wherein the NBD comprises an aa sequence having greater than 97% or greater than 98% sequence identity to the TAP1 aa sequences of SEQ ID NOs: 10, 87, or 88.

142. The polypeptide construct or composition of aspect 140, wherein the NBD comprises the TAP1 aa sequence of SEQ ID NO:88, or a TAP1 aa sequence having greater than 90% or greater than 95% sequence identity to the TAP1 aa sequence of SEQ ID NO:88.

143. The polypeptide construct or composition of aspect 142, wherein the NBD comprises a TAP1 aa sequence having greater than 97% or greater than 98% sequence identity to the TAP1 aa sequence of SEQ ID NO:88.

144. The polypeptide construct or composition of any one of aspects 131-143, wherein the NBD comprises a non-homodimerizing NBD.

145. The polypeptide construct of aspect 144, wherein the NBD comprises a substitution for at least one (e.g., at least two or at least three) of aas N185, S186, Q189, E191, and Q192.

146. The polypeptide construct or composition of any one of aspects 131-145, wherein at least one (e.g., each) NBD has a substitution that renders the at least one (e.g., each) NBD substantially ATP hydrolysis deficient.

147. The polypeptide construct or composition of aspect 146, wherein the at least one (e.g., each) NBD comprises a TAP1 NBD having a D668 substitution (e.g., D668N) numbered as in SEQ ID NO:8, or a corresponding substitution (in, for example, any of SEQ ID NOs:9, 10, 87, or 88) that renders the at least one (e.g., each) NBD substantially ATP hydrolysis deficient.

148. The polypeptide construct or composition of any preceding aspect, comprising one or more independently selected linkers (e.g., flexible or rigid linkers), optionally located between any of the NBD aa sequence, the scaffold aa sequence, and the AD aa sequence.

149. The polypeptide construct or composition of aspect 148, wherein the one or more independently selected linkers comprise an aa sequence selected independently from any of SEQ ID NOs: 16-35.

150. The polypeptide construct or composition of aspect 148 or 149, further comprising one or more independently selected rigid linker aa sequences.

151. The polypeptide construct or composition of aspect 150, wherein the one or more independently selected rigid linker aa sequences is/are selected independently from any of SEQ ID NOs:36-55.

152. A dimer or higher order complex of constructs comprising two or more constructs, or a first polypeptide construct and a second polypeptide construct (e.g., a composition) according to any of aspects 1-151 and at least one molecule (e.g., at least two molecules) of ATP.

153. The dimer or other higher order complex of aspect 152, wherein each of the constructs in the complex is identical.

154. The dimer or other higher order complex of aspect 153, wherein the dimer or other higher order complex is a homodimer.

155. The dimer or higher order complex of aspect 152, wherein each of the constructs in the complex is not identical.

156. The dimer or other higher order complex of aspect 155, wherein the dimer or other higher order complex is a heterodimer.

157. A population of constructs (e.g., group or collection of constructs as a composition) comprising at least one or at least two of the dimer or higher order complex of constructs of any of aspects 152-156.

158. The population of aspect 157, wherein at least one or at least two of the dimer or higher order complex of constructs comprise immunoglobulin constant regions that effect ADCC, ADCP, and/or CDC.

159. The population of aspect 157, wherein at least one or at least two of the dimer or higher order complex of constructs comprise an independently selected AD.

160. The population of aspect 157 or 159 wherein at least one or at least two of the dimer or higher order complex of constructs comprise an independently selected ICE.

161. The population of any of aspects 157-160, wherein at least one or at least two of the dimer or higher order complex of constructs comprise an independently selected TSB.

162. A polypeptide construct of any of aspects 1-151, having a structure set forth in any of FIG. 2, 3, 4A, or 4B. 163. A pair of constructs of any of aspects 1-151, having a structure set forth in any of FIG. 2, 3, 4A, or 4B.

164. A dimer or higher order complex of any of aspects 152-156, having a structure set forth in any of FIG. 2 or 3.

165. A dimer or higher order complex of any of aspects 152-156, having a structure set forth in any of FIG. 4A or 4B.
166. A dimer or higher order complex of any of aspects 152-156, having a structure set forth in any of FIG. 2, 3, 4A, or 4B.
167. The dimer or higher order complex of any of aspects 152-156, comprising a homodimer of TAP1 or TAP2 NBD aa sequences, or a heterodimer of TAP1 and TAP2 NBD aa sequences.
168. A method of stimulating CD4+ T cells, oy T cell, NK cells, myeloid derived suppressor cells, and/or CD8+ T cells comprising contacting the cells with a construct or composition of any of aspects 1-151, in the presence of sufficient ATP to bind to the NBD.
169. The method of aspect 168, conducted in vitro, or outside of the body of a mammal or non-mammalian animal.
170. The method of aspect 169, conducted in a cell or tissue.
171. The method of aspect 168, conducted in vivo or within the body of a mammal.
172. A method of treating a cancer comprising administering a construct or composition of any one of aspects 1-151 to a patient or subject.
173. The method of any of aspects 169-172, wherein the mammal is a human.
174. The use of a construct or composition of any of aspects 1-151 for the preparation of a medicament for the treatment of a cancer.
175. The method or use of any one of aspects 172-174, wherein the cancer comprises a solid tumor.
176. A polypeptide construct or composition of any of aspects 1-151 for the treatment of a cancer.
177. The polypeptide construct or composition of aspect 176, wherein the cancer comprises a solid tumor.
178. The method, use, construct or composition of any of aspects 172-176, wherein the cancer is a mesothelioma, melanoma, sarcoma, carcinoma, carcinosarcoma, lymphoma, or germ cell tumor.
179. A nucleic acid comprising a sequence encoding one or more constructs, or one or more constructs of a composition, of any of aspects 1-151.
180. A vector comprising the nucleic acid of aspect 179, optionally under the control of a promoter (e.g., a constitutive promoter) or an inducible promoter.
181. A cell comprising the vector or nucleic acid of aspect 179 or 180.
182. The cell of aspect 181, wherein the cell is a mammalian cell, yeast cell, insect cell, or bacterial cell.

VII. EXAMPLES

Example 1

Figure 8:
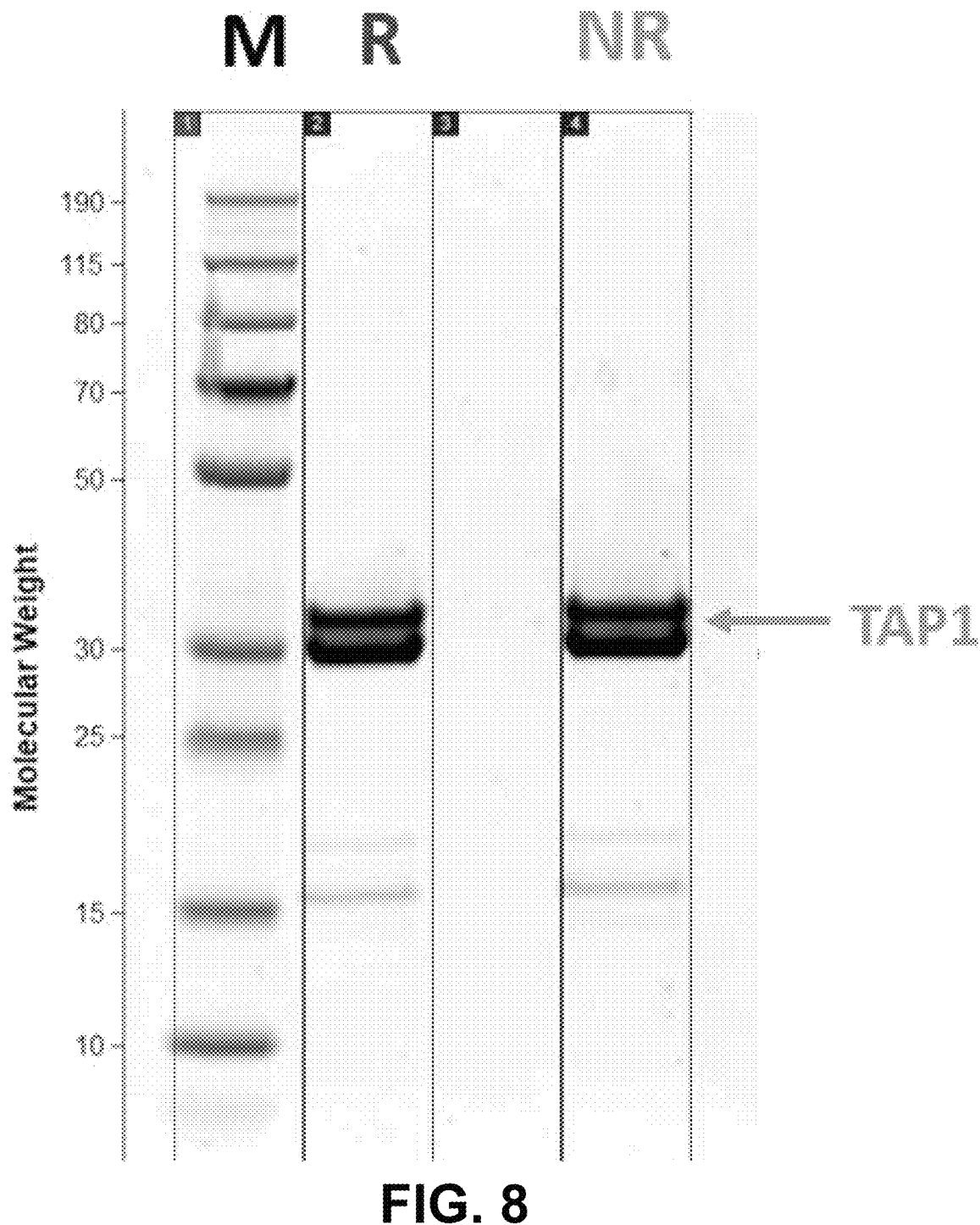
FIG. 8 shows a SDS-polyacrylamide gel electrophoresis (PAGE) gel of a TAP1 variant bearing N676G, S677N, Q680R, E682Q, and/or Q683R substitutions. From left to right the lanes are: molecular weight markers (M), reduced sample (R), empty lane, and non-reduced sample (NR).

In order to test the functionality of TAP1 NBD to homodimerize in solution, a human TAP1 NBD comprising: (i) N676, S677, Q680, E682, and Q683 (e.g., N676G, S677N, Q680R, E682Q, and Q683R substitutions), (ii) substitutions of cysteines present in the sequence with serines (SEQ ID NO:10) and (iii) a C-terminal His tag for purification was expressed in *E. coli* and subsequently purified. Samples of the molecular weight markers and the purified protein were subject to SDS-PAGE gel analysis under reducing and non-reducing conditions as shown in FIG. 8 (lanes: M—molecular weight markers, R—reduced protein sample, NR non-reduced protein sample).

Samples of the purified TAP1 NBD were exposed to 1 mM ADP or 1 mM ATP and subject to size exclusion chromatography. The results, shown in FIG. 9, indicate that in the presence of ADP the protein chromatographs with an effective molecular weight of 37 kDa whereas in the presence of ATP the protein chromatographs with an effective molecular weight of 57 kDa. The results indicate the TAP1 protein dimerizes in the presence of ATP. The dimerization was confirmed using mass photometry and dynamic light scattering (DLS) to determine molecular weight. Mass photometry yielded an effective molecular weight of 62 kDa in the presence of 1 mM ATP (see FIG. 10), in agreement with the chromatographic result. DLS in 20 mM Tris (pH 8.0), 50 mM NaCl, 5 mM MgCl2, 10% glycerol in the presence of 1 mM ADP (FIG. 11 at A) or 1 mM ATP (FIG. 11 at B) yielded a size of 5.517 in the presence of ADP and 8.057 in the presence of ATP, again consistent with dimerization of the protein in the presence of 1 mM ATP. The DLS results are provided in the table below.

| Sample Name | Polydispersity Index (PI) | Size distribution by volume (nm) |
| --- | --- | --- |
| NBD1 in ADP Buffer | 0.3356 | 5.157 |
| NBD1 in ATP Buffer | 0.6278 | 8.057 |

Example 2

The TAP1 NBD of SEQ ID NO:87 with a peptide comprising a SpyTag3, TEV protease, and a His tag attached at the C-terminus was expressed in *E. coli*. and the cells pelleted and frozen until analysis. The TAP1 NBD fragment was purified by cell lysis followed by chromatograph on a HisTrap column. For the analysis cell pellets were thawed and resuspended with 200 ml lysis buffer (20 mM Tris-Cl pH 8.0, 500 mM NaCl, 5 mM MgCl$_2$, 10% glycerol, 2 mM ATP) supplemented with 100 μg/ml lysozyme, 2 protease inhibitor tablets (Thermo Pierce A32965) and Universal Nuclease (Thermo Pierce 88702) added to 12.5 U/ml. Cells were incubated with stirring at 4° C. for 30 minutes then lysed by sonication at 80% intensity for a total of 4 minutes active time (5 seconds on, 15 seconds rest on ice per cycle). Lysate was then clarified by centrifugation at 12,000×g for 1 hour at 4° C., then 0.22-μm filtered and loaded onto a 1 ml HisTrap HP column (Cytiva) at 0.5 ml/min recirculating with a peristaltic pump overnight. The following day, the column was switched to flow-through, and after complete lysate loading at 1 ml/min, the column was washed with 10 column volumes (CV) of lysis buffer supplemented with 7 mM β-mercaptoethanol and 20 mM imidazole. The column was then transferred to an ÄKTAxpress FPLC, and bound proteins were eluted with an imidazole gradient from 0 to 500 mM over 40 CV in binding buffer (20 mM Tris-Cl pH 8.0, 200 mM NaCl, 5 mM MgCl$_2$, 10% glycerol, 2 mM ATP, 0.5 mM PMSF). Column fractions were assessed by SDS-PAGE, and fractions containing target protein were pooled and concentrated (10 kDa MWCO) to 10 ml before loading as 3 injections (~3.3 ml per injection) onto a Superdex 200

16/600 column equilibrated in target buffer (20 mM Tris-Cl pH 8.0, 50 mM NaCl, 5 mM MgCl$_2$, 10% glycerol, 1 mM ATP). Elution peak fractions were assessed by SDS-PAGE, and target protein-containing fractions were pooled and concentrated (10 kDa molecular weight cutoff) to 10 mg/ml before aliquotting (500 µl/tube) and storage at 4° C.

The purified protein was subject to SDS-PAGE along with molecular weight samples. The coomassie blue stained gel is provided in FIG. 12, the leftmost lane is molecular weight samples and the rightmost lane is the purified protein.

Samples of the purified protein (1 mg each) were buffer-exchanged on PD-10 columns (Cytiva 17085101) according to manufacturer instructions. For the buffer exchange PD-10 desalting columns were equilibrated with target buffer (20 mM Tris-Cl pH 8.0, 50 mM NaCl, 5 mM MgCl2, 10% glycerol) containing either 1 mM ATP or 1 mM ADP. One milligram (100 µl of 10 mg/ml stock) of protein was added to each column along with 2.4 ml of target buffer, the column was centrifuged at 1000×g for 2 minutes in a 50-ml conical tube, and the eluate was collected. Buffer-exchanged proteins were then concentrated to 0.5 ml (~60 µM) and loaded onto a Superdex S200 Increase column (Cytiva) equilibrated in the appropriate buffer containing ATP or ADP and eluted at 0.5 ml/min. The ATP-containing sample eluted at a volume of 15.75 ml, corresponding to a molecular weight of approximately 65 kDa, while the ADP sample eluted at 16.81 ml, corresponding to approximately 38 kDa. Traces of the chromatographic analysis are provided in FIG. 12.

For determination of molecular weight by size exclusion chromatography in the presence of ADP and ATP, purified protein samples (1 mg each) were buffer-exchanged on PD-10 columns (Cytiva 17085101) according to manufacturer instructions. Briefly, PD-10 desalting columns were equilibrated with target buffer (20 mM Tris-Cl pH 8.0, 50 mM NaCl, 5 mM MgCl$_2$, 10% glycerol) containing either 1 mM ATP or ADP. One milligram (100 µl of 10 mg/ml stock) of protein was added to each column along with 2.4 ml of target buffer, the column was centrifuged at 1000×g for 2 minutes in a 50-ml conical tube, and the eluate was collected. Buffer-exchanged proteins were then concentrated to 0.5 ml (~60 µM), loaded onto a Superdex S200 Increase column (Cytiva), and equilibrated in the appropriate buffer containing ATP or ADP at 0.5 ml/min. The ATP-containing sample eluted at a volume of 15.75 ml, corresponding to a molecular weight of approximately 65 kDa, while the ADP sample eluted at 16.81 ml, corresponding to approximately 38 kDa.

Example 3

For assessment of the uninduced and induced expression of NBD polypeptide, samples of E. coli BL21 (DE3) were transformed with a vector that permits isopropyl-beta-D-thiogalactoside (IPTG) inducible expression of the NBD of SEQ ID NO:87 or SEQ ID NO:88 with a peptide comprising a SpyTag3, TEV protease site, and His tagged at the C-terminus. For analysis of the uninduced and induced fractions, the optical density (OD) at 600 nm for each of the cultures was monitored up until induction at 0.4 OD when an aliquot equivalent to 1 OD-ml (e.g. 2.5 ml of 0.4 OD) was taken. The cells in the aliquots were pelleted at 6800× g for 3 minutes, and the pellet resuspended in 300 µl of 1×PBS, after which the resuspended material was frozen at −80 C. After induction with 80 µM IPTG the cells were grown and a comparable sample of 1 OD-ml (e.g. 0.25 ml of 4 OD) was collected during the final harvest after induction. For analysis of induction the frozen samples were thawed and the cells in all samples were lysed by mixing with an equal volume of 2× lysis buffer (1×PBS with 0.2% Triton X-100, 100 g/ml lysozyme and 2× concentration of Universal Nuclease from Pierce). Samples were incubated on a rocker at 4° C. for 30 minutes, after which the lysates were spun at 21,000×g for 10 minutes to pellet debris. Samples (30 µl) of the supernatant were mixed with 10 µl of 4×SDS-PAGE loading buffer, heated at 70° C. for about 5 minutes, then loaded on a SDS-PAGE gel. Results are shown in FIG. 13, SDS-PAGE gel A.

For determination expression levels and molecular weight by size exclusion chromatography, samples of the NBD polypeptides of SEQ ID NOs:87 and 88 were expressed in E. coli and purified for SDS-PAGE and chromatographic analysis as in Example 2. The results of chromatographic molecular weight determinations and protein yield, which is about two orders of magnitude (90-fold) higher for the "capped" NBD of SEQ ID NO:88 relative to that of SEQ ID NO:87 are provided in the table that follows.

| TAP1 polypeptide | Yield from Culture | MW in 1 mM ADP buffer | MW in 1 mM ATP buffer |
|---|---|---|---|
| SEQ ID NO: 87 | 100 µg/liter | 38 kDa | 65 kDa |
| SEQ ID NO: 88 | 9 mg/liter | 38.1 kDa | 78 kDa |

FIG. 13 provides SDS PAGE analysis of induced and uninduced expression at A and analysis of the purified protein at B. The lanes of the reducing SDS-PAGE gel images provided in FIG. 13 are as follows

| Gel (A) Induced vs. Uninduced Expression | | Gel (B) Evaluation of the purified NBD polypeptide of SEQ ID NO: 88 | |
|---|---|---|---|
| Lane | Sample | Lane | Sample |
| 1 | Molecular Weight Markers | 1 | Molecular Weight Markers |
| 2 | Expression of the NBD polypeptide of f SEQ ID NO: 87 prior to induction | 2 | Additional purified NBD polypeptide |
| 3 | Expression of the NBD polypeptide of SEQ ID NO: 87 after induction (see white box and arrow) | 3 | Additional purified NBD polypeptide |
| 4 | Expression of the NBD polypeptide of SEQ ID NO: 88 prior to induction | 4 | The purified NBD polypeptide of SEQ ID NO:88 |
| 5 | Expression of the NBD polypeptide of SEQ ID NO: 88 after induction (see white box) | | |

SEQUENCE LISTING

```
Sequence total quantity: 103
SEQ ID NO: 1                  moltype = AA   length = 288
FEATURE                       Location/Qualifiers
REGION                        1..288
                              note = Description of sequence: Nucleotide binding domain
                               of the ABCA1 gene product of UniProtKB - O95477
source                        1..288
                              mol_type = protein
                              organism = Homo sapiens
SEQUENCE: 1
RILDGGGQND ILEIKELTKI YRRRKPAVD RICVGIPPGE CFGLLGVNGA GKSSTFKMLT    60
GDTTVTRGDA FLNKNSILSN IHEVHQNMGY CPQFDAITEL LTGREHVEFF ALLRGVPEKE   120
VGKVGEWAIR KLGLVKYGEK YAGNYSGGNK RKLSTAMALI GGPPVVFLDE PTTGMDPKAR   180
RFLWNCALSV VKEGRSVVLT SHSMEECEAL CTRMAIMVNG RFRCLGSVQH LKNRFGDGYT   240
IVVRIAGSNP DLKPVQDFFG LAFPGSVLKE KHRNMLQYQL PSSLSSLA                288

SEQ ID NO: 2                  moltype = AA   length = 257
FEATURE                       Location/Qualifiers
REGION                        1..257
                              note = Description of sequence: Nucleotide binding domain
                               of ABCB1 gene product from UniProtKB - P08183
source                        1..257
                              mol_type = protein
                              organism = Homo sapiens
SEQUENCE: 2
EGLMPNTLEG NVTFGEVVFN YPTRPDIPVL QGLSLEVKKG QTLALVGSSG CGKSTVVQLL    60
ERFYDPLAGK VLLDGKEIKR LNVQWLRAHL GIVSQEPILF DCSIAENIAY GDNSRVVSQE   120
EIVRAAKEAN IHAFIESLPN KYSTKVGDKG TQLSGGQKQR IAIARALVRQ PHILLLDEAT   180
SALDTESEKV VQEALDKARE GRTCIVIAHR LSTIQNADLI VVFQNGRVKE HGTHQQLLAQ   240
KGIYFSMVSV QAGTKRQ                                                  257

SEQ ID NO: 3                  moltype = AA   length = 389
FEATURE                       Location/Qualifiers
REGION                        1..389
                              note = Description of sequence: Nucleotide binding domain
                               of ABCC1 gene product from UniProtKB - P33527
source                        1..389
                              mol_type = protein
                              organism = Homo sapiens
SEQUENCE: 3
RRPVKDGGGT NSITVRNATF TWARSDPPTL NGITFSIPEG ALVAVGQVG CGKSSLLSAL     60
LAEMDKVEGH VAIKGSVAYV PQQAWIQNDS LRENILFGCQ LEEPYYRSVI QACALLPDLE   120
ILPSGDRTEI GEKGVNLSGG QKQRVSLARA VYSNADIYLF DDPLSAVDAH VGKHIFENVI   180
GPKGMLKNKT RILVTHSMSY LPQVDVIIVM SGGKISEMGS YQELLARDGA FAEFLRTYAS   240
TEQEQDAEEN GVTGVSGPGK EAKQMENGML VTDSAGKQLQ RQLSSSSSYS GDISRHHNST   300
AELQKAEAKK EETWKLMEAD KAQTGQVKLS VYWDYMKAIG LFISFLSIFL FMCNHVSALA   360
SNYWLSLWTD DPIVNGTQEH TKVRLSVYG                                     389

SEQ ID NO: 4                  moltype = AA   length = 280
FEATURE                       Location/Qualifiers
REGION                        1..280
                              note = Description of sequence: Nucleotide binding domain
                               of he ABCD1 gene product from UniProtKB/Swiss-Prot: P33897
source                        1..280
                              mol_type = protein
                              organism = Homo sapiens
SEQUENCE: 4
GPLKIRGQVV DVEQGIICEN IPIVTPSGEV VVASLNIRVE EGMHLLITGP NGCGKSSLFR    60
ILGGLWPTYG GVLYKPPPQR MFYIPQRPYM SVGSLRDQVI YPDSVEDMQR KGYSEQDLEA   120
ILDVVHLHHI LQREGGWEAM CDWKDVLSGG EKQRIGMARM FYHRPKYALL DECTSAVSID   180
VEGKIFQAAK DAGIALLSIT HRPSLWKYHT HLLQFDGEGG WKFEKLDSAA RLSLTEEKQR   240
LEQQLAGIPK MQRRLQELCQ ILGEAVAPAH VPAPSPQGPG                         280

SEQ ID NO: 5                  moltype = AA   length = 293
FEATURE                       Location/Qualifiers
REGION                        1..293
                              note = Description of sequence: Nucleotide binding domain
                               of ABCE1 gene product from UniProtKB/Swiss-Prot: P61221
source                        1..293
                              mol_type = protein
                              organism = Homo sapiens
SEQUENCE: 5
GALSIVNLPS NLEKETTHRY CANAFKLHRL PIPRPGEVLG LVGTNGIGKS TALKILAGKQ    60
KPNLGKYDDP PDWQEILTYF RGSELQNYFT KILEDDLKAI IKPQYVDQIP KAAKGTVGSI   120
LDRKDETKTQ AIVCQQLDLT HLKERNVEDL SGGELQRFAC AVVCIQKADI FMFDEPSSYL   180
DVKQRLKAAI TIRSLINPDR YIIVEHDLS VLDLYSDFIC CLYGVPSAYG VVTMPFSVRE    240
GINIFLDGYV PTENLRFRDA SLVFKVAETA NEEEVKKMCM YKYPGMKKKM GEF          293
```

```
SEQ ID NO: 6              moltype = AA  length = 228
FEATURE                   Location/Qualifiers
REGION                    1..228
                          note = Description of sequence: Nucleotide binding domain
                            of the ABCF1 gene product from UniProtKB - Q8NE71
source                    1..228
                          mol_type = protein
                          organism = Homo sapiens
SEQUENCE: 6
PPLSPPVLGL HGVTFGYQGQ KPLFKNLDFG IDMDSRICIV GPNGVGKSTL LLLLTGKLTP     60
THGEMRKNHR LKIGFFNQQY AEQLRMEETP TEYLQRGFNL PYQDARKCLG RFGLESHAHT    120
IQICKLSGGQ KARVVFAELA CREPDVLILD EPTNNLDIES IDALGEAINE YKGAVIVVSH    180
DARLITETNC QLWVVEEQSV SQIDGDFEDY KREVLEALGE VMVSRPRE                 228

SEQ ID NO: 7              moltype = AA  length = 269
FEATURE                   Location/Qualifiers
REGION                    1..269
                          note = Description of sequence: Nucleotide binding domain
                            of the ABCG2 gene product from UniProtKB/Swiss-Prot:
                            P45844
source                    1..269
                          mol_type = protein
                          organism = Homo sapiens
SEQUENCE: 7
RFSSLPRRAA VNIEFRDLSY SVPEGPWWRK KGYKTLLKGI SGKFNSGELV AIMGPSGAGK     60
STLMNILAGY RETGMKGAVL INGLPRDLRC FRKVSCYIMQ DDMLLPHLTV QEAMMVSAHL    120
KLQEKDEGRR EMVKEILTAL GLLSCANTRT GSLSGGQRKR LAIALELVNN PPVMFFDEPT    180
SGLDSASCFQ VVSLMKGLAQ GGRSIICTIH QPSAKLFELF DQLYVLSQGQ CVYRGKVCNL    240
VPYLRDLGLN CPTYHNPADF VMEVASGEY                                     269

SEQ ID NO: 8              moltype = AA  length = 748
FEATURE                   Location/Qualifiers
REGION                    1..748
                          note = Description of sequence: TAP1 NCBI  NP_000584.3
source                    1..748
                          mol_type = protein
                          organism = Homo sapiens
SEQUENCE: 8
MASSRCPAPR GCRCLPGASL AWLGTVLLLL ADWVLLRTAL PRIFSLLVPT ALPLLRVWAV     60
GLSRWAVLWL GACGVLRATV GSKSENAGAQ GWLAALKPLA AALGLALPGL ALFRELISWG    120
APGSADSTRL LHWGSHPTAF VVSYAAALPA AALWHKLGSL WVPGGQGSSG NPVRRLLGCL    180
GSETRRLSLF LVLVVLSSLG EMAIPFFTGR LTDWILQDGS ADTFTRNLTL MSILTIASAV    240
LEFVGDGIYN NTMGHVHSHL QGEVFGAVLR QETEFFQQNQ TGNIMSRVTE DTSTLSDSLS    300
ENLSLFLWYL VRGLCLLGIM LWGSVSLTMV TLITLPLLFL LPKKVGKWYQ LLEVQVRESL    360
AKSSQVAIEA LSAMPTVRSF ANEEGEAQKF REKLQEIKTL NQKEAVAYAV NSWTTSISGM    420
LLKVGILYIG GQLVTSGAVS SGNLVTFVLY QMQFTQAVEV LLSIYPRVQK AVGSSEKIFE    480
YLDRTPRCPP SGLLTPLHLE GLVQFQDVSF AYPNRPDVLV LQGLTFTLRP GEVTALVGPN    540
GSGKSTVAAL LQNLYQPTGG QLLLDGKPLP QYEHRYLHRQ VAAVGQEPQV FGRSLQENIA    600
YGLTQKPTME EITAAAVKSG AHSFISGLPQ GYDTEVDEAG SQLSGGQRQA VALARALIRK    660
PCVLILDDAT SALDANSQLQ VEQLLYESPE RYSRSVLLIT QHLSLVEQAD HILFLEGGAI    720
REGGTHQQLM EKKGCYWAMV QAPADAPE                                      748

SEQ ID NO: 9              moltype = AA  length = 257
FEATURE                   Location/Qualifiers
REGION                    1..257
                          note = Description of sequence: A nucleotide binding domain
                            polypeptide of wild type TAP1
source                    1..257
                          mol_type = protein
                          organism = Homo sapiens
SEQUENCE: 9
GLLTPLHLEG LVQFQDVSFA YPNRPDVLVL QGLTFTLRPG EVTALVGPNG SGKSTVAALL     60
QNLYQPTGGQ LLLDGKPLPQ YEHRYLHRQV AAVGQEPQVF GRSLQENIAY GLTQKPTMEE    120
ITAAAVKSGA HSFISGLPQG YDTEVDEAGS QLSGGQRQAV ALARALIRKP CVLILDDATS    180
ALDANSQLQV EQLLYESPER YSRSVLLITQ HLSLVEQADH ILFLEGGAIR EGGTHQQLME    240
KKGCYWAMVQ APADAPE                                                  257

SEQ ID NO: 10             moltype = AA  length = 257
FEATURE                   Location/Qualifiers
REGION                    1..257
                          note = Description of sequence: A nucleotide binding domain
                            polypeptide based on TAP1
source                    1..257
                          mol_type = protein
                          organism = Homo sapiens
SEQUENCE: 10
GLLTPLHLEG LVQFQDVSFA YPNRPDVLVL QGLTFTLRPG EVTALVGPNG SGKSTVAALL     60
QNLYQPTGGQ LLLDGKPLPQ YEHRYLHRQV AAVGQEPQVF GRSLQENIAY GLTQKPTMEE    120
ITAAAVKSGA HSFISGLPQG YDTEVDEAGS QLSGGQRQAV ALARALIRKP SVLILDNATS    180
```

```
ALDAGNQLRV QRLLYESPER YSRSVLLITQ HLSLVEQADH ILFLEGGAIR EGGTHQQLME    240
KKGSYWAMVQ APADAPE                                                   257

SEQ ID NO: 11            moltype = AA  length = 686
FEATURE                  Location/Qualifiers
REGION                   1..686
                         note = Description of sequence: Tap2  UniProtKB - Q03519
source                   1..686
                         mol_type = protein
                         organism = Homo sapiens
SEQUENCE: 11
MRLPDLRPWT SLLLVDAALL WLLQGPLGTL LPQGLPGLWL EGTLRLGGLW GLLKLRGLLG    60
FVGTLLLLPLC LATPLTVSLR ALVAGASRAP PARVASAPWS WLLVGYGAAG LSWSLWAVLS   120
PPGAQEKEQD QVNNKVLMWR LLKLSRPDLP LLVAAFFFLV LAVLGETLIP HYSGRVIDIL    180
GGDFDPHAFA SAIFFMCLFS FGSSLSAGCR GGCFTYTMSR INLRIREQLF SSLLRQDLGF    240
FQETKTGELN SRLSSDTTLM SNWLPLNANV LLRSLVKVVG LYGFMLSISP RLTLLSLLHM    300
PFTIAAEKVY NTRHQEVLRE IQDAVARAGQ VVREAVGGLQ TVRSFGAEEH EVCRYKEALE    360
QCRQLYWRRD LERALYLLVR RVLHLGVQML MLSCGLQQMQ DGELTQGSLL SFMIYQESVG    420
SYVQTLVYIY GDMLSNVGAA EKVFSYMDRQ PNLPSPGTLA PTTLQGVVKF QDVSFAYPNR    480
PDRPVLKGLT FTLRPGEVTA LVGPNGSGKS TVAALLQNLY QPTGGQVLLD EKPISQYEHC    540
YLHSQVVSVG QEPVLFSGSV RNNIAYGLQS CEDDKVMAAA QAAHADDFIQ EMEHGIYTDV    600
GEKGSQLAAG QKQRLAIARA LVRDPRVLIL DEATSALDVQ CEQALQDWNS RGDRTVLVIA    660
HRLQTVQRAH QILVLQEGKL QKLAQL                                         686

SEQ ID NO: 12            moltype = AA  length = 226
FEATURE                  Location/Qualifiers
REGION                   1..226
                         note = Description of sequence: A nucleotide binding domain
                          polypeptide of wild type TAP2
source                   1..226
                         mol_type = protein
                         organism = Homo sapiens
SEQUENCE: 12
GTLAPTTLQG VVKFQDVSFA YPNRPDRPVL KGLTFTLRPG EVTALVGPNG SGKSTVAALL    60
QNLYQPTGGQ VLLDEKPISQ YEHCYLHSQV VSVGQEPVLF SGSVRNNIAY GLQSCEDDKV   120
MAAAQAAHAD DFIQEMEHGI YTDVGEKGSQ LAAGQKQRLA IARALVRDPR VLILDEATSA   180
LDVQCEQALQ DWNSRGDRTV LVIAHRLQTV QRAHQILVLQ EGKLQK                   226

SEQ ID NO: 13            moltype = AA  length = 1480
FEATURE                  Location/Qualifiers
REGION                   1..1480
                         note = Description of sequence: NCBI Accession ABD72215.1
source                   1..1480
                         mol_type = protein
                         organism = Homo sapiens
SEQUENCE: 13
MQRSPLEKAS VVSKLFFSWT RPILRKGYRQ RLELSDIYQI PSVDSADNLS EKLEREWDRE    60
LASKKNPKLI NALRRCFFWR FMFYGIFLYL GEVTKAVQPL LLGRIIASYD PDNKEERSIA   120
IYLGIGLCLL FIVRTLLLHP AIFGLHHIGM QMRIAMFSLI YKKTLKLSSR VLDKISIGQL   180
VSLLSNNLNK FDEGLALAHF VWIAPLQVAL LMGLIWELLQ ASAFCGLGFL IVLALFQAGL   240
GRMMMKYRDQ RAGKISERLV ITSEMIENIQ SVKAYCWEEA MEKMIENLRQ TELKLTRKAA   300
YVRYFNSSAF FFSGFFVVFL SVLPYALIKG IILRKIFTTI SFCIVLRMAV TRQFPWAVQT   360
WYDSLGAINK IQDFLQKQEY KTLEYNLTTT EVVMENVTAF WEEGFGELFE KAKQNNNNRK   420
TSNGDDSLFF SNFSLLGTPV LKDINFKIER GQLLAVAGST GAGKTSLLMV IMGELEPSEG   480
KIKHSGRISF CSQFSWIMPG TIKENIIFGV SYDEYRYRSV IKACQLEEDI SKFAEKDNIV   540
LGEGGITLSG GQRARISLAR AVYKDADLYL LDSPFGYLDV LTEKEIFESC VCKLMANKTR   600
ILVTSKMEHL KKADKILILH EGSSYFYGTF SELQNLQPDF SSKLMGCDSF DQFSAERRNS   660
ILTETLHRFS LEGDAPVSWT ETKKQSFKQT GEFGEKRKNS ILNPINSIRK FSIVQKTPLQ   720
MNGIEEDSDE PLERRLSLVP DSEQGEAILP RISVISTGPT LQARRRQSVL NLMTHSVNQG   780
QNIHRKTTAS TRKVSLAPQA NLTELDIYSR RLSQETGLEI SEEINEEDLK ECFFDDMESI   840
PAVTTWNTYL RYITVHKSLI FVLIWCLVIF LAEVAASLVV LWLLGNTPLQ DKGNSTHSRN   900
NSYAVIITST SSYYVFYIYV GVADTLLAMG FFRGLPLVHT LITVSKILHH KMLHSVLQAP   960
MSTLNTLKAG GILNRFSKDI AILDDLLPLT IFDFIQLLLI VIGAIAVVAV LQPYIFVATV  1020
PVIVAFIMLR AYFLQTSQQL KQLESEGRSP IFTHLVTSLK GLWTLRAFGR QPYFETLFHK  1080
ALNLHTANWF LYLSTLRWFQ MRIEMIFVIF FIAVTFISIL TTGEGEGRVG IILTLAMNIM  1140
STLQWAVNSS IDVDSLMRSV SRVFKFIDMP TEGKPTKSTK PYKNGQLSKV MIIENSHVKK  1200
DDIWPSGGQM TVKDLTAKYT EGGNAILENI SFSISPGQRV GLLGRTGSGK STLLSAFLRL  1260
LNTEGEIQID GVSWDSITLQ QWRKAFGVIP QKVFIFSGTF RKNLDPYEQW SDQEIWKVAD  1320
EVGLRSVIEQ FPGKLDFVLV DGGCVLSHGH KQLMCLARSV LSKAKILLLD EPSAHLDPVT  1380
YQIIRRTLKQ AFADCTVILC EHRIEAMLEC QQFLVIEENK VRQYDSIQKL LNERSLFRQA  1440
ISPSDRVKLF PHRNSSKCKS KPQIAALKEE TEEEVQDTRL                        1480

SEQ ID NO: 14            moltype = AA  length = 200
FEATURE                  Location/Qualifiers
REGION                   1..200
                         note = Description of sequence: A nucleotide binding domain
                          polypeptide of the CFTR
source                   1..200
                         mol_type = protein
```

```
                            organism = Homo sapiens
SEQUENCE: 14
VLKDINFKIE RGQLLAVAGS TGAGKTSLLM VIMGELEPSE GKIKHSGRIS FCSQFSWIMP    60
GTIKENIIFG VSYDEYRYRS VIKACQLEED ISKFAEKDNI VLGEGGITLS GGQRARISLA   120
RAVYKDADLY LLDSPFGYLD VLTEKEIFES CVCKLMANKT RILVTSKMEH LKKADKILIL   180
HEGSSYFYGT FSELQNLQPD                                              200

SEQ ID NO: 15           moltype = AA  length = 229
FEATURE                 Location/Qualifiers
REGION                  1..229
                        note = Description of sequence: A nucleotide binding domain
                         polypeptide of the CFTR
source                  1..229
                        mol_type = protein
                        organism = Homo sapiens
VARIANT                 1..229
                        note = position 2 may be absent or L; position 229 is
                         absent or G
VARIANT                 2
                        note = position 2 may be absent
VARIANT                 229
                        note = position 229 may be absent
SEQUENCE: 15
SLTTTEVVME NVTAFWEEGG TPVLKDINFK IERGQLLAVA GSTGAGKTSL LMVIMGELEP    60
SEGKIKHSGR ISFCSQFSWI MPGTIKENII FGVSYDEYRY RSVIKACQLE EDISKFAEKD   120
NIVLGEGGIT LSGGQRARIS LARAVYKDAD LYLLDSPFGY LDVLTEKEIF ESCVCKLMAN   180
KTRILVTSKM EHLKKADKIL ILHEGSSYFY GTFSELQNLQ PDFSSKLMG              229

SEQ ID NO: 16           moltype = AA  length = 4
FEATURE                 Location/Qualifiers
REGION                  1..4
                        note = Description of sequence: Linker sequence
source                  1..4
                        mol_type = protein
                        organism = Homo sapiens
SEQUENCE: 16
GGGS                                                                 4

SEQ ID NO: 17           moltype = AA  length = 8
FEATURE                 Location/Qualifiers
REGION                  1..8
                        note = Description of sequence: Linker sequence
source                  1..8
                        mol_type = protein
                        organism = Homo sapiens
SEQUENCE: 17
GGGSGGGS                                                             8

SEQ ID NO: 18           moltype = AA  length = 12
FEATURE                 Location/Qualifiers
REGION                  1..12
                        note = Description of sequence: Linker sequence
source                  1..12
                        mol_type = protein
                        organism = Homo sapiens
SEQUENCE: 18
GGGSGGGSGG GS                                                       12

SEQ ID NO: 19           moltype = AA  length = 16
FEATURE                 Location/Qualifiers
REGION                  1..16
                        note = Description of sequence: Linker sequence
source                  1..16
                        mol_type = protein
                        organism = Homo sapiens
SEQUENCE: 19
GGGSGGGSGG GSGGGS                                                   16

SEQ ID NO: 20           moltype = AA  length = 20
FEATURE                 Location/Qualifiers
REGION                  1..20
                        note = Description of sequence: Linker sequence
source                  1..20
                        mol_type = protein
                        organism = Homo sapiens
SEQUENCE: 20
GGGSGGGSGG GSGGGSGGGS                                               20

SEQ ID NO: 21           moltype = AA  length = 24
```

```
FEATURE                 Location/Qualifiers
REGION                  1..24
                        note = Description of sequence: Linker sequence
source                  1..24
                        mol_type = protein
                        organism = Homo sapiens
SEQUENCE: 21
GGGSGGGSGG GSGGGSGGGS GGGS                                              24

SEQ ID NO: 22           moltype = AA  length = 24
FEATURE                 Location/Qualifiers
REGION                  1..24
                        note = Description of sequence: Linker sequence
source                  1..24
                        mol_type = protein
                        organism = Homo sapiens
SEQUENCE: 22
GGGSGGGSGG GSGGGSGGGS GGGS                                              24

SEQ ID NO: 23           moltype = AA  length = 24
FEATURE                 Location/Qualifiers
REGION                  1..24
                        note = Description of sequence: Linker sequence
source                  1..24
                        mol_type = protein
                        organism = Homo sapiens
SEQUENCE: 23
GGGSGGGSGG GSGGGSGGGS GGGS                                              24

SEQ ID NO: 24           moltype = AA  length = 28
FEATURE                 Location/Qualifiers
REGION                  1..28
                        note = Description of sequence: Linker sequence
source                  1..28
                        mol_type = protein
                        organism = Homo sapiens
SEQUENCE: 24
GGGSGGGSGG GSGGGSGGGS GGGSGGGS                                          28

SEQ ID NO: 25           moltype = AA  length = 32
FEATURE                 Location/Qualifiers
REGION                  1..32
                        note = Description of sequence: Linker sequence
source                  1..32
                        mol_type = protein
                        organism = Homo sapiens
SEQUENCE: 25
GGGSGGGSGG GSGGGSGGGS GGGSGGGSGG GS                                     32

SEQ ID NO: 26           moltype = AA  length = 5
FEATURE                 Location/Qualifiers
REGION                  1..5
                        note = Description of sequence: Linker sequence
source                  1..5
                        mol_type = protein
                        organism = Homo sapiens
SEQUENCE: 26
GGGGS                                                                   5

SEQ ID NO: 27           moltype = AA  length = 10
FEATURE                 Location/Qualifiers
REGION                  1..10
                        note = Description of sequence: Linker sequence
source                  1..10
                        mol_type = protein
                        organism = Homo sapiens
SEQUENCE: 27
GGGGSGGGGS                                                              10

SEQ ID NO: 28           moltype = AA  length = 15
FEATURE                 Location/Qualifiers
REGION                  1..15
                        note = Description of sequence: Linker sequence
source                  1..15
                        mol_type = protein
                        organism = Homo sapiens
SEQUENCE: 28
GGGGSGGGGS GGGGS                                                        15
```

```
SEQ ID NO: 29           moltype = AA  length = 20
FEATURE                 Location/Qualifiers
REGION                  1..20
                        note = Description of sequence: Linker sequence
source                  1..20
                        mol_type = protein
                        organism = Homo sapiens
SEQUENCE: 29
GGGGSGGGGS GGGGSGGGGS                                                    20

SEQ ID NO: 30           moltype = AA  length = 25
FEATURE                 Location/Qualifiers
REGION                  1..25
                        note = Description of sequence: Linker sequence
source                  1..25
                        mol_type = protein
                        organism = Homo sapiens
SEQUENCE: 30
GGGGSGGGGS GGGGSGGGGS GGGGS                                              25

SEQ ID NO: 31           moltype = AA  length = 30
FEATURE                 Location/Qualifiers
REGION                  1..30
                        note = Description of sequence: Linker sequence
source                  1..30
                        mol_type = protein
                        organism = Homo sapiens
SEQUENCE: 31
GGGGSGGGGS GGGGSGGGGS GGGGSGGGGS                                         30

SEQ ID NO: 32           moltype = AA  length = 35
FEATURE                 Location/Qualifiers
REGION                  1..35
                        note = Description of sequence: Linker sequence
source                  1..35
                        mol_type = protein
                        organism = Homo sapiens
SEQUENCE: 32
GGGGSGGGGS GGGGSGGGGS GGGGSGGGGS GGGGS                                   35

SEQ ID NO: 33           moltype = AA  length = 40
FEATURE                 Location/Qualifiers
REGION                  1..40
                        note = Description of sequence: Linker sequence
source                  1..40
                        mol_type = protein
                        organism = Homo sapiens
SEQUENCE: 33
GGGGSGGGGS GGGGSGGGGS GGGGSGGGGS GGGGSGGGGS                              40

SEQ ID NO: 34           moltype = AA  length = 45
FEATURE                 Location/Qualifiers
REGION                  1..45
                        note = Description of sequence: Linker sequence
source                  1..45
                        mol_type = protein
                        organism = Homo sapiens
SEQUENCE: 34
GGGGSGGGGS GGGGSGGGGS GGGGSGGGGS GGGGSGGGGS GGGGS                        45

SEQ ID NO: 35           moltype = AA  length = 50
FEATURE                 Location/Qualifiers
REGION                  1..50
                        note = Description of sequence: Linker sequence
source                  1..50
                        mol_type = protein
                        organism = Homo sapiens
SEQUENCE: 35
GGGGSGGGGS GGGGSGGGGS GGGGSGGGGS GGGGSGGGGS GGGGSGGGGS                   50

SEQ ID NO: 36           moltype = AA  length = 7
FEATURE                 Location/Qualifiers
REGION                  1..7
                        note = Description of sequence: Linker sequence
source                  1..7
                        mol_type = protein
                        organism = Homo sapiens
VARIANT                 1..7
                        note = position 1 may be absent or any alanine; position 7
```

```
                         is absent or alanine
VARIANT                  1
                         note = position 1 may be absent
VARIANT                  7
                         note = position 7 may be absent
SEQUENCE: 36
AEAAAKA                                                                    7

SEQ ID NO: 37            moltype = AA  length = 12
FEATURE                  Location/Qualifiers
REGION                   1..12
                         note = Description of sequence: Linker sequence
source                   1..12
                         mol_type = protein
                         organism = Homo sapiens
VARIANT                  1..12
                         note = position 1 may be absent or any alanine; position 12
                         is absent or alanine
VARIANT                  1
                         note = position 1 may be absent
VARIANT                  12
                         note = position 12 may be absent
SEQUENCE: 37
AEAAAKEAAA KA                                                             12

SEQ ID NO: 38            moltype = AA  length = 17
FEATURE                  Location/Qualifiers
REGION                   1..17
                         note = Description of sequence: Linker sequence
source                   1..17
                         mol_type = protein
                         organism = Homo sapiens
VARIANT                  1..17
                         note = position 1 may be absent or any alanine; position 17
                         is absent or alanine
VARIANT                  1
                         note = position 1 may be absent
VARIANT                  17
                         note = position 17 may be absent
SEQUENCE: 38
AEAAAKEAAA KEAAAKA                                                        17

SEQ ID NO: 39            moltype = AA  length = 22
FEATURE                  Location/Qualifiers
REGION                   1..22
                         note = Description of sequence: Linker sequence
source                   1..22
                         mol_type = protein
                         organism = Homo sapiens
VARIANT                  1..22
                         note = position 1 may be absent or any alanine; position 22
                         is absent or alanine
VARIANT                  1
                         note = position 1 may be absent
VARIANT                  22
                         note = position 22 may be absent
SEQUENCE: 39
AEAAAKEAAA KEAAAKEAAA KA                                                  22

SEQ ID NO: 40            moltype = AA  length = 27
FEATURE                  Location/Qualifiers
REGION                   1..27
                         note = Description of sequence: Linker sequence
source                   1..27
                         mol_type = protein
                         organism = Homo sapiens
VARIANT                  1..27
                         note = position 1 may be absent or any alanine; position 27
                         is absent or alanine
VARIANT                  1
                         note = position 1 may be absent
VARIANT                  27
                         note = position 27 may be absent
SEQUENCE: 40
AEAAAKEAAA KEAAAKEAAA KEAAAKA                                             27

SEQ ID NO: 41            moltype = AA  length = 33
FEATURE                  Location/Qualifiers
REGION                   1..33
```

```
                        note = Description of sequence: Linker sequence
source                  1..33
                        mol_type = protein
                        organism = Homo sapiens
VARIANT                 1..33
                        note = position 1 may be absent or any alanine; position 32
                         is absent or alanine
VARIANT                 1
                        note = position 1 may be absent
VARIANT                 33
                        note = position 33 may be absent
SEQUENCE: 41
AEAAAKEAAA KEAAAKEAAA KEAAAKKEAA AKA                                          33

SEQ ID NO: 42           moltype = AA  length = 37
FEATURE                 Location/Qualifiers
REGION                  1..37
                        note = Description of sequence: Linker sequence
source                  1..37
                        mol_type = protein
                        organism = Homo sapiens
VARIANT                 1..37
                        note = position 1 may be absent or any alanine; position 37
                         is absent or alanine
VARIANT                 1
                        note = position 1 may be absent
VARIANT                 37
                        note = position 37 may be absent
SEQUENCE: 42
AEAAAKEAAA KEAAAKEAAA KEAAAKEAAA KEAAAKA                                      37

SEQ ID NO: 43           moltype = AA  length = 42
FEATURE                 Location/Qualifiers
REGION                  1..42
                        note = Description of sequence: Linker sequence
source                  1..42
                        mol_type = protein
                        organism = Homo sapiens
VARIANT                 1..42
                        note = position 1 may be absent or any alanine; position 42
                         is absent or alanine
VARIANT                 1
                        note = position 1 may be absent
VARIANT                 42
                        note = position 42 may be absent
SEQUENCE: 43
AEAAAKEAAA KEAAAKEAAA KEAAAKEAAA KEAAAKEAAA KA                                42

SEQ ID NO: 44           moltype = AA  length = 47
FEATURE                 Location/Qualifiers
REGION                  1..47
                        note = Description of sequence: Linker sequence
source                  1..47
                        mol_type = protein
                        organism = Homo sapiens
VARIANT                 1..47
                        note = position 1 may be absent or any alanine; position 47
                         is absent or alanine
VARIANT                 1
                        note = position 1 may be absent
VARIANT                 47
                        note = position 47 may be absent
SEQUENCE: 44
AEAAAKEAAA KEAAAKEAAA KEAAAKEAAA KEAAAKEAAA KEAAAKA                           47

SEQ ID NO: 45           moltype = AA  length = 52
FEATURE                 Location/Qualifiers
REGION                  1..52
                        note = Description of sequence: Linker sequence
source                  1..52
                        mol_type = protein
                        organism = Homo sapiens
VARIANT                 1..52
                        note = position 1 may be absent or any alanine; position 52
                         is absent or alanine
VARIANT                 1
                        note = position 1 may be absent
VARIANT                 52
                        note = position 52 may be absent
```

```
SEQUENCE: 45
AEAAAKEAAA KEAAAKEAAA KEAAAKEAAA KEAAAKEAAA KEAAAKEAAA KA            52

SEQ ID NO: 46            moltype = AA  length = 57
FEATURE                  Location/Qualifiers
REGION                   1..57
                         note = Description of sequence: Linker sequence
source                   1..57
                         mol_type = protein
                         organism = Homo sapiens
VARIANT                  1..57
                         note = position 1 may be absent or any alanine; position 57
                           is absent or alanine
VARIANT                  1
                         note = position 1 may be absent
VARIANT                  57
                         note = position 57 may be absent
SEQUENCE: 46
AEAAAKEAAA KEAAAKEAAA KEAAAKEAAA KEAAAKEAAA KEAAAKEAAA KEAAAKA        57

SEQ ID NO: 47            moltype = AA  length = 62
FEATURE                  Location/Qualifiers
REGION                   1..62
                         note = Description of sequence: Linker sequence
source                   1..62
                         mol_type = protein
                         organism = Homo sapiens
VARIANT                  1..62
                         note = position 1 may be absent or any alanine; position 62
                           is absent or alanine
VARIANT                  1
                         note = position 1 may be absent
VARIANT                  62
                         note = position 62 may be absent
SEQUENCE: 47
AEAAAKEAAA KEAAAKEAAA KEAAAKEAAA KEAAAKEAAA KEAAAKEAAA KEAAAKEAAA     60
KA                                                                   62

SEQ ID NO: 48            moltype = AA  length = 67
FEATURE                  Location/Qualifiers
REGION                   1..67
                         note = Description of sequence: Linker sequence
source                   1..67
                         mol_type = protein
                         organism = Homo sapiens
VARIANT                  1..67
                         note = position 1 may be absent or any alanine; position 67
                           is absent or alanine
VARIANT                  1
                         note = position 1 may be absent
VARIANT                  67
                         note = position 67 may be absent
SEQUENCE: 48
AEAAAKEAAA KEAAAKEAAA KEAAAKEAAA KEAAAKEAAA KEAAAKEAAA KEAAAKEAAA     60
KEAAAKA                                                              67

SEQ ID NO: 49            moltype = AA  length = 72
FEATURE                  Location/Qualifiers
REGION                   1..72
                         note = Description of sequence: Linker sequence
source                   1..72
                         mol_type = protein
                         organism = Homo sapiens
VARIANT                  1..72
                         note = position 1 may be absent or any alanine; position 72
                           is absent or alanine
VARIANT                  1
                         note = position 1 may be absent
VARIANT                  72
                         note = position 72 may be absent
SEQUENCE: 49
AEAAAKEAAA KEAAAKEAAA KEAAAKEAAA KEAAAKEAAA KEAAAKEAAA KEAAAKEAAA     60
KEAAAKEAAA KA                                                        72

SEQ ID NO: 50            moltype = AA  length = 77
FEATURE                  Location/Qualifiers
REGION                   1..77
                         note = Description of sequence: Linker sequence
source                   1..77
```

```
                           mol_type = protein
                           organism = Homo sapiens
VARIANT                    1..77
                           note = position 1 may be absent or any alanine; position 77
                             is absent or alanine
VARIANT                    1
                           note = position 1 may be absent
VARIANT                    77
                           note = position 77 may be absent
SEQUENCE: 50
AEAAAKEAAA KEAAAKEAAA KEAAAKEAAA KEAAAKEAAA KEAAAKEAAA KEAAAKEAAA    60
KEAAAKEAAA KEAAAKA                                                   77

SEQ ID NO: 51              moltype = AA  length = 82
FEATURE                    Location/Qualifiers
REGION                     1..82
                           note = Description of sequence: Linker sequence
source                     1..82
                           mol_type = protein
                           organism = Homo sapiens
VARIANT                    1..82
                           note = position 1 may be absent or any alanine; position 82
                             is absent or alanine
VARIANT                    1
                           note = position 1 may be absent
VARIANT                    82
                           note = position 82 may be absent
SEQUENCE: 51
AEAAAKEAAA KEAAAKEAAA KEAAAKEAAA KEAAAKEAAA KEAAAKEAAA KEAAAKEAAA    60
KEAAAKEAAA KEAAAKEAAA KA                                             82

SEQ ID NO: 52              moltype = AA  length = 87
FEATURE                    Location/Qualifiers
REGION                     1..87
                           note = Description of sequence: Linker sequence
source                     1..87
                           mol_type = protein
                           organism = Homo sapiens
VARIANT                    1..87
                           note = position 1 may be absent or any alanine; position 87
                             is absent or alanine
VARIANT                    1
                           note = position 1 may be absent
VARIANT                    87
                           note = position 87 may be absent
SEQUENCE: 52
AEAAAKEAAA KEAAAKEAAA KEAAAKEAAA KEAAAKEAAA KEAAAKEAAA KEAAAKEAAA    60
KEAAAKEAAA KEAAAKEAAA KEAAAKA                                        87

SEQ ID NO: 53              moltype = AA  length = 92
FEATURE                    Location/Qualifiers
REGION                     1..92
                           note = Description of sequence: Linker sequence
source                     1..92
                           mol_type = protein
                           organism = Homo sapiens
VARIANT                    1..92
                           note = position 1 may be absent or any alanine; position 92
                             is absent or alanine
VARIANT                    1
                           note = position 1 may be absent
VARIANT                    92
                           note = position 92 may be absent
SEQUENCE: 53
AEAAAKEAAA KEAAAKEAAA KEAAAKEAAA KEAAAKEAAA KEAAAKEAAA KEAAAKEAAA    60
KEAAAKEAAA KEAAAKEAAA KEAAAKEAAA KA                                  92

SEQ ID NO: 54              moltype = AA  length = 97
FEATURE                    Location/Qualifiers
REGION                     1..97
                           note = Description of sequence: Linker sequence
source                     1..97
                           mol_type = protein
                           organism = Homo sapiens
VARIANT                    1..97
                           note = position 1 may be absent or any alanine; position 97
                             is absent or alanine
VARIANT                    1
                           note = position 1 may be absent
```

```
VARIANT                      97
                             note = position 97 may be absent
SEQUENCE: 54
AEAAAKEAAA  KEAAAKEAAA  KEAAAKEAAA  KEAAAKEAAA  KEAAAKEAAA   60
KEAAAKEAAA  KEAAAKEAAA  KEAAAKEAAA  KEAAAKA                  97

SEQ ID NO: 55                moltype = AA  length = 102
FEATURE                      Location/Qualifiers
REGION                       1..102
                             note = Description of sequence: Linker sequence
source                       1..102
                             mol_type = protein
                             organism = Homo sapiens
VARIANT                      1..102
                             note = position 1 may be absent or any alanine; position
                              102 is absent or alanine
VARIANT                      1
                             note = position 1 may be absent
VARIANT                      102
                             note = position 102 may be absent
SEQUENCE: 55
AEAAAKEAAA  KEAAAKEAAA  KEAAAKEAAA  KEAAAKEAAA  KEAAAKEAAA   60
KEAAAKEAAA  KEAAAKEAAA  KEAAAKEAAA  KEAAAKEAAA  KA          102

SEQ ID NO: 56                moltype = AA  length = 227
FEATURE                      Location/Qualifiers
REGION                       1..227
                             note = Description of sequence: WT Homo sapiens IgG1 Fc
                              Sequence
source                       1..227
                             mol_type = protein
                             organism = Homo sapiens
SEQUENCE: 56
DKTHTCPPCP  APELLGGPSV  FLFPPKPKDT  LMISRTPEVT  CVVVDVSHED  PEVKFNWYVD   60
GVEVHNAKTK  PREEQYNSTY  RVVSVLTVLH  QDWLNGKEYK  CKVSNKALPA  PIEKTISKAK  120
GQPREPQVYT  LPPSREEMTK  NQVSLTCLVK  GFYPSDIAVE  WESNGQPENN  YKTTPPVLDS  180
DGSFFLYSKL  TVDKSRWQQG  NVFSCSVMHE  ALHNHYTQKS  LSLSPGK                227

SEQ ID NO: 57                moltype = AA  length = 226
FEATURE                      Location/Qualifiers
REGION                       1..226
                             note = Description of sequence: hIgG1 Fc with LALA
                              substitution
source                       1..226
                             mol_type = protein
                             organism = Homo sapiens
SEQUENCE: 57
DKTHTCPPCP  APEAAGGPSV  FLFPPKPKDT  LMISRTPEVT  CVVVDVSHED  PEVKFNWYVD   60
GVEVHNAKTK  PREEQYNSTY  RVVSVLTVLH  QDWLNGKEYK  CKVSNKALPA  PIEKTISKAK  120
GQPREPQVYT  LPPSRDELTK  NQVSLTCLVK  GFYPSDIAVE  WESNGQPENN  YKTTPPVLDS  180
DGSFFLYSKL  TVDKSRWQQG  NVFSCSVMHE  ALHNHYTQKS  LSLSPG                 226

SEQ ID NO: 58                moltype = AA  length = 325
FEATURE                      Location/Qualifiers
REGION                       1..325
                             note = Description of sequence: Homo sapiens IgG2 Fc
                              GenBank AAN76044
source                       1..325
                             mol_type = protein
                             organism = Homo sapiens
SEQUENCE: 58
STKGPSVFPL  APCSRSTSES  TAALGCLVKD  YFPEPVTVSW  NSGALTSGVH  TFPAVLQSSG   60
LYSLSSVVTV  PSSNFGTQTY  TCNVDHKPSN  TKVDKTVERK  CCVECPPCPA  PPVAGPSVFL  120
FPPKPKDTLM  ISRTPEVTCV  VVDVSHEDPE  VQFNWYVDGV  EVHNAKTKPR  EEQFNSTFRV  180
VSVLTVVHQD  WLNGKEYKCK  VSNKGLPAPI  EKTISKTKGQ  PREPQVYTLP  PSREEMTKNQ  240
VSLTCLVKGF  YPSDIAVEWE  SNGQPENNYK  TTPPMLDSDG  SFFLYSKLTV  DKSRWQQGNV  300
FSCSVMHEAL  HNHYTQKSLS  LSPGK                                         325

SEQ ID NO: 59                moltype = AA  length = 246
FEATURE                      Location/Qualifiers
REGION                       1..246
                             note = Description of sequence: Homo sapiens IgG3 Fc
                              GenBank AAW65947
source                       1..246
                             mol_type = protein
                             organism = Homo sapiens
SEQUENCE: 59
HKPSNTKVDK  RVELKTPLGD  TTHTCPPCPA  PELLGGPSVF  LFPPKPKDTL  MISRTPEVTC   60
VVVDVSHEDP  EVKFNWYVDG  VEVHNAKTKP  REEQYNSTYR  VVSVLTVLHQ  DWLNGKEYKC  120
```

```
KVSNKALPAP IEKTISKAKG QPREPQVYTL PPSRDELTKN QVSLTCLVKG FYPSDIAVEW    180
ESNGQPENNY KTTPPVLDSD GSFFLYSKLT VDKSRWQQGN VFSCSVMHEA LHNHYTQKSL    240
SLSPGK                                                                246

SEQ ID NO: 60              moltype = AA  length = 223
FEATURE                    Location/Qualifiers
REGION                     1..223
                           note = Description of sequence: Homo sapiens IgG4 Fc
                           Segment
source                     1..223
                           mol_type = protein
                           organism = Homo sapiens
SEQUENCE: 60
PPCPSCPAPE FLGGPSVFLF PPKPKDTLMI SRTPEVTCVV VDVSQEDPEV QFNWYVDGVE     60
VHNAKTKPRE EQFNSTYRVV SVLTVLHQDW LNGKEYKCKV SNKGLPSSIE KTISKAKGQP    120
REPQVYTLPP SQEEMTKNQV SLTCLVKGFY PSDIAVEWES NGQPENNYKT TPPVLDSDGS    180
FFLYSRLTVD KSRWQEGNVF SCSVMHEALH NHYTQKSLSL SPG                      223

SEQ ID NO: 61              moltype = AA  length = 253
FEATURE                    Location/Qualifiers
REGION                     1..253
                           note = Description of sequence: A scFv anti-human CD3
source                     1..253
                           mol_type = protein
                           organism = Homo sapiens
SEQUENCE: 61
AIQMTQSPSS LSASVGDRVT ITCRASQDIR NYLNWYQQKP GKAPKLLIYY TSRLESGVPS     60
RFSGSGSGTD YTLTISSLQP EDFATYYCQQ GNTLPWTFGQ GTKVEIKGGG GSGGGGSGGG    120
GSGGGGSGGG SEVQLVESGG GLVQPGGSLR LSCAASGYSF TGYTMNWVRQ APGKGLEWVA    180
LINPYKGVTT YADSVKGRFT ISVDKSKNTA YLQMNSLRAE DTAVYYCARS GYYGDSDWYF    240
DVWGQGTLVT VSS                                                       253

SEQ ID NO: 62              moltype = AA  length = 253
FEATURE                    Location/Qualifiers
REGION                     1..253
                           note = Description of sequence: A scFv anti-human CD3
source                     1..253
                           mol_type = protein
                           organism = Homo sapiens
SEQUENCE: 62
AIQMTQSPSS LSASVGDRVT ITCRASQDIR NYLNWYQQKP GKAPKLLIYY TSRLESGVPS     60
RFSGSGSGTD YTLTISSLQP EDFATYYCQQ GNTLPWTFGQ GTKVEIKGGG GSGGGGSGGG    120
GSGGGGSGGG SEVQLVESGG GLVQPGGSLR LSCAASGYSF TGYTMNWVRQ APGKGLEWVA    180
LINPYKGVST YNQKFKDRFT ISVDKSKNTA YLQMNSLRAE DTAVYYCARS GYYGDSDWYF    240
DVWGQGTLVT VSS                                                       253

SEQ ID NO: 63              moltype = AA  length = 115
FEATURE                    Location/Qualifiers
REGION                     1..115
                           note = Description of sequence: An anti-human CD3 VHH
source                     1..115
                           mol_type = protein
                           organism = Homo sapiens
SEQUENCE: 63
QVQLVESGGG LVQPGGSLRL SCAASGSIFS ANTMGWYRQA PGKQRELVAG MNTSGSTVYG     60
DSVKGRFTIS RDNAKNIAYL QMNSLIPEDT AVYYCTLVQR GPNYWGQGTQ VTVSS         115

SEQ ID NO: 64              moltype = AA  length = 240
FEATURE                    Location/Qualifiers
REGION                     1..240
                           note = Description of sequence: An anti-human CD3 scFv
                           (vH-vL)
source                     1..240
                           mol_type = protein
                           organism = Homo sapiens
SEQUENCE: 64
DVQLVQSGAE VKKPGASVKV SCKASGYTFT RYTMHWVRQA PGQGLEWIGY INPSRGYTNY     60
ADSVKGRFTI TTDKSTSTAY MELSSLRSED TATYYCARYY DDHYCLDYWG QGTTVTVSSG    120
GGSGGGGSG GGGSDIVLTQ SPATLSLSPG ERATLSCRAS QSVSYMNWYQ QKPGKAPKRW    180
IYDTSKVASG VPARFSGSGS GTDYSLTINS LEAEDAATYY CQQWSSNPLT FGGGTKVEIK    240

SEQ ID NO: 65              moltype = AA  length = 240
FEATURE                    Location/Qualifiers
REGION                     1..240
                           note = Description of sequence: An anti-human CD3 scFv
                           (vH-vL) with disulfide linkage
source                     1..240
                           mol_type = protein
                           organism = Homo sapiens
```

```
DISUFID                 43..233
                        note = Disufide bond between POS 43 and POS 233
SEQUENCE: 65
DVQLVQSGAE VKKPGASVKV SCKASGYTFT RYTMHWVRQA PGCGLEWIGY INPSRGYTNY  60
ADSVKGRFTI TTDKSTSTAY MELSSLRSED TATYYCARYY DDHYCLDYWG QGTTVTVSSG 120
GGGSGGGGSG GGGSDIVLTQ SPATLSLSPG ERATLSCRAS QSVSYMNWYQ QKPGKAPKRW 180
IYDTSKVASG VPARFSGSGS GTDYSLTINS LEAEDAATYY CQQWSSNPLT FGCGTKVEIK 240

SEQ ID NO: 66           moltype = AA  length = 240
FEATURE                 Location/Qualifiers
REGION                  1..240
                        note = Description of sequence: An anti-human CD3 scFv
                         (vH-vL) with disulfide linkage
source                  1..240
                        mol_type = protein
                        organism = Homo sapiens
DISUFID                 43..234
                        note = Disufide bond between POS 43 and POS 234
SEQUENCE: 66
DVQLVQSGAE VKKPGASVKV SCKASGYTFT RYTMHWVRQA PGCGLEWIGY INPSRGYTNY  60
ADSVKGRFTI TTDKSTSTAY MELSSLRSED TATYYCARYY DDHYCLDYWG QGTTVTVSSG 120
GGGSGGGGSG GGGSDIVLTQ SPATLSLSPG ERATLSCRAS QSVSYMNWYQ QKPGKAPKRW 180
IYDTSKVASG VPARFSGSGS GTDYSLTINS LEAEDAATYY CQQWSSNPLT FGCTKVEIK  240

SEQ ID NO: 67           moltype = AA  length = 240
FEATURE                 Location/Qualifiers
REGION                  1..240
                        note = Description of sequence: An anti-human CD3 scFv
                         (vH-vL) with disulfide linkage
source                  1..240
                        mol_type = protein
                        organism = Homo sapiens
DISUFID                 44..233
                        note = Disufide bond between POS 44 and POS 233
SEQUENCE: 67
DVQLVQSGAE VKKPGASVKV SCKASGYTFT RYTMHWVRQA PGQCLEWIGY INPSRGYTNY  60
ADSVKGRFTI TTDKSTSTAY MELSSLRSED TATYYCARYY DDHYCLDYWG QGTTVTVSSG 120
GGGSGGGGSG GGGSDIVLTQ SPATLSLSPG ERATLSCRAS QSVSYMNWYQ QKPGKAPKRW 180
IYDTSKVASG VPARFSGSGS GTDYSLTINS LEAEDAATYY CQQWSSNPLT FGCGTKVEIK 240

SEQ ID NO: 68           moltype = AA  length = 240
FEATURE                 Location/Qualifiers
REGION                  1..240
                        note = Description of sequence: An anti-human CD3 scFv
                         (vH-vL) with disulfide linkage
source                  1..240
                        mol_type = protein
                        organism = Homo sapiens
DISUFID                 44..234
                        note = Disufide bond between POS 44 and POS 234
SEQUENCE: 68
DVQLVQSGAE VKKPGASVKV SCKASGYTFT RYTMHWVRQA PGQCLEWIGY INPSRGYTNY  60
ADSVKGRFTI TTDKSTSTAY MELSSLRSED TATYYCARYY DDHYCLDYWG QGTTVTVSSG 120
GGGSGGGGSG GGGSDIVLTQ SPATLSLSPG ERATLSCRAS QSVSYMNWYQ QKPGKAPKRW 180
IYDTSKVASG VPARFSGSGS GTDYSLTINS LEAEDAATYY CQQWSSNPLT FGGCTKVEIK 240

SEQ ID NO: 69           moltype = DNA  length = 24
FEATURE                 Location/Qualifiers
source                  1..24
                        mol_type = other DNA
                        organism = synthetic construct
misc_feature            1..24
                        note = Description of sequence: Enzyme:Oligonucleotide
                         IMT504
SEQUENCE: 69
tcatcatttt gtcattttgt catt                                         24

SEQ ID NO: 70           moltype = AA  length = 240
FEATURE                 Location/Qualifiers
REGION                  1..240
                        note = Description of sequence: An anti-mesothelin scFv
                         polypeptide related to the murine-derived SS1 antibody
source                  1..240
                        mol_type = protein
                        organism = Homo sapiens
VARIANT                 121
                        note = X is V or G
SEQUENCE: 70
QVQLQQSGPE LEKPGASVKI SCKASGYSFT GYTMNWVKQS HGKSLEWIGL ITPYNGASSY  60
```

```
NQKFRGKATL TVDKSSSTAY MDLLSLTSED SAVYFCARGG YDGRGFDYWG SGTPVTVSSG    120
XGGSGGGGSG GGGSDIELTQ SPAIMSASPG EKVTMTCSAS SSVSYMHWYQ QKSGTSPKRW    180
IYDTSKLASG VPGRFSGSGS GNSYSLTISS VEAEDDATYY CQQWSKHPLT FGSGTKVEIK    240

SEQ ID NO: 71              moltype = AA   length = 244
FEATURE                    Location/Qualifiers
REGION                     1..244
                           note = Description of sequence: An anti-human mesothelin
                            scFv (vH-vL) polypeptide related to the monoclonal
                            antibody YP218
source                     1..244
                           mol_type = protein
                           organism = Homo sapiens
VARIANT                    121
                           note = X is V or G
SEQUENCE: 71
QEQLVESGGG LVQPGASLTL TCTASGIDFS RYYMCWVRQA PGKGLEGIAC IYIGGSGSTY     60
YASWAKGRFT ISKASSTTVT LQMTSLTAAD TATYFCARGT NLNYIFRLWG PGTLVTVSSG    120
XGGSGGGGSG GGGSDVVMTQ TPASVSEPVG GTVTIKCQAS QRISSYLSWY QQKPGQRPKL    180
LIFGASTLAS GVPSRFKGSG SGTEYTLTIS DLECADAATY YCQSYAYFDS NNWHAFGGGT    240
EVVV                                                                 244

SEQ ID NO: 72              moltype = AA   length = 244
FEATURE                    Location/Qualifiers
REGION                     1..244
                           note = Description of sequence: An anti-human mesothelin
                            scFv (vL-vH) polypeptide related to the monoclonal
                            antibody YP218
source                     1..244
                           mol_type = protein
                           organism = Homo sapiens
VARIANT                    112
                           note = X is V or G
SEQUENCE: 72
DVVMTQTPAS VSEPVGGTVT IKCQASQRIS SYLSWYQQKP GQRPKLLIFG ASTLASGVPS     60
RFKGSGSGTE YTLTISDLEC ADAATYYCQS YAYFDSNNWH AFGGGTEVVV GXGGSGGGGS    120
GGGGSQEQLV ESGGGLVQPG ASLTLTCTAS GIDFSRYYMC WVRQAPGKGL EGIACIYIGG    180
SGSTYYASWA KGRFTISKAS STTVTLQMTS LTAADTATYF CARGTNLNYI FRLWGPGTLV    240
TVSS                                                                 244

SEQ ID NO: 73              moltype = AA   length = 239
FEATURE                    Location/Qualifiers
REGION                     1..239
                           note = Description of sequence: An anti-human mesothelin
                            scFv (vH-vL) polypeptide related to the monoclonal
                            antibody 15B6
source                     1..239
                           mol_type = protein
                           organism = Homo sapiens
VARIANT                    116
                           note = X is V or G
SEQUENCE: 73
EVQLQQSGPV LVKPGASVKI SCKASGYSFT GYYMHWVRQS NGKSLEWIGR INPYTGVPSY     60
KHNFKDKASL TVDKSSSTAY MELHSLTSED SAVYYCAREL GGYWGQGTTL TVSSGXGGSG    120
GGGSGGGGSQ AVVTQESALT TSPGETVTLT CRSSTGAVTT GNYPNWVQEK PDHLFTGLIA    180
GTNNRAPGVP ARFSGSLIGD KAALTITGAQ TEDEAIYFCA LWFSSHWVFG GGTKLTVLG     239

SEQ ID NO: 74              moltype = AA   length = 239
FEATURE                    Location/Qualifiers
REGION                     1..239
                           note = Description of sequence: An anti-human mesothelin
                            scFv (vL-vH) polypeptide related to the monoclonal
                            antibody 15B6
source                     1..239
                           mol_type = protein
                           organism = Homo sapiens
VARIANT                    112
                           note = X is V or G
SEQUENCE: 74
QAVVTQESAL TTSPGETVTL TCRSSTGAVT TGNYPNWVQE KPDHLFTGLI AGTNNRAPGV     60
PARFSGSLIG DKAALTITGA QTEDEAIYFC ALWFSSHWVF GGGTKLTVLG GXGGSGGGGS    120
GGGGSEVQLQ QSGPVLVKPG ASVKISCKAS GYSFTGYYMH WVRQSNGKSL EWIGRINPYT    180
GVPSYKHNFK DKASLTVDKS SSTAYMELHS LTSEDSAVYY CARELGGYWG QGTTLTVSS     239

SEQ ID NO: 75              moltype = AA   length = 239
FEATURE                    Location/Qualifiers
REGION                     1..239
                           note = Description of sequence: An anti-human mesothelin
                            scFv (vL-vH) polypeptide related to the monoclonal
```

|   |   |
|---|---|
|   | antibody 15B6 with a disulfide linkage |
| source | 1..239 |
|   | mol_type = protein |
|   | organism = Homo sapiens |
| DISULFID | 102..168 |
|   | note = Disulfide bond between POS 102 and POS 168 |

SEQUENCE: 75
```
QAVVTQESAL TTSPGETVTL TCRSSTGAVT TGNYPNWVQE KPDHLFTGLI AGTNNRAPGV   60
PARFSGSLIG DKAALTITGA QTEDEAIYFC ALWFSSHWVF GCGTKLTVLG GGGGSGGGGS  120
GGGGSEVQLQ QSGPVLVKPG ASVKISCKAS GYSFTGYYMH WVRQSNGCSL EWIGRINPYT  180
GVPSYKHNFK DKASLTVDKS SSTAYMELHS LTSEDSAVYY CARELGGYWG QGTTLTVSS   239
```

|   |   |
|---|---|
| SEQ ID NO: 76 | moltype = AA  length = 239 |
| FEATURE | Location/Qualifiers |
| REGION | 1..239 |
|   | note = Description of sequence: An anti-human mesothelin scFv (vL-vH) polypeptide related to the monoclonal antibody 15B6 with a disulfide linkage |
| source | 1..239 |
|   | mol_type = protein |
|   | organism = Homo sapiens |
| DISULFID | 102..169 |
|   | note = Disulfide bond between POS 102 and POS 169 |

SEQUENCE: 76
```
QAVVTQESAL TTSPGETVTL TCRSSTGAVT TGNYPNWVQE KPDHLFTGLI AGTNNRAPGV   60
PARFSGSLIG DKAALTITGA QTEDEAIYFC ALWFSSHWVF GCGTKLTVLG GGGGSGGGGS  120
GGGGSEVQLQ QSGPVLVKPG ASVKISCKAS GYSFTGYYMH WVRQSNGKCL EWIGRINPYT  180
GVPSYKHNFK DKASLTVDKS SSTAYMELHS LTSEDSAVYY CARELGGYWG QGTTLTVSS   239
```

|   |   |
|---|---|
| SEQ ID NO: 77 | moltype = AA  length = 239 |
| FEATURE | Location/Qualifiers |
| REGION | 1..239 |
|   | note = Description of sequence: An anti-human mesothelin scFv (vL-vH) polypeptide related to the monoclonal antibody 15B6 with a disulfide linkage |
| source | 1..239 |
|   | mol_type = protein |
|   | organism = Homo sapiens |
| DISULFID | 103..168 |
|   | note = Disulfide bond between POS 103 and POS 168 |

SEQUENCE: 77
```
QAVVTQESAL TTSPGETVTL TCRSSTGAVT TGNYPNWVQE KPDHLFTGLI AGTNNRAPGV   60
PARFSGSLIG DKAALTITGA QTEDEAIYFC ALWFSSHWVF GGCTKLTVLG GGGGSGGGGS  120
GGGGSEVQLQ QSGPVLVKPG ASVKISCKAS GYSFTGYYMH WVRQSNGCSL EWIGRINPYT  180
GVPSYKHNFK DKASLTVDKS SSTAYMELHS LTSEDSAVYY CARELGGYWG QGTTLTVSS   239
```

|   |   |
|---|---|
| SEQ ID NO: 78 | moltype = AA  length = 238 |
| FEATURE | Location/Qualifiers |
| REGION | 1..238 |
|   | note = Description of sequence: An anti-human mesothelin scFv (vL-vH) polypeptide related to the monoclonal antibody 15B6 with a disulfide linkage |
| source | 1..238 |
|   | mol_type = protein |
|   | organism = Homo sapiens |
| DISULFID | 103..169 |
|   | note = Disulfide bond between POS 103 and POS 169 |

SEQUENCE: 78
```
QAVVTQESAL TTSPGETVTL TCRSSTGAVT TGNYPNWVQE KPDHLFTGLI AGTNNRAPGV   60
PARFSGSLIG DKAALTITGA QTEDEAIYFC ALWFSSHWVF GGCTKLTVLG GGGGSGGGGS  120
GGGGSEVQLQ QSGPVLVKPG ASVKISCKAS GYSFTGYYMH WVRQSNGKCL EWIGRINPYT  180
GVPSYKHNFK DKASLTVDKS SSTAYMELHS LTSEDSAVYY CARELGGYWG QGTTLTVS    238
```

|   |   |
|---|---|
| SEQ ID NO: 79 | moltype = AA  length = 113 |
| FEATURE | Location/Qualifiers |
| REGION | 1..113 |
|   | note = Description of sequence: An anti-human mesothelin (VHH) polypeptide related to the monoclonal antibody SD1 |
| source | 1..113 |
|   | mol_type = protein |
|   | organism = Homo sapiens |

SEQUENCE: 79
```
QVQLVQSGGG LVQPGGSLRL SCAASDFDFA AYEMSWVRQA PGQGLEWVAI ISHDGIDKYY   60
TDSVKGRFTI SRDNSKNTLY LQMNTLRAED TATYYCLRLG AVGQGTLVTV SSS         113
```

|   |   |
|---|---|
| SEQ ID NO: 80 | moltype = AA  length = 252 |
| FEATURE | Location/Qualifiers |
| REGION | 1..252 |
|   | note = Description of sequence: An anti-human EpCAM scFv |

```
                        (vH-vL) polypeptide related to the monoclonal antibody
                        MT201
source                  1..252
                        mol_type = protein
                        organism = Homo sapiens
VARIANT                 129
                        note = X is V or G
SEQUENCE: 80
EVQLLESGGG VVQPGRSLRL SCAASGFTFS SYGMHWVRQA PGKGLEWVAV ISYDGSNKYY      60
ADSVKGRFTI SRDNSKNTLY LQMNSLRAED TAVYYCAKDM GWGSGWRPYY YYGMDVWGQG     120
TTVTVSSGXG GSGGGGSGGG GSELQMTQSP SSLSASVGDR VTITCRTSQS ISSYLNWYQQ     180
KPGQPPKLLI YWASTRESGV PDRFSGSGSG TDFTLTISSL QPEDSATYYC QQSYDIPYTF     240
GQGTKLEIKR TV                                                        252

SEQ ID NO: 81           moltype = AA  length = 252
FEATURE                 Location/Qualifiers
REGION                  1..252
                        note = Description of sequence: An anti-human EpCAM scFv
                        (vL-vH) polypeptide related to the monoclonal antibody
                        MT201
source                  1..252
                        mol_type = protein
                        organism = Homo sapiens
VARIANT                 112
                        note = X is V or G
SEQUENCE: 81
ELQMTQSPSS LSASVGDRVT ITCRTSQSIS SYLNWYQQKP GQPPKLLIYW ASTRESGVPD      60
RFSGSGSGTD FTLTISSLQP EDSATYYCQQ SYDIPYTFGQ GTKLEIKRTV GXGGSGGGGS     120
GGGGSEVQLL ESGGGVVQPG RSLRLSCAAS GFTFSSYGMH WVRQAPGKGL EWVAVISYDG     180
SNKYYADSVK GRFTISRDNS KNTLYLQMNS LRAEDTAVYY CAKDMGWGSG WRPYYYYGMD     240
VWGQGTTVTV SS                                                        252

SEQ ID NO: 82           moltype = AA  length = 242
FEATURE                 Location/Qualifiers
REGION                  1..242
                        note = Description of sequence: An anti-human CTLA-4 scFv
                        (vL-vH) polypeptide related to Ipilimumab
source                  1..242
                        mol_type = protein
                        organism = Homo sapiens
SEQUENCE: 82
EIVLTQSPGT LSLSPGERAT LSCRASQSVG SSYLAWYQQK PGQAPRLLIY GAFSRATGIP      60
DRFSGSGSGT DFTLTISRLE PEDFAVYYCQ QYGSSPWTFG QGTKVEIKRG GGGSGGGGSG     120
GGGSQVQLVE SGGGVVQPGR SLRLSCAASG FTFSSYTMHW VRQAPGKGLE WVTFISYDGN     180
NKYYADSVKG RFTISRDNSK NTLYLQMNSL RAEDTAIYYC ARTGWLGPFD YWGQGTLVTV     240
SS                                                                   242

SEQ ID NO: 83           moltype = AA  length = 242
FEATURE                 Location/Qualifiers
REGION                  1..242
                        note = Description of sequence: An anti-human CTLA-4 scFv
                        (vL-vH) polypeptide related to Ipilimumab with a disulfide
                        linkage
source                  1..242
                        mol_type = protein
                        organism = Homo sapiens
DISULFID                101..167
                        note = Disulfide bond between POS 101 and POS 167
SEQUENCE: 83
EIVLTQSPGT LSLSPGERAT LSCRASQSVG SSYLAWYQQK PGQAPRLLIY GAFSRATGIP      60
DRFSGSGSGT DFTLTISRLE PEDFAVYYCQ QYGSSPWTFG CGTKVEIKRG GGGSGGGGSG     120
GGGSQVQLVE SGGGVVQPGR SLRLSCAASG FTFSSYTMHW VRQAPGCGLE WVTFISYDGN     180
NKYYADSVKG RFTISRDNSK NTLYLQMNSL RAEDTAIYYC ARTGWLGPFD YWGQGTLVTV     240
SS                                                                   242

SEQ ID NO: 84           moltype = AA  length = 242
FEATURE                 Location/Qualifiers
REGION                  1..242
                        note = Description of sequence: An anti-human CTLA-4 scFv
                        (vL-vH) polypeptide related to Ipilimumab with a disulfide
                        linkage
source                  1..242
                        mol_type = protein
                        organism = Homo sapiens
DISULFID                101..168
                        note = Disulfide bond between POS 101 and POS 168
SEQUENCE: 84
EIVLTQSPGT LSLSPGERAT LSCRASQSVG SSYLAWYQQK PGQAPRLLIY GAFSRATGIP      60
DRFSGSGSGT DFTLTISRLE PEDFAVYYCQ QYGSSPWTFG CGTKVEIKRG GGGSGGGGSG     120
```

```
GGGSQVQLVE SGGGVVQPGR SLRLSCAASG FTFSSYTMHW VRQAPGKCLE WVTFISYDGN    180
NKYYADSVKG RFTISRDNSK NTLYLQMNSL RAEDTAIYYC ARTGWLGPFD YWGQGTLVTV    240
SS                                                                  242

SEQ ID NO: 85           moltype = AA   length = 242
FEATURE                 Location/Qualifiers
REGION                  1..242
                        note = Description of sequence: An anti-human CTLA-4 scFv
                         (vL-vH) polypeptide related to Ipilimumab with a disulfide
                         linkage
source                  1..242
                        mol_type = protein
                        organism = Homo sapiens
DISULFID                102..167
                        note = Disulfide bond between POS 102 and POS 167
SEQUENCE: 85
EIVLTQSPGT LSLSPGERAT LSCRASQSVG SSYLAWYQQK PGQAPRLLIY GAFSRATGIP    60
DRFSGSGSGT DFTLTISRLE PEDFAVYYCQ QYGSSPWTFG QCTKVEIKRG GGGSGGGGSG    120
GGGSQVQLVE SGGGVVQPGR SLRLSCAASG FTFSSYTMHW VRQAPGCGLE WVTFISYDGN    180
NKYYADSVKG RFTISRDNSK NTLYLQMNSL RAEDTAIYYC ARTGWLGPFD YWGQGTLVTV    240
SS                                                                  242

SEQ ID NO: 86           moltype = AA   length = 242
FEATURE                 Location/Qualifiers
REGION                  1..242
                        note = Description of sequence: An anti-human CTLA-4 scFv
                         (vL-vH) polypeptide related to Ipilimumab with a disulfide
                         linkage
source                  1..242
                        mol_type = protein
                        organism = Homo sapiens
DISULFID                102..168
                        note = Disulfide bond between POS 102 and POS 168
SEQUENCE: 86
EIVLTQSPGT LSLSPGERAT LSCRASQSVG SSYLAWYQQK PGQAPRLLIY GAFSRATGIP    60
DRFSGSGSGT DFTLTISRLE PEDFAVYYCQ QYGSSPWTFG QCTKVEIKRG GGGSGGGGSG    120
GGGSQVQLVE SGGGVVQPGR SLRLSCAASG FTFSSYTMHW VRQAPGKCLE WVTFISYDGN    180
NKYYADSVKG RFTISRDNSK NTLYLQMNSL RAEDTAIYYC ARTGWLGPFD YWGQGTLVTV    240
SS                                                                  242

SEQ ID NO: 87           moltype = AA   length = 261
FEATURE                 Location/Qualifiers
REGION                  1..261
                        note = Description of sequence: A nucleotide binding domain
                         polypeptide based on TAP1
source                  1..261
                        mol_type = protein
                        organism = Homo sapiens
SEQUENCE: 87
MPPSGLLTPL HLEGLVQFQD VSFAYPNRPD VLVLQGLTFT LRPGEVTALV GPNGSGKSTV    60
AALLQNLYQP TGGQLLLDGK PLPQYEHRYL HRQVAAVGQE PQVFGRSLQE NIAYGLTQKP    120
TMEEITAAAV KSGAHSFISG LPQGYDTEVD EAGSQLSGGQ RQAVALARAL IRKPSVLILD    180
NATSALDAGN QLRVQRLLYE SPERYSRSVL LITQHLSLVE QADHILFLEG GAIREGGTHQ    240
QLMEKKGSYW AMVQAPADAP E                                             261

SEQ ID NO: 88           moltype = AA   length = 290
FEATURE                 Location/Qualifiers
REGION                  1..290
                        note = Description of sequence: A nucleotide binding domain
                         polypeptide based on TAP1
source                  1..290
                        mol_type = protein
                        organism = Homo sapiens
SEQUENCE: 88
METEFFQQNQ TGGGGSGLQT VRSFGGGGGS GGSGLLTPLH LEGLVQFQDV SFAYPNRPDV    60
LVLQGLTFTL RPGEVTALVG PNGSGKSTVA ALLQNLYQPT GGQLLLDGKP LPQYEHRYLH    120
RQVAAVGQEP QVFGRSLQEN IAYGLTQKPT MEEITAAAVK SGAHSFISGL PQGYDTEVDE    180
AGSQLSGGQR QAVALARALI RKPSVLILDN ATSALDAGNQ LRVQRLLYES PERYSRSVLL    240
ITQHLSLVEQ ADHILFLEGG AIREGGTHQQ LMEKKGSYWA MVQAPADAPE               290

SEQ ID NO: 89           moltype = AA   length = 247
FEATURE                 Location/Qualifiers
REGION                  1..247
                        note = Description of sequence: anti-CD28 scFv
source                  1..247
                        mol_type = protein
                        organism = Homo sapiens
SEQUENCE: 89
DIELTQSPAS LAVSLGQRAT ISCRASESVE YYVTSLMQWY QQKPGQPPKL LIFAASNVES    60
```

```
GVPARFSGSG SGTNFSLNIH PVDEDDVAMY FCQQSRKVPY TFGGGTKLEI KRGGGGSGGG     120
GSGGGGSQVK LQQSGPGLVT PSQSLSITCT VSGFSLSDYG VHWVRQSPGQ GLEWLGVIWA     180
GGGTNYNSAL MSRKSISKDN SKSQVFLKMN SLQADDTAVY YCARDKGYSY YYSMDYWGQG     240
TTVTVSS                                                              247

SEQ ID NO: 90           moltype = AA  length = 518
FEATURE                 Location/Qualifiers
REGION                  1..518
                        note = Description of sequence: Single-chain IL12
source                  1..518
                        mol_type = protein
                        organism = Homo sapiens
SEQUENCE: 90
IWELKKDVYV VELDWYPDAP GEMVVLTCDT PEEDGITWTL DQSSEVLGSG KTLTIQVKEF      60
GDAGQYTCHK GGEVLSHSLL LLHKKEDGIW STDILKDQKE PKNKTFLRCE AKNYSGRFTC     120
WWLTTISTDL TFSVKSSRGS SDPQGVTCGA ATLSAERVRG DNKEYEYSVE CQEDSACPAA     180
EESLPIEVMV DAVHKLKYEN YTSSFFIRDI IKPDPPKNLQ LKPLKNSRQV EVSWEYPDTW     240
STPHSYFSLT FCVQVQGKSK REKKDRVFTD KTSATVICRK NASISVRAQD RYYSSSWSEW     300
ASVPCSGGGG SGGGGSGGGG SRNLPVATPD PGMFPCLHHS QNLLRAVSNM LQKARQTLEF     360
YPCTSEEIDH EDITKDKTST VEACLPLELT KNESCLNSRE TSFITNGSCL ASRKTSFMMA     420
LCLSSIYEDL KMYQVEFKTM NAKLLMDPKR QIFLDQNMLA VIDELMQALN FNSETVPQKS     480
SLEEPDFYKT KIKLCILLHA FRIRAVTIDR VMSYLNAS                             518

SEQ ID NO: 91           moltype = AA  length = 306
FEATURE                 Location/Qualifiers
REGION                  1..306
                        note = Description of sequence: IL12 component p40
source                  1..306
                        mol_type = protein
                        organism = Homo sapiens
SEQUENCE: 91
IWELKKDVYV VELDWYPDAP GEMVVLTCDT PEEDGITWTL DQSSEVLGSG KTLTIQVKEF      60
GDAGQYTCHK GGEVLSHSLL LLHKKEDGIW STDILKDQKE PKNKTFLRCE AKNYSGRFTC     120
WWLTTISTDL TFSVKSSRGS SDPQGVTCGA ATLSAERVRG DNKEYEYSVE CQEDSACPAA     180
EESLPIEVMV DAVHKLKYEN YTSSFFIRDI IKPDPPKNLQ LKPLKNSRQV EVSWEYPDTW     240
STPHSYFSLT FCVQVQGKSK REKKDRVFTD KTSATVICRK NASISVRAQD RYYSSSWSEW     300
ASVPCS                                                                306

SEQ ID NO: 92           moltype = AA  length = 197
FEATURE                 Location/Qualifiers
REGION                  1..197
                        note = Description of sequence: IL12 component p35
source                  1..197
                        mol_type = protein
                        organism = Homo sapiens
SEQUENCE: 92
RNLPVATPDP GMFPCLHHSQ NLLRAVSNML QKARQTLEFY PCTSEEIDHE DITKDKTSTV      60
EACLPLELTK NESCLNSRET SFITNGSCLA SRKTSFMMAL CLSSIYEDLK MYQVEFKTMN     120
AKLLMDPKRQ IFLDQNMLAV IDELMQALNF NSETVPQKSS LEEPDFYKTK IKLCILLHAF     180
RIRAVTIDRV MSYLNAS                                                    197

SEQ ID NO: 93           moltype = AA  length = 645
FEATURE                 Location/Qualifiers
REGION                  1..645
                        note = Description of sequence: single chain 4-1BBL (trimer)
source                  1..645
                        mol_type = protein
                        organism = Homo sapiens
SEQUENCE: 93
ACPWAVSGAR ASPGSAASPR LREGPELSPD DPAGLLDLRQ GMFAQLVAQN VLLIDGPLSW      60
YSDPGLAGVS LTGGLSYKED TKELVVAKAG VYYVFFQLEL RRVVAGEGSG SVSLALHLQP     120
LRSAAGAAAL ALTVDLPPAS SEARNSAFGF QGRLLHLSAG QRLGVHLHTE ARARHAWQLT     180
QGATVLGLFR VTPEIPAGLP SPRSEGGGGS GGGGSGGGGS ACPWAVSGAR ASPGSAASPR     240
LREGPELSPD DPAGLLDLRQ GMFAQLVAQN VLLIDGPLSW YSDPGLAGVS LTGGLSYKED     300
TKELVVAKAG VYYVFFQLEL RRVVAGEGSG SVSLALHLQP LRSAAGAAAL ALTVDLPPAS     360
SEARNSAFGF QGRLLHLSAG QRLGVHLHTE ARARHAWQLT QGATVLGLFR VTPEIPAGLP     420
SPRSEGGGGS GGGGSGGGGS ACPWAVSGAR ASPGSAASPR LREGPELSPD DPAGLLDLRQ     480
GMFAQLVAQN VLLIDGPLSW YSDPGLAGVS LTGGLSYKED TKELVVAKAG VYYVFFQLEL     540
RRVVAGEGSG SVSLALHLQP LRSAAGAAAL ALTVDLPPAS SEARNSAFGF QGRLLHLSAG     600
QRLGVHLHTE ARARHAWQLT QGATVLGLFR VTPEIPAGLP SPRSE                     645

SEQ ID NO: 94           moltype = AA  length = 205
FEATURE                 Location/Qualifiers
REGION                  1..205
                        note = Description of sequence: a 4-1BBL amino acid sequence
source                  1..205
                        mol_type = protein
                        organism = Homo sapiens
SEQUENCE: 94
```

```
ACPWAVSGAR ASPGSAASPR LREGPELSPD DPAGLLDLRQ GMFAQLVAQN VLLIDGPLSW    60
YSDPGLAGVS LTGGLSYKED TKELVVAKAG VYYVFFQLEL RRVVAGEGSG SVSLALHLQP   120
LRSAAGAAAL ALTVDLPPAS SEARNSAFGF QGRLLHLSAG QRLGVHLHTE ARARHAWQLT   180
QGATVLGLFR VTPEIPAGLP SPRSE                                        205

SEQ ID NO: 95             moltype = AA   length = 468
FEATURE                   Location/Qualifiers
REGION                    1..468
                          note = Description of sequence: a single-chain CD40L
                            (sequence trimer)
source                    1..468
                          mol_type = protein
                          organism = Homo sapiens
SEQUENCE: 95
GDQNPQIAAH VISEASSKTT SVLQWAEKGY YTMSNNLVTL ENGKQLTVKR QGLYYIYAQV    60
TFCSNREASS QAPFIASLCL KSPGRFERIL LRAANTHSSA KPCGQQSIHL GGVFELQPGA   120
SVFVNVTDPS QVSHGTGFTS FGLLKLGGGG SGGGGSGGGG SGDQNPQIAA HVISEASSKT   180
TSVLQWAEKG YYTMSNNLVT LENGKQLTVK RQGLYYIYAQ VTFCSNREAS SQAPFIASLC   240
LKSPGRFERI LLRAANTHSS AKPCGQQSIH LGGVFELQPG ASVFVNVTDP SQVSHGTGFT   300
SFGLLKLGGG GSGGGGSGGG GSGDQNPQIA AHVISEASSK TTSVLQWAEK GYYTMSNNLV   360
TLENGKQLTV KRQGLYYIYA QVTFCSNREA SSQAPFIASL CLKSPGRFER ILLRAANTHS   420
SAKPCGQQSI HLGGVFELQP GASVFVNVTD PSQVSHGTGF TSFGLLKL                468

SEQ ID NO: 96             moltype = AA   length = 146
FEATURE                   Location/Qualifiers
REGION                    1..146
                          note = Description of sequence: a CD40L amino acid sequence
source                    1..146
                          mol_type = protein
                          organism = Homo sapiens
SEQUENCE: 96
GDQNPQIAAH VISEASSKTT SVLQWAEKGY YTMSNNLVTL ENGKQLTVKR QGLYYIYAQV    60
TFCSNREASS QAPFIASLCL KSPGRFERIL LRAANTHSSA KPCGQQSIHL GGVFELQPGA   120
SVFVNVTDPS QVSHGTGFTS FGLLKL                                       146

SEQ ID NO: 97             moltype = AA   length = 265
FEATURE                   Location/Qualifiers
REGION                    1..265
                          note = Description of sequence: Single-chain IFNg
                            (monomeric engagement)
source                    1..265
                          mol_type = protein
                          organism = Homo sapiens
SEQUENCE: 97
MQDPYVKEAE NLKKYFNAGH SDVADNGTLF LGILKNWKEE SDRKIMQSQI VSFYFKLFKN    60
FKDDQSIQKS VETIKEDMNV KFFNSNKKKR DDFEKLTNYS VTDLNVQRKA IDELIQVMAE   120
FSTEEQQEGP YVKEAENLKK YFNAGHSDVA DNGTLFLGIL KNWKEESDRK IMQSQIVSFY   180
FKLFKNFKDD QSIQKSVETI KEDMNVKFFN SNKKKRDDFE KLTNYSVTDL NVQRKAIHEL   240
IQVMAELSPA AKTGKRKRSQ MLFRG                                        265

SEQ ID NO: 98             moltype = AA   length = 119
FEATURE                   Location/Qualifiers
REGION                    1..119
                          note = Description of sequence: Anti-CD16 VHH
source                    1..119
                          mol_type = protein
                          organism = Homo sapiens
SEQUENCE: 98
EVQLVESGGG LVQPGESLTL SCVVAGSIFS FAMSWYRQAP GKERELVARI GSDDRVTYAD    60
SVKGRFTISR DNIKRTAGLQ MNSLKPEDTA VYYCNAQTDL RDWTVREYWG QGTQVTVSS    119

SEQ ID NO: 99             moltype = AA   length = 201
FEATURE                   Location/Qualifiers
REGION                    1..201
                          note = Description of sequence: a CD80 amino acid sequence
source                    1..201
                          mol_type = protein
                          organism = Homo sapiens
SEQUENCE: 99
VIHVTKEVKE VATLSCGHNV SVEELAQTRI YWQKEKKMVL TMMSGDMNIW PEYKNRTIFD    60
ITNNLSIVIL ALRPSDEGTY ECVVLKYEKD AFKREHLAEV TLSVKADFPT PSISDFEIPT   120
SNIRRIICST SGGFPEPHLS WLENGEELNA INTTVSQDPE TELYAVSSKL DFNMTTNHSF   180
MCLIKYGHLR VNQTFNWNTT K                                            201

SEQ ID NO: 100            moltype = AA   length = 222
FEATURE                   Location/Qualifiers
REGION                    1..222
                          note = Description of sequence: CD86 (IgV-IgC)
source                    1..222
```

```
                        mol_type = protein
                        organism = Homo sapiens
SEQUENCE: 100
LKIQAYFNET ADLPCQFANS QNQSLSELVV FWQDQENLVL NEVYLGKEKF DSVHSKYMNR   60
TSFDSDSWTL RLHNLQIKDK GLYQCIIHHK KPTGMIRIHQ MNSELSVLAN FSQPEIVPIS  120
NITENVYINL TCSSIHGYPE PKKMSVLLRT KNSTIEYDGI MQKSQDNVTE LYDVSISLSV  180
SFPDVTSNMT IFCILETDKT RLLSSPFSIE LEDPQPPPDH IP                    222

SEQ ID NO: 101          moltype = AA  length = 109
FEATURE                 Location/Qualifiers
REGION                  1..109
                        note = Description of sequence: CD86 (IGV)
source                  1..109
                        mol_type = protein
                        organism = Homo sapiens
SEQUENCE: 101
LKIQAYFNET ADLPCQFANS QNQSLSELVV FWQDQENLVL NEVYLGKEKF DSVHSKYMGR   60
TSFDSDSWTL RLHNLQIKDK GLYQCIIHHK KPTGMIRIHQ MNSELSVLA             109

SEQ ID NO: 102          moltype = AA  length = 482
FEATURE                 Location/Qualifiers
REGION                  1..482
                        note = Description of sequence: scFc (wild type L234 L235;
                         including Fc hinge
source                  1..482
                        mol_type = protein
                        organism = Homo sapiens
SEQUENCE: 102
DKTHTCPPCP APELLGGPSV FLFPPKPKDT LMISRTPEVT CVVVDVSHED PEVKFNWYVD   60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGGG SGGGGSGGGG  240
SGGGGSGGGG SGGGGSDKTH TCPPCPAPEL LGGPSVFLFP PKPKDTLMIS RTPEVTCVVV  300
DVSHEDPEVK FNWYVDGVEV HNAKTKPREE QYNSTYRVVS VLTVLHQDWL NGKEYKCKVS  360
NKALPAPIEK TISKAKGQPR EPQVYTLPPS RDELTKNQVS LTCLVKGFYP SDIAVEWESN  420
GQPENNYKTT PPVLDSDGSF FLYSKLTVDK SRWQQGNVFS CSVMHEALHN HYTQKSLSLS  480
PG                                                                482

SEQ ID NO: 103          moltype = AA  length = 122
FEATURE                 Location/Qualifiers
REGION                  1..122
                        note = Description of sequence: Anti-CD16 VHH
source                  1..122
                        mol_type = protein
                        organism = Homo sapiens
SEQUENCE: 103
EVQLVESGGE LVQPGGSLRL SCAASGLTFS SYNMGWFRRA PGKEREFVAS ITWSGRDTFY   60
ADSVKGRFTI SRDNAKNTVY LQMSSLKPED TAVYYCAANP WPVAAPRSGT YWGQGTQVTV  120
SS                                                                122
```

The invention claimed is:

1. A polypeptide construct comprising a nucleotide binding domain (NBD) amino acid sequence, and a tumor-specific binder (TSB) amino acid sequence;
wherein the NBD sequence comprises one or more adenosine triphosphate (ATP) binding sites of an ATP binding cassette transporter protein and can either homodimerize or heterodimerize with a cognate non-identical NBD sequence in the presence of ATP; and
the TSB amino acid sequence comprises a sequence of an antibody, antigen binding fragment of an antibody, Fab, Fab', scFv, nanobody or aptamer that has affinity for a tumor associated antigen (TAA) expressed on the surface of a tumor cell.

2. The polypeptide construct of claim 1, further comprising a scaffold amino acid sequence.

3. A composition comprising a first polypeptide construct and a second polypeptide construct of claim 2, wherein the first polypeptide construct comprises a first NBD amino acid sequence and the second polypeptide construct comprises a second NBD amino acid sequence, and the first and the second NBD amino acid sequences are cognate sequences that may homodimerize or heterodimerize in the presence of ATP to form a homodimer or heterodimer complex.

4. The composition of claim 3, wherein the first and second polypeptide constructs homodimerize.

5. The composition of claim 4, wherein the TSB of the first polypeptide construct and the TSB of the second polypeptide construct bind to a tumor-associated antigen (TAA) selected from the group consisting of: PD-L1, mesothelin, Epithelial Cell Adhesion Molecule (EpCAM), Cytotoxic T-Lymphocyte Associated Protein 4 (CTLA-4), carbonic anhydrase IX (CAIX), cadherins, carcinoembryonic antigen (CEA), cellular-mesenchymal epithelial transition factor (c-MET), Epidermal Growth Factor Receptor (EGFR) family members, Ephrin Type-A Receptor 3 (EphA3), Fibroblast Activation Protein Alpha (FAP), folate-binding protein, Folate Receptor alpha (FR-alpha), Erb-B2 Receptor Tyrosine Kinase 2 (HER2), Erb-B2 Receptor Tyrosine Kinase 3 (HER3), Insulin Like Growth Factor 1 Receptor (IGF-1R), integrin αVβ3, integrin α5β1, Solute Carrier Family 39 Member 6 (Liv1), a Melanoma-Associated Antigen family A member (MAGEA), a Melanoma-Associated Antigen family C member (MAGEC), a mucin (e.g., MUC1), a New York Esophageal Squamous Cell Carcinoma 1 protein (NY-ESO-1, Cancer/Testis Antigen 1A, Cancer/Testis Antigen 1B), Cancer/Testis Antigen 2 (NY-ESO-2, CTAG2), Prostate-Specific Membrane Antigen (PSMA), Receptor Activator of Nuclear Factor Kappa B Ligand (RANKL), Receptor Tyrosine Kinase Like Orphan Receptor 1 (ROR1), tenascin, TNF Receptor Superfamily Member 10a (TRAILR1), TNF Receptor Superfamily Member 10b (TRAILR2), and Vascular Endothelial Growth Factor Receptor (VEGFR).

6. The composition of claim 5, wherein each scaffold comprises an immunoglobulin polypeptide sequence.

7. The composition of claim 6, wherein each scaffold comprises an immunoglobulin Fc (IgFc) amino acid sequence.

8. The composition of claim 7, wherein each scaffold comprises an independently selected non-dimerizing IgFc.

9. The composition of claim 8, wherein each IgFc polypeptide amino acid sequence may induce antibody related effector functions or each IgFc polypeptide amino acid sequence comprises one or more substitutions that enhance at least one antibody related effector function selected from antibody-dependent cell cytotoxicity, antibody-dependent cell phagocytosis, and complement-dependent cytotoxicity.

10. The composition of claim 9, wherein each NBD comprises an amino acid sequence having at least 90% sequence identity to an amino acid sequence selected from any of SEQ ID NOs: 1-7, 9, 10, 12, 15, 87, or 88.

11. The composition of claim 9, wherein the NBD comprises a TAP1 NBD.

12. The composition of claim 11, wherein the TAP1 NBD comprises an amino acid sequence of any one of SEQ ID NOs: 10, 87, or 88, or a sequence having greater than 95% sequence identity to any one of those sequences.

13. The composition of claim 3, wherein the TSB of the first polypeptide construct and the TSB of the second polypeptide construct bind to a tumor-associated antigen (TAA) selected from the group consisting of: mesothelin and EpCAM.

14. The polypeptide construct of claim 1, wherein, when the polypeptide construct is present as a monomer, homodimer, or in a heterodimer, at least one of the polypeptide constructs further comprises an immune cell engager (ICE) amino acid sequence having affinity for a protein selected from the group consisting of: CD3, CD4, CD8, αβTCR, CD2, TCRα chain, TCRβ chain, δγ TCR, TCR γ chain, TCR δ chain, TRGV9, CD84, CXCR1, CD13, CD33, CD34, and CD16.

15. The polypeptide construct of claim 1, wherein, when the polypeptide construct is present as a monomer, homodimer, or in a heterodimer, at least one of the polypeptide constructs further comprises an activating domain (AD) amino acid sequence selected from the group consisting of: 4-1BBL, anti-4-1BB, CD40L, CD28, IFN-γ, TNF superfamily members, TNF, lymphotoxin α, lymphotoxin αβ, BAFF (CD25), B7 superfamily members, CD80, CD86, IL-15, IL-2, IL-7, IL-10, IL-12, PD1, anti-CD3, anti-CTLA4, and anti-CD28 amino acid sequences.

16. A method of treating a cancer comprising administering a construct of claim 1 to a patient or subject.

17. A nucleic acid comprising a nucleotide sequence encoding one or more constructs of claim 1 or a vector comprising the nucleic acid.

18. A cell comprising the vector or nucleic acid of claim 17.

19. A composition comprising (i) a first polypeptide construct of claim 1, and (ii) a second polypeptide construct comprising an NBD amino acid sequence that comprises one or more ATP binding sites of an ATP binding cassette transporter protein and can heterodimerize with a cognate non-identical NBD of the first polypeptide construct in the presence of ATP, and an immune cell engager (ICE) amino acid sequence, wherein:
  (i) the NBD amino acid sequence of the first polypeptide construct constitutes a first heterodimerizing NBD amino acid sequence and the NBD amino acid sequence of the second polypeptide construct constitutes a second heterodimerizing NBD amino acid sequence,
  (ii) the first heterodimerizing NBD amino acid sequence is a cognate binding partner of the second heterodimerizing NBD amino acid sequence, and
  (iii) the first polypeptide construct and the second polypeptide construct bind to each other through interactions between the first heterodimerizing NBD amino acid sequence and the second heterodimerizing NBD amino acid sequence in the presence of ATP to form a heterodimer or higher order complex of the first and second polypeptide constructs.

20. The composition of claim 19, wherein:
  the TSB of the first polypeptide construct binds to a tumor-associated antigen (TAA) selected from the group consisting of mesothelin, Epithelial Cell Adhesion Molecule (EpCAM), Cytotoxic T-Lymphocyte Associated Protein 4 (CTLA-4), carbonic anhydrase IX (CAIX), cadherins, carcinoembryonic antigen (CEA), cellular-mesenchymal epithelial transition factor (c-MET), Epidermal Growth Factor Receptor (EGFR) family members, Ephrin Type-A Receptor 3 (EphA3), Fibroblast Activation Protein Alpha (FAP), folate-binding protein, Folate Receptor alpha (FR-alpha), Erb-B2 Receptor Tyrosine Kinase 2 (HER2), Erb-B2 Receptor Tyrosine Kinase 3 (HER3), Insulin Like Growth Factor 1 Receptor (IGF-1R), integrin αVβ3, integrin α5β1, Solute Carrier Family 39 Member 6 (Liv1), a Melanoma-Associated Antigen family A member (MAGEA), a Melanoma-Associated Antigen family C member (MAGEC), a mucin (e.g., MUC1), a New York Esophageal Squamous Cell Carcinoma 1 protein (NY-ESO-1, Cancer/Testis Antigen 1A, Cancer/Testis Antigen 1B), Cancer/Testis Antigen 2 (NY-ESO-2, CTAG2), Prostate-Specific Membrane Antigen (PSMA), Receptor Activator of Nuclear Factor Kappa B Ligand (RANKL), Receptor Tyrosine Kinase Like Orphan Receptor 1 (ROR1), tenascin, TNF Receptor Superfamily Member 10a (TRAILR1), TNF Receptor Superfamily Member 10b (TRAILR2), and Vascular Endothelial Growth Factor Receptor (VEGFR); and
  the ICE of the second polypeptide construct comprises a Fab, Fab', scFv, aptamer, or nanobody with affinity for a protein selected from the group consisting of: CD3, CD4, CD8, αβTCR, CD2, TCRα chain, TCRβ chain, δγ TCR, TCR γ chain, TCR δ chain, TRGV9, CD84, CXCR1, CD13, CD33, CD34, and CD16.

21. The composition of claim 19, wherein the TSB of the first polypeptide construct binds a TAA from the group consisting of: mesothelin and EpCAM.

22. The composition of claim 19, wherein the ICE has affinity for a protein selected from the group consisting of: CD3, CD4, CD8, αβTCR, CD2, TCRα chain, TCRβ chain, δγ TCR, TCR γ chain, TCR δ chain, TRGV9, CD84, CXCR1, CD13, CD33, CD34, and CD16.

23. The composition of claim 19, wherein the first and/or second polypeptide further comprises an activating domain (AD) amino acid sequence selected independently from the group consisting of: 4-1BBL, anti-4-1BB, CD40L, CD28, IFN-γ, TNF superfamily members, TNF, lymphotoxin α, lymphotoxin αβ, BAFF (CD25), B7 superfamily members, CD80, CD86, IL-15, IL-2, IL-7, IL-10, IL-12, PD1, anti-CD3, anti-CTLA4, and anti-CD28 amino acid sequences.

24. A method of treating a cancer comprising administering a composition of claim 19 to a patient or subject.

25. A nucleic acid comprising a sequence encoding one or more of the first and second polypeptide constructs of the composition of claim 19, or a vector comprising the nucleic acid.

26. A cell comprising the vector or nucleic acid of claim 25.

27. The composition of claim 19, wherein the first and second polypeptide constructs each comprise an independently selected scaffold amino acid sequence.

* * * * *